US012396641B2

(12) United States Patent
De Villers-Sidani et al.

(10) Patent No.: US 12,396,641 B2
(45) Date of Patent: *Aug. 26, 2025

(54) METHOD AND A SYSTEM FOR DETECTION OF EYE GAZE-PATTERN ABNORMALITIES AND RELATED NEUROLOGICAL DISEASES

(71) Applicant: INNODEM NEUROSCIENCES, Outremont (CA)

(72) Inventors: Etienne De Villers-Sidani, Outremont (CA); Paul Alexandre Drouin-Picaro, Montreal (CA); Yves Desgagne, Blainville (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/917,181

(22) PCT Filed: May 5, 2022

(86) PCT No.: PCT/CA2022/050703
§ 371 (c)(1),
(2) Date: Oct. 5, 2022

(87) PCT Pub. No.: WO2022/232935
PCT Pub. Date: Nov. 10, 2022

(65) Prior Publication Data
US 2025/0064365 A1 Feb. 27, 2025

Related U.S. Application Data

(63) Continuation of application No. 17/308,439, filed on May 5, 2021, now Pat. No. 11,503,998.

(51) Int. Cl.
A61B 3/113 (2006.01)
A61B 3/00 (2006.01)
(Continued)

(52) U.S. Cl.
CPC ............ *A61B 3/113* (2013.01); *A61B 3/0025* (2013.01); *A61B 3/145* (2013.01); *A61B 5/163* (2017.08);
(Continued)

(58) Field of Classification Search
CPC ....... A61B 3/113; A61B 3/0025; A61B 5/163; A61B 5/4064; A61B 5/4082;
(Continued)

(56) References Cited

U.S. PATENT DOCUMENTS 5,625,380 A 4/1997 Hansen
6,204,828 B1 3/2001 Amir et al.
(Continued)

FOREIGN PATENT DOCUMENTS

WO 2019221979 11/2019

OTHER PUBLICATIONS

International Search Report, Michael Beard, Jul. 4, 2022, 13 pages.

*Primary Examiner* — Gerald Johnson
(74) *Attorney, Agent, or Firm* — Benoit & Cote Inc.; Charles-Andre Caron

(57) ABSTRACT

The present disclosure relates to a method and a system for detecting a neurological disease and an eye gaze-pattern abnormality related to the neurological disease of a user. The method comprises displaying stimulus videos on a screen of an electronic device and simultaneously filming with a camera of the electronic device to generate a video of the user's face for each one of the stimulus videos, each one of the stimulus videos corresponding to a task. The method further comprises providing a machine learning model for gaze predictions, generating the gaze predictions for each video frame of the recorded video, and determining features for each task to detect the neurological disease using a pre-trained machine learning model.

18 Claims, 30 Drawing Sheets

(51) Int. Cl.
- *A61B 3/14* (2006.01)
- *A61B 5/00* (2006.01)
- *A61B 5/16* (2006.01)
- *G06T 7/00* (2017.01)
- *G06T 7/73* (2017.01)
- *G16H 30/40* (2018.01)
- *G16H 50/20* (2018.01)

(52) U.S. Cl.
CPC .......... *A61B 5/4064* (2013.01); *A61B 5/4082* (2013.01); *A61B 5/4842* (2013.01); *A61B 5/4863* (2013.01); *A61B 5/7267* (2013.01); *A61B 5/742* (2013.01); *G06T 7/0012* (2013.01); *G06T 7/73* (2017.01); *G16H 30/40* (2018.01); *G16H 50/20* (2018.01); *A61B 5/7207* (2013.01); *A61B 2560/0223* (2013.01); *G06T 2207/10016* (2013.01); *G06T 2207/10024* (2013.01); *G06T 2207/30041* (2013.01); *G06T 2207/30201* (2013.01)

(58) Field of Classification Search
CPC ... A61B 5/4088; A61B 5/4863; A61B 5/7267; G06T 2207/10024; G06T 2207/30204; G06T 2207/30201
See application file for complete search history.

(56) References Cited

U.S. PATENT DOCUMENTS

| | | |
|---|---|---|
| 6,243,076 B1 | 6/2001 | Hatfield |
| 6,282,553 B1 | 8/2001 | Flickner et al. |
| 6,393,136 B1 | 5/2002 | Amir |
| 6,577,329 B1 | 6/2003 | Flickner |
| 6,578,962 B1 | 6/2003 | Amir et al. |
| 6,659,611 B2 | 12/2003 | Amir et al. |
| 6,864,912 B1 | 3/2005 | Mahaffey et al. |
| 6,873,314 B1 | 3/2005 | Campbell |
| 6,886,137 B2 | 4/2005 | Peck et al. |
| 6,917,715 B2 | 7/2005 | Berstis |
| 6,919,907 B2 | 7/2005 | Berstis |
| 6,959,102 B2 | 10/2005 | Peck |
| 7,113,170 B2 | 9/2006 | Lauper et al. |
| 7,120,880 B1 | 10/2006 | Dryer et al. |
| 7,129,981 B2 | 10/2006 | Berstis |
| 7,572,008 B2 | 8/2009 | Elvesjo et al. |
| 8,025,405 B2 | 9/2011 | Rehnstrom |
| 8,066,375 B2 | 11/2011 | Skogo et al. |
| 8,120,577 B2 | 2/2012 | Bouvin et al. |
| 8,185,845 B2 | 5/2012 | Bjorklund et al. |
| 8,314,707 B2 | 11/2012 | Kobetski et al. |
| 8,339,446 B2 | 12/2012 | Blixt et al. |
| 8,342,687 B2 | 1/2013 | Blixt et al. |
| 8,348,428 B2 | 1/2013 | Martinez-Conde et al. |
| 8,439,501 B2 | 5/2013 | Newman et al. |
| 8,562,136 B2 | 10/2013 | Blixt et al. |
| 8,610,768 B2 | 12/2013 | Holmberg et al. |
| 9,131,839 B2 | 9/2015 | Seo et al. |
| 9,147,248 B2 | 9/2015 | Kaplan et al. |
| 9,179,838 B2 | 11/2015 | Skogo et al. |
| 9,317,114 B2 | 4/2016 | Hwang |
| 9,442,566 B2 | 9/2016 | Eskilsson et al. |
| 9,507,418 B2 | 11/2016 | Yu et al. |
| 9,509,910 B2 | 11/2016 | Skogo et al. |
| 9,536,097 B2 | 1/2017 | Anderson et al. |
| 9,576,316 B2 | 2/2017 | Adelmann |
| 9,580,081 B2 | 2/2017 | George-Svahn et al. |
| 9,619,020 B2 | 4/2017 | George-Svahn et al. |
| 9,646,207 B2 | 5/2017 | Kuldkepp et al. |
| 9,665,171 B1 | 5/2017 | Skogo et al. |
| 9,665,172 B2 | 5/2017 | Engwall et al. |
| 9,693,684 B2 | 7/2017 | Lopez et al. |
| 9,740,452 B2 | 8/2017 | Vennstrom et al. |
| 9,746,917 B2 | 8/2017 | Yu et al. |
| 9,760,170 B2 | 9/2017 | Elvesjo et al. |
| 9,766,699 B2 | 9/2017 | Skogo et al. |
| 9,772,690 B2 | 9/2017 | Skogoe et al. |
| 9,779,299 B2 | 10/2017 | Strombom et al. |
| 9,791,912 B2 | 10/2017 | Elvesjo et al. |
| 9,798,382 B2 | 10/2017 | Johansen et al. |
| 9,817,474 B2 | 11/2017 | George-Svahn et al. |
| 9,829,971 B2 | 11/2017 | San Agustin Lopez et al. |
| 9,829,973 B2 | 11/2017 | Vennstrom et al. |
| 9,829,976 B2 | 11/2017 | Algotsson et al. |
| 9,830,513 B2 | 11/2017 | Gustafsson et al. |
| 9,836,639 B2 | 12/2017 | Sztuk et al. |
| 9,851,791 B2 | 12/2017 | San Agustin Lopez et al. |
| 9,864,498 B2 | 1/2018 | Olsson et al. |
| 9,870,051 B2 | 1/2018 | Lovtjam et al. |
| 9,886,630 B2 | 2/2018 | Kuldkepp et al. |
| 9,898,081 B2 | 2/2018 | Thunstrom et al. |
| 9,924,864 B2 | 3/2018 | Hainzl et al. |
| 9,940,518 B1 | 4/2018 | Klingstrom et al. |
| 9,952,666 B2 | 4/2018 | Sztuk et al. |
| 9,952,883 B2 | 4/2018 | Eskilsson |
| 9,961,258 B2 | 5/2018 | Tall et al. |
| 9,962,119 B2 | 5/2018 | Macknik et al. |
| 10,013,053 B2 | 7/2018 | Cederlund et al. |
| 10,025,381 B2 | 7/2018 | Cederlund et al. |
| 10,037,086 B2 | 7/2018 | Skogo et al. |
| 10,055,495 B2 | 8/2018 | Olsson et al. |
| 10,067,561 B2 | 9/2018 | San Agustin Lopez |
| 10,082,864 B2 | 9/2018 | Kristensson et al. |
| 10,082,870 B2 | 9/2018 | Thunstrom et al. |
| 10,152,122 B2 | 12/2018 | Klingstrom |
| 10,156,899 B2 | 12/2018 | Lopez |
| 10,192,109 B2 | 1/2019 | Skogo et al. |
| 10,216,268 B2 | 2/2019 | Lindh et al. |
| 10,282,563 B2 | 5/2019 | Anderson et al. |
| 10,288,879 B1 | 5/2019 | Rana et al. |
| 10,310,597 B2 | 6/2019 | Biedert et al. |
| 10,317,995 B2 | 6/2019 | Lannsjo et al. |
| 10,324,529 B1 | 6/2019 | Rana et al. |
| 10,342,425 B1 | 7/2019 | Rana et al. |
| 10,346,128 B2 | 7/2019 | Vennstrom et al. |
| 10,372,203 B2 | 8/2019 | Skogo et al. |
| 10,394,019 B2 | 8/2019 | Ryan et al. |
| 10,394,320 B2 | 8/2019 | George-Svahn et al. |
| 10,409,388 B2 | 9/2019 | Skogo et al. |
| 10,416,725 B2 | 9/2019 | Eskilsson et al. |
| 10,460,527 B2 | 10/2019 | Ronngren |
| 10,488,919 B2 | 11/2019 | George-Svahn et al. |
| 10,528,131 B2 | 1/2020 | Davies et al. |
| 10,534,982 B2 | 1/2020 | Linden |
| 10,537,276 B2 | 1/2020 | Macknik et al. |
| 10,540,008 B2 | 1/2020 | Klingstrom et al. |
| 10,558,262 B2 | 2/2020 | Lannsjo |
| 10,558,895 B2 | 2/2020 | Linden |
| 10,565,446 B2 | 2/2020 | Gustafsson et al. |
| 10,572,008 B2 | 2/2020 | Kuldkepp et al. |
| 10,585,277 B2 | 3/2020 | Bagherpour et al. |
| 10,594,974 B2 | 3/2020 | Ivarsson et al. |
| 10,599,214 B2 | 3/2020 | George-Svahn |
| 10,607,401 B2 | 3/2020 | Lindh |
| 10,617,295 B2 | 4/2020 | Klin et al. |
| 10,671,890 B2 | 6/2020 | Linden |
| 10,678,897 B2 | 6/2020 | Skogo et al. |
| 10,685,748 B1 | 6/2020 | Chappell et al. |
| 10,686,972 B2 | 6/2020 | Ronngren |
| 10,699,663 B2 | 6/2020 | Korobkin et al. |
| 10,705,600 B2 | 7/2020 | Skogo |
| 10,712,817 B1 | 7/2020 | Ronngren |
| 10,739,851 B2 | 8/2020 | Hainzl et al. |
| 10,761,603 B2 | 9/2020 | Borge et al. |
| 2015/0335278 A1 | 11/2015 | Ashmore et al. |
| 2016/0213301 A1 | 7/2016 | Port |
| 2017/0372487 A1 | 12/2017 | Lagun et al. |
| 2018/0008141 A1 | 1/2018 | Krueger |
| 2020/0305708 A1 | 10/2020 | Krueger |
| 2020/0364453 A1 | 11/2020 | Tonsen et al. |

(56) References Cited

U.S. PATENT DOCUMENTS

2021/0330185 A1\* 10/2021 Krukowski ........ G02B 26/0833
2022/0351545 A1\* 11/2022 Ben-Ami ............... G06V 40/18

\* cited by examiner

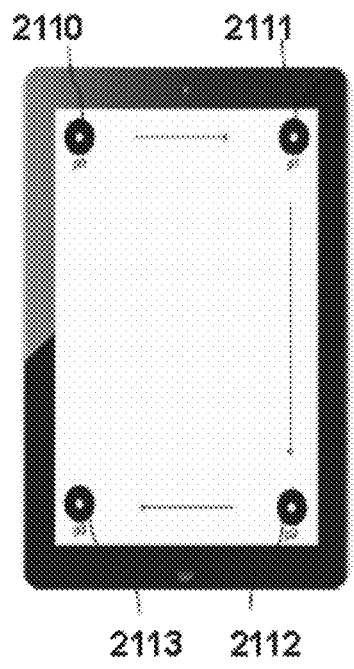 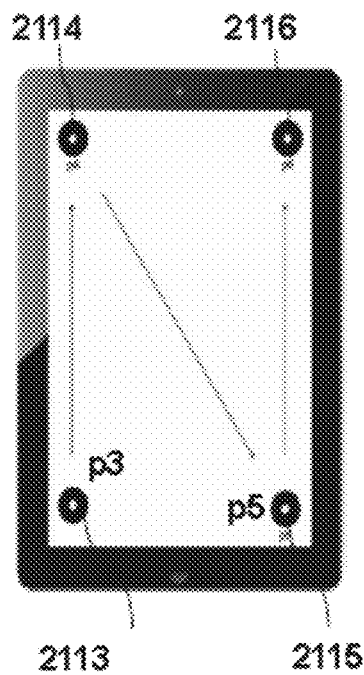 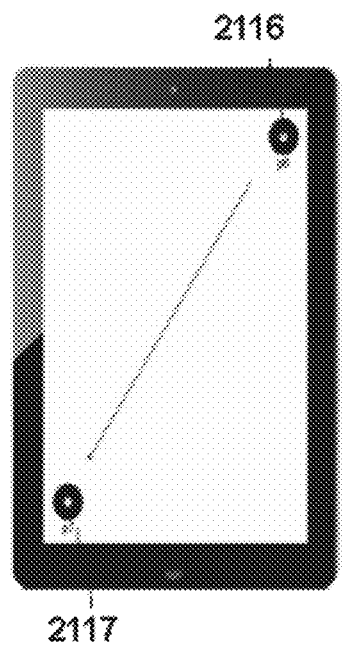
FIG. 21A    FIG. 21B    FIG. 21C
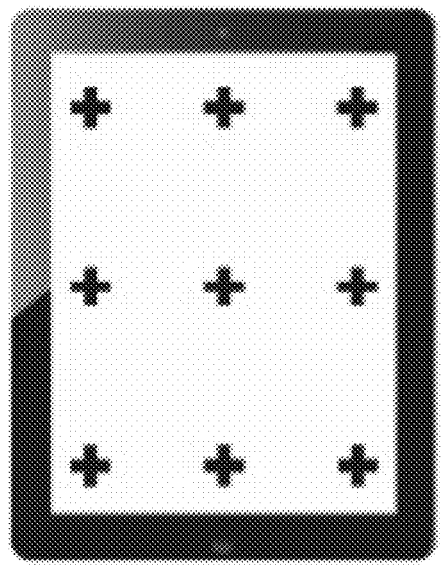
FIG. 22A

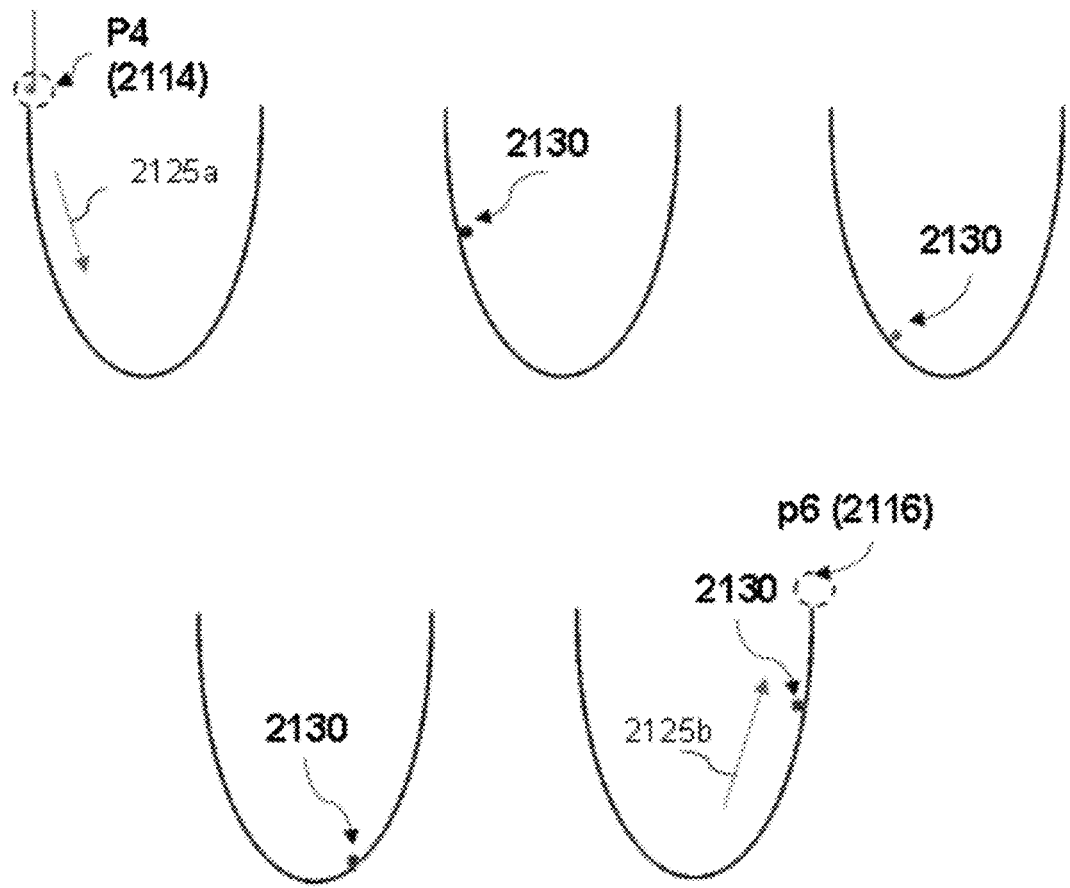
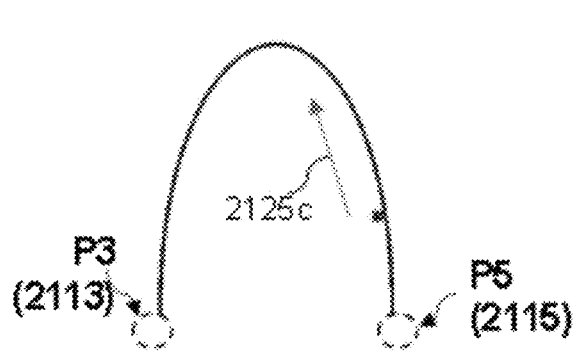
FIG. 21E
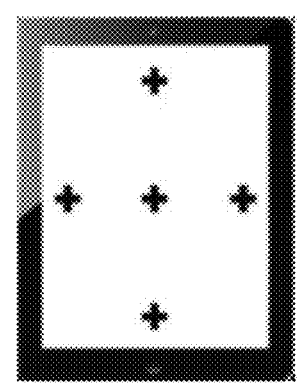
FIG. 22B

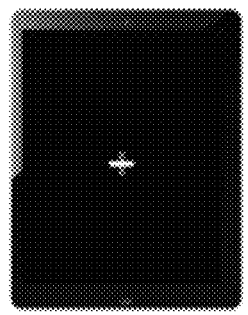 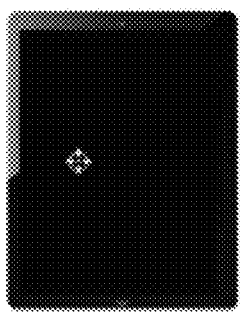 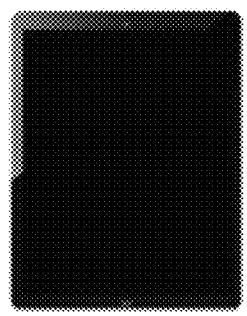 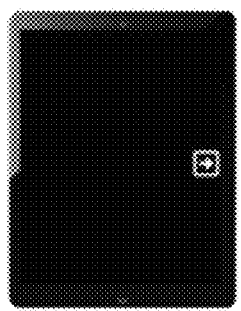
FIG. 24E     FIG. 24F     FIG. 24G     FIG. 24H
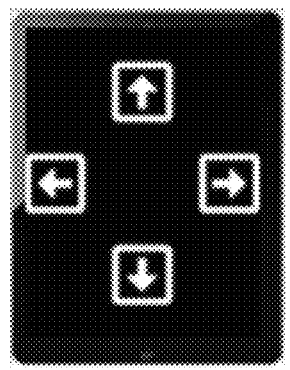
FIG. 24I
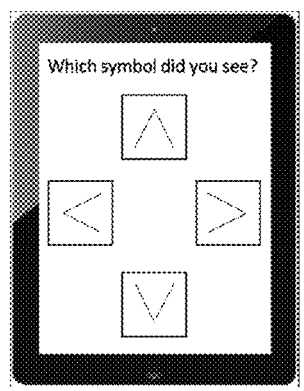
FIG. 25

*Equivalent to 92px wide, assuming iPad 6 pixel dimensions of width = 1563 px, height = 2048 px

250

| Step 251: providing an electronic device comprising a screen for display and a camera in proximity to the screen |

| Step 252: performing an eye gaze-pattern test by displaying targets on the screen while filming with the camera to receive a video of the user's face, said tests including for example: fixation, pro-saccades, anti-saccades, and optokinetic nystagmus. |

| Step 253: determining an estimated gaze position over time in the video, preferably for each eye, using the method for gaze-tracking as described (OPTIONAL) |

| Step 254: extracting features from the video of the user's face, wherein the features are extracted from the angular movement of at least one eye in the video and comprising at least one of: square wave jerk, square wave pulse, ocular flutter, opsoclonus, and an amplitude, a frequency, a velocity or a direction of a nystagmus |

| Step 255: identifying eye movements in association to the eye gaze-pattern test being performed and detecting an eye gaze-pattern abnormality in the video (or in the estimated gaze position) over time as determined using a trained machine learning algorithm |

FIG. 33A

260

| Step 261: providing an electronic device comprising a screen for display and a camera in proximity to the screen |

| Step 262: performing, for a first time period, an eye gaze-pattern test by displaying a sequence of targets on the screen and simultaneously filming with the camera to generate a video of the user's face during the first time period |

| Step 263: determining a first set of features based on the video of the user's face and the sequence of targets displayed on the screen during the first time period |

| Step 264: detecting the eye gaze-pattern abnormality based on the first set of features determined based on the video of the user's face; |

FIG. 33B

METHOD AND A SYSTEM FOR DETECTION OF EYE GAZE-PATTERN ABNORMALITIES AND RELATED NEUROLOGICAL DISEASES

RELATED APPLICATION

This application is a US National Phase application under 35 USC § 371 of PCT/CA2022/050703, filed on May 5, 2022, which claims priority or benefit of U.S. patent application Ser. No. 17/308,439 filed on May 5, 2021, the specifications of which is incorporated herein by reference in its entirety.

TECHNICAL FIELD

The present description generally relates to eye tracking methods and systems, and more particularly relates to methods and systems for detection of eye gaze-pattern using a camera and not requiring any other tracking device.

BACKGROUND

Eye movements are extremely fast and precise. Various neurological and psychiatric disorders may affect the eye movements and sequences of eye-movements of a person.

The existing eye-gaze tracking solutions require the use of dedicated hardware, such as, for example, infrared cameras, thereby reducing the availability and increasing the cost of such technology. For example, eye tracking systems designed for paralyzed individuals are so expensive that they are unaffordable for most patients and clinical units.

Moreover, existing technologies are bulky and usually require a professional operator to determine a particular neurological condition. Therefore, there is a need for an improved technology for detection of the eye movement abnormalities which would help to determine various neurological conditions.

SUMMARY

The present disclosure provides methods, systems and apparatuses for detecting a neurological disease and an eye gaze-pattern abnormality related to the neurological disease of a user.

According to one aspect of the disclosed technology, there is provided a method for detecting a neurological disease, the method comprising: displaying stimulus videos on a screen of an electronic device and simultaneously filming with a camera of the electronic device, the camera located in proximity to the screen, to generate a video of the user's face for each one of the stimulus videos, each one of the stimulus videos corresponding to a task of a set of tasks, one task of the set of tasks being a calibration task; providing a machine learning model for gaze predictions; based on the generated videos for the tasks and using the machine learning model, generating the gaze predictions for each video frame of each video of the user's face for each task; based on the generated gaze predictions for each video frame of each video of the user's face for each task, determining features for each task; and based on the features determined for each task, detecting a neurological disease using a pre-trained machine learning model.

In some embodiments, providing the machine learning model comprises using another pre-trained model into which calibration data obtained during the calibration task is fed to perform the gaze predictions. Using the other pre-trained model may comprise using an internal representation of the machine learning model to perform the gaze predictions. In some embodiments, providing the machine learning model comprises generating a user-specific machine learning model by using calibration data obtained during the calibration task to train layers of another pre-trained machine learning model. In some embodiments, providing the machine learning model comprises generating new models using calibration data obtained during the calibration task.

In at least one embodiment, the features are extracted from an angular movement overtime of at least one eye in the video of the user's face. Detecting the neurological disease may comprise determining an eye gaze-pattern abnormality related to the neurological disease and determining the eye gaze-pattern abnormality comprises identifying eye movements in association to the stimulus videos being displayed. Detecting the neurological disease may comprise determining the eye gaze-pattern abnormality which comprises determining an estimated gaze position overtime in the video. Generating the gaze predictions may further comprise determining an estimated gaze position overtime in the video by: receiving an image of at least one eye of the user from the video; extracting at least one color component of the image to obtain a corresponding at least one component image; for each one of the at least one component of the image, applying a respective primary stream to obtain a respective internal representation; and determining the estimated gaze position in the image according to the respective internal representation of each one of the at least one component of the image.

In some embodiments, the set of tasks further comprises at least one of a fixation task, a pro-saccade task, an anti-saccade task, an optokinetic nystagmus task, a smooth pursuit task, a spiral task, and a picture free-viewing task, and wherein: the features for the fixation task comprise at least one of: an average gaze position, an average gaze error, a number of saccadic intrusions, presence of nystagmus, direction of nystagmus, and a velocity of nystagmus; the features for the pro-saccade task comprise at least one of: a saccade latency, vertical and horizontal saccade latencies, a peak saccade velocity, vertical and horizontal peak saccade velocity, a saccade endpoint accuracy, a number of reversals in acceleration, and a direction error rate; the features for the anti-saccade task comprise at least one of: an arrow direction error rate, a saccade direction error rate, a correction rate, a saccade latency, and a peak saccade velocity; the features for the optokinetic nystagmus task comprise at least one of: presence of nystagmus, velocity of nystagmus in a slow phase, velocity of nystagmus in a fast phase, a direction of nystagmus, an amplitude of nystagmus; the features for the smooth pursuit task comprise at least one of: a velocity gain, an average lag, a number of reversals in acceleration, a gaze direction error, and time to correct gaze direction; and the features for the spiral task comprise at least one of: an average gaze position error relative to stimulus for each trial, a deviation from stimulus path, an angular velocity error, maximal angular velocity, a measure of circularity of gaze pattern during each spiral revolution, and time during the trial at which error on position reaches a certain threshold. In some embodiments, each one of the stimulus videos comprises displaying a sequence of targets on the screen for the task, and the set of tasks further comprises: a fixation task, a pro-saccade task, an anti-saccade task, an optokinetic nystagmus task, a smooth pursuit task, a spiral task, and a picture free-viewing task.

According to a further aspect of the disclosed technology, there is provided a method for detecting a neurological disease, the method comprising: displaying stimulus videos on a screen of an electronic device and simultaneously filming with a camera of the electronic device, the camera located in proximity to the screen, to generate a video of the user's face for each one of the stimulus videos, each one of the stimulus videos corresponding to a task of a set of tasks; based on the generated video for each task, determine features for each task using a first pre-trained machine learning model; and based on the features determined for each task, detecting a neurological disease using a second pre-trained machine learning model. Each one of the first pre-trained machine learning model and the second pre-trained machine learning model may comprise one machine learning model for the features of each task. Using the first pre-trained machine learning model may comprise using a plurality of machine learning models, each one of the plurality of machine learning models directed to a corresponding one of the features. Providing the machine learning model for the gaze predictions may comprise providing a plurality of machine learning models, each one of the plurality of machine learning models directed to a corresponding one of the features. The method may further comprise detecting a progression of the neurological disease. The detecting the neurological disease may comprise determining an eye gaze-pattern abnormality related to the neurological disease.

In at least one embodiment, each one of the stimulus videos comprises displaying a sequence of targets on the screen for the task, and the set of tasks further comprises: a fixation task, a pro-saccade task, an anti-saccade task, an optokinetic nystagmus task, a smooth pursuit task, a spiral task, and a picture free-viewing task. The methods may further comprise detecting a progression of the neurological disease.

In some embodiments, the set of tasks may further comprise at least one of a fixation task, a pro-saccade task, an anti-saccade task, an optokinetic nystagmus task, a smooth pursuit task, a spiral task, and a picture free-viewing task, and, in some embodiments, the features for the fixation task comprise at least one of: an average gaze position, an average gaze error, a number of saccadic intrusions, presence of nystagmus, direction of nystagmus, and a velocity of nystagmus; the features for the pro-saccade task comprise at least one of: a saccade latency, vertical and horizontal saccade latencies, a peak saccade velocity, vertical and horizontal peak saccade velocity, a saccade endpoint accuracy, a number of reversals in acceleration, and a direction error rate; the features for the anti-saccade task comprise at least one of: an arrow direction error rate, a saccade direction error rate, a correction rate, a saccade latency, and a peak saccade velocity; the features for the optokinetic nystagmus task comprise at least one of: presence of nystagmus, velocity of nystagmus in a slow phase, velocity of nystagmus in a fast phase, a direction of nystagmus, an amplitude of nystagmus; the features for the smooth pursuit task comprise at least one of: a velocity gain, an average lag, a number of reversals in acceleration, a gaze direction error, and time to correct gaze direction; and the features for the spiral task comprise at least one of: an average gaze position error relative to stimulus for each trial, a deviation from stimulus path, an angular velocity error, maximal angular velocity, a measure of circularity of gaze pattern during each spiral revolution, and time during the trial at which error on position reaches a certain threshold. In various embodiments, the set of tasks may comprise various combinations of a fixation task, a pro-saccade task, an anti-saccade task, an optokinetic nystagmus task, a smooth pursuit task, a spiral task, and a picture free-viewing task.

According to a further aspect of the disclosed technology, there is provided a method for detecting a neurological disease, the method comprising: displaying a set of stimulus videos on a screen of an electronic device and simultaneously filming with a camera of the electronic device, the camera located in proximity to the screen, to generate a video of the user's face for each one of the stimulus videos, each one of the stimulus videos corresponding to a task of a set of tasks, the set of tasks further comprising: a fixation task, a pro-saccade task, an anti-saccade task, a nystagmus task, a smooth pursuit task, a spiral task, and a picture free-viewing task; and based on the generated videos, detecting the neurological disease using a pre-trained machine learning model. The set of tasks may comprise at least one of: a fixation task, a pro-saccade task, an anti-saccade task, a nystagmus task, a smooth pursuit task, a spiral task, and a picture free-viewing task. Advantageously, at least two of the tasks, or a plurality of tasks, can be performed to obtain more corresponding features. The method may further comprise detecting a progression of the neurological disease. The detecting the neurological disease may comprise determining an eye gaze-pattern abnormality related to the neurological disease. Detecting the neurological disease using a pre-trained machine learning model may further comprise determining features for each task.

According to a further aspect of the disclosed technology, there is provided a method for detecting an eye gaze-pattern abnormality related to a neurological disease of a user, the method comprising the steps of: providing an electronic device comprising a screen for display and a camera in proximity to the screen; displaying, for a first period of time, a sequence of targets on the screen and simultaneously filming with the camera to capture a video of the user's face, the sequence of targets comprising a fixation target and a plurality of spirals displayed sequentially, each spiral of the plurality of spirals being displayed after displaying the fixation target on the screen for a second period of time; determining at least one feature based on the video of the user's face; and detecting the eye gaze-pattern abnormality based on the at least one feature determined based on the video of the user's face. In at least one embodiment, the plurality of spirals comprises two clockwise spirals and two counterclockwise spirals, and each one of the plurality of spirals revolving around the fixation target. The plurality of spirals may comprise a fast clockwise spiral, a slow clockwise spiral, a fast counter clockwise spiral and a slow counter clockwise spiral, the fast clockwise spiral being displayed for a shorter period of time than the slow clockwise spiral, and the fast counter clockwise spiral being displayed for a shorter period of time than the slow counter clockwise spiral.

Displaying the sequence of targets may further comprise: displaying the fixation target at a fixation target position for a second period of time; displaying a slow clockwise spiral starting from the fixation target position and revolving around the fixation target position for a third period of time; displaying the fixation target at the fixation target position for a fourth period of time; displaying a fast clockwise spiral starting from the fixation target position and revolving around the fixation target position for a fifth period of time, the fast clockwise spiral being displayed for a shorter period of time than the slow clockwise spiral; displaying the fixation target at the fixation target position for a sixth period of time; displaying a slow counter clockwise spiral starting from the fixation target position and revolving around the fixation target position for a seventh period of time; displaying the fixation target at the fixation target position for an eight period of time; and displaying a fast counter clockwise spiral starting from the fixation target position and revolving around the fixation target position for a ninth period of time, the fast counter clockwise spiral being displayed for a shorter period of time than the slow counter clockwise spiral.

According to a further aspect of the disclosed technology, there is provided a system for detecting a neurological disease of a user, the system comprising: an electronic device comprising a screen and a camera located in proximity to the screen, the screen being configured to display stimulus videos and the camera being configured to film and generate a video of a user's face; a memory storing stimulus videos; a processing unit and a non-transitory computer readable medium with computer executable instructions stored thereon that, when executed by the processing unit, cause the processing unit to: display the stimulus videos on the screen of the electronic device and simultaneously film with the camera to generate the video of the user's face for each one of the stimulus videos, each one of the stimulus videos corresponding to a task of a set of tasks, one task of the set of tasks being a calibration task; provide a machine learning model for gaze predictions; based on the generated videos for the tasks and using the machine learning models, generate gaze predictions for each video frame of each video of the user's face for each task; based on the generated gaze predictions for each video frame of each video of the user's face for each task, determine features for each task; and based on the features determined for each task, detect a neurological disease using a pre-trained machine learning model.

According to a further aspect of the disclosed technology, there is provided a system for detecting a neurological disease of a user, the system comprising: an electronic device comprising a screen and a camera located in proximity to the screen, the screen being configured to display stimulus videos and the camera being configured to film and generate a video of a user's face; a memory storing stimulus videos, and a processing unit and a non-transitory computer readable medium with computer executable instructions stored thereon that, when executed by the processing unit, cause the processing unit to: display stimulus videos on the screen of the electronic device and simultaneously film with the camera to generate a video of the user's face for each one of the stimulus videos, each one of the stimulus videos corresponding to a task of a set of tasks; based on the generated video for each task, determine features for each task using a first pre-trained machine learning model; and based on the features determined for each task, detect a neurological disease using a second pre-trained machine learning model.

According to a further aspect of the disclosed technology, there is provided a system for detecting a neurological disease of a user, the system comprising: an electronic device comprising a screen and a camera located in proximity to the screen, the screen being configured to display stimulus videos and the camera being configured to film and generate a video of a user's face; a memory storing stimulus videos, and a processing unit and a non-transitory computer readable medium with computer executable instructions stored thereon that, when executed by the processing unit, cause the processing unit to: display a set of stimulus videos on the screen and simultaneously filming with the camera to generate the video of the user's face for each one of the stimulus videos, each one of the stimulus videos corresponding to a task of a set of tasks, the set of tasks further comprising: a fixation task, a pro-saccade task, an anti-saccade task, a nystagmus task, a smooth pursuit task, a spiral task, and a picture free-viewing task; and based on the generated videos, detect the neurological disease using a pre-trained machine learning model.

According to a further aspect of the disclosed technology, there is provided a method for detecting an eye gaze-pattern abnormality related to a neurological disease of a user. The method comprises the steps of: providing an electronic device comprising a screen for display and a camera in proximity to the screen; performing, for a first time period, an eye gaze-pattern test by displaying a sequence of targets on the screen and simultaneously filming with the camera to generate a video of the user's face during the first time period; determining a first set of features based on the video of the user's face and the sequence of targets displayed on the screen during the first time period; and detecting the eye gaze-pattern abnormality based on the first set of features determined based on the video of the user's face. In at least one embodiment, determining the first set of features comprises applying a first trained machine learning algorithm to the video. In at least one embodiment, detecting the eye gaze-pattern abnormality comprises applying a second trained machine learning algorithm to the first set of features.

In at least one embodiment, a trained machine learning algorithm determines, based on the video, which features to be included in the first set of features to determine an eye gaze-pattern abnormality.

In at least one embodiment, the eye gaze-pattern test comprises a first task and a second task; the sequence of targets comprises a first sequence of targets corresponding to the first task and a second sequence of targets corresponding to the second task; the first set of features is determined based on the first task and a portion of the video captured during the first task; and the method further comprises: determining a second set of features based on the second task, and detecting the eye gaze-pattern abnormality based on the first set of features and the second set of features.

In some implementations, the method further comprises detecting progression of the eye gaze-pattern abnormality related to the neurological disease by comparing the first set of features with another set of preceding features determined based on another video of the user's face filmed during a second time period. Detecting the eye gaze-pattern abnormality may comprise identifying eye movements in association to the eye gaze-pattern test being performed. The first task and the second task may be at least two of: a fixation task corresponding to an eye fixation set of features, a pro-saccade task corresponding to a pro-saccade set of features, an anti-saccade task corresponding to an anti-saccade set of features, an optokinetic nystagmus task corresponding to an optokinetic nystagmus set of features, and a spiral task corresponding to a spiral set of features.

In at least one embodiment, the eye fixation set of features comprises: an average gaze position, an average gaze error, a number of saccadic intrusions, presence of nystagmus, a direction of nystagmus, and a velocity of nystagmus. In at least one embodiment, the pro-saccade set of features comprises: a saccade latency, vertical and horizontal saccade latencies, a peak saccade velocity, vertical and horizontal peak saccade velocity, a saccade endpoint accuracy, a number of reversals in acceleration, a direction error rate. In at least one embodiment, the anti-saccade set of features comprises: an arrow direction error rate, a saccade direction error rate, a correction rate, the saccade latency, the peak saccade velocity. In at least one embodiment, the optokinetic nystagmus set of features comprises: a velocity gain, an average lag, a number of reversals in acceleration, a gaze direction error, time to correct gaze direction.

The method may further comprise identifying and removing artifacts in eye movements. The method may further comprise determining an estimated gaze position over time in the video for each eye. The determining the estimated gaze position over time in the video may comprise: receiving an image of at least one eye of the user from the video; extracting at least one color component of the image to obtain a corresponding at least one component image; for each one of the at least one component image, applying a respective primary stream to obtain a respective internal representation; and determining the estimated gaze position in the image according to the respective internal representation of each of the at least one component image. Detecting the eye gaze-pattern abnormality may comprise applying a trained machine learning algorithm on the estimated gaze position over time in the video.

In at least one embodiment, the first set of features is an eye fixation set of features comprising: an average gaze position, an average gaze error, a number of saccadic intrusions, presence of nystagmus, direction of nystagmus, and a velocity of nystagmus. In at least one embodiment, the first set of features is a pro-saccade set of features comprising: a saccade latency, vertical and horizontal saccade latencies, a peak saccade velocity, vertical and horizontal peak saccade velocity, a saccade endpoint accuracy, a number of reversals in acceleration, and a direction error rate. In at least one embodiment, the first set of features is an anti-saccade set of features comprising: an arrow direction error rate, a saccade direction error rate, a correction rate, a saccade latency, and a peak saccade velocity. In at least one embodiment, the first set of features is the optokinetic nystagmus set of features comprising: a velocity gain, an average lag, a number of reversals in acceleration, a gaze direction error, and time to correct gaze direction. In at least one embodiment, the first set of features are extracted from an angular movement over time of at least one eye in the video of the user's face.

According to a further aspect of the disclosed technology, a method for detecting an eye gaze-pattern abnormality related to a neurological disease of a user is provided. The method comprises the steps of: providing an electronic device comprising a screen for display and a camera in proximity to the screen; displaying, for a first period of time, a sequence of targets on the screen and simultaneously filming with the camera to capture a video of the user's face, the sequence of targets comprising a fixation target and a plurality of spirals displayed sequentially, each spiral of the plurality of spirals being displayed after displaying the fixation target on the screen for a second period of time; determining at least one feature based on the video of the user's face; and detecting the eye gaze-pattern abnormality based on the at least one feature determined based on the video of the user's face. In at least one embodiment, the plurality of spirals comprises two clockwise spirals and two counterclockwise spirals, and each one of the plurality of spirals revolving around the fixation target. In at least one embodiment, the plurality of spirals comprises a fast clockwise spiral, a slow clockwise spiral, a fast counter clockwise spiral and a slow counter clockwise spiral, the fast clockwise spiral being displayed for a shorter period of time than the slow clockwise spiral, and the fast counter clockwise spiral being displayed for a shorter period of time than the slow counterclockwise spiral. In some implementation, displaying the sequence of targets further comprises: displaying the fixation target at a fixation target position for a second period of time; displaying a slow clockwise spiral starting from the fixation target position and revolving around the fixation target position for a third period of time; displaying the fixation target at the fixation target position for a fourth period of time; displaying a fast clockwise spiral starting from the fixation target position and revolving around the fixation target position for a fifth period of time, the fast clockwise spiral being displayed for a shorter period of time than the slow clockwise spiral; displaying the fixation target at the fixation target position for a sixth period of time; displaying a slow counter clockwise spiral starting from the fixation target position and revolving around the fixation target position for a seventh period of time; displaying the fixation target at the fixation target position for an eight period of time; and displaying a fast counter clockwise spiral starting from the fixation target position and revolving around the fixation target position for a ninth period of time, the fast counter clockwise spiral being displayed for a shorter period of time than the slow counter clockwise spiral.

According to a further aspect of the disclosed technology, there is provided a non-transitory computer readable medium with computer executable instructions stored thereon that, when executed by a processing unit, cause the processing unit to: perform, for a first time period, an eye gaze-pattern test by causing the screen to display a sequence of targets and receive the video of the user's face captured by the camera during the first time period; determine a first set of features based on the video of the user's face and the sequence of targets displayed on the screen during the first time period; and detect the eye gaze-pattern abnormality based on the first set of features determined based on the video of the user's face.

According to a further aspect of the disclosed technology, there is provided a system for detecting an eye gaze-pattern abnormality related to a neurological disease of a user, the system comprising: an electronic device comprising a screen for display and a camera in proximity to the screen, the screen being configured to display a sequence of targets and the camera being configured to film and generate a video of a user's face; a memory having a description of the sequence of targets; a processing unit and a non-transitory computer readable medium with computer executable instructions stored thereon that, when executed by the processing unit, cause the processing unit to: perform, for a first time period, an eye gaze-pattern test by causing the screen to display a sequence of targets and receive the video of the user's face captured by the camera during the first time period; determine a first set of features based on the video of the user's face and the sequence of targets displayed on the screen during the first time period; and detect the eye gaze-pattern abnormality based on the first set of features determined based on the video of the user's face.

According to a further aspect of the disclosed technology, there is provided a non-transitory computer readable medium with computer executable instructions stored thereon that, when executed by a processing unit, cause the processing unit to: display, for a first period of time, a sequence of targets on the screen and simultaneously filming with the camera to capture a video of the user's face, the sequence of targets comprising a fixation target and a plurality of spirals displayed sequentially, each spiral of the plurality of spirals being displayed after displaying the fixation target on the screen for a second period of time; determine at least one feature based on the video of the user's face; and detect the eye gaze-pattern abnormality based on the at least one feature determined based on the video of the user's face.

According to a further aspect of the disclosed technology, there is provided a system for detecting an eye gaze-pattern abnormality related to a neurological disease of a user, the system comprising: an electronic device comprising a screen for display and a camera in proximity to the screen, the screen being configured to display a sequence of targets and the camera being configured to film and generate a video of a user's face simultaneously with the displaying of the sequence of the targets; a memory having a description of the sequence of targets, and a processing unit and a non-transitory computer readable medium with computer executable instructions stored thereon that, when executed by the processing unit, cause the processing unit to: display, for a first period of time, a sequence of targets on the screen and receive the video of the user's face, the sequence of targets comprising a fixation target and a plurality of spirals displayed sequentially, each spiral of the plurality of spirals being displayed after displaying the fixation target on the screen for a second period of time; determine at least one feature based on the video of the user's face; and detect the eye gaze-pattern abnormality based on the at least one feature determined based on the video of the user's face.

In at least one embodiment, the first set of features comprises at least one of: square wave jerk, square wave pulse, ocular flutter, opsoclonus, and an amplitude, a frequency, a velocity or a direction of a nystagmus. In at least one embodiment, extracting features from the video of the user's face, and detecting the eye gaze-pattern abnormality is performed using the features extracted from the video. In at least one embodiment, performing the eye gaze-pattern test comprises performing a plurality of tasks directed to at least two of: eye fixation, pro-saccades, anti-saccades, optokinetic nystagmus, and spiral.

In at least one embodiment, identifying and removing artifacts in eye movements comprises identifying a blink using a sequence of images in the video and removing the blink from consideration when identifying eye movements.

In at least one embodiment, the electronic device comprises any one chosen among: a tablet, a smartphone, a laptop computer, a handheld computer; and a tabletop computer comprising the screen having the camera.

According to a further aspect of the disclosed technology, there is provided a method for detecting an eye gaze-pattern abnormality related to a neurological disease. The method comprises: displaying stimulus videos on a screen of an electronic device and simultaneously filming with a camera of the electronic device, the camera located in proximity of the screen, to generate a video of the user's face for each one of the stimulus videos, each one of the stimulus videos corresponding to a task of a set of tasks, one task of the set of tasks being a calibration task; generating machine learning models for gaze predictions; based on the generated videos for the tasks and using the machine learning models, generating gaze predictions for each video frame of each video of the user's face for each task; based on the generated gaze predictions for each video frame of each video of the user's face for each task, determine features for each task; and based on the features determined for each task, detecting a neurological disease using a pre-trained machine learning model.

According to a further aspect of the disclosed technology, there is provided a method for detecting an eye gaze-pattern abnormality related to a neurological disease. The method comprises: displaying stimulus videos on a screen of an electronic device and simultaneously filming with a camera of the electronic device, the camera located in proximity of the screen, to generate a video of the user's face for each one of the stimulus videos, each one of the stimulus videos corresponding to a task of a set of tasks; based on the generated video for each task, determine features for each task using a first pre-trained machine learning model; and based on the features determined for each task, detecting a neurological disease using a second pre-trained machine learning model.

According to a further aspect of the disclosed technology, there is provided a method for detecting a neurological disease, the method comprising: displaying a set of stimulus videos on a screen of an electronic device and simultaneously filming with a camera of the electronic device, the camera located in proximity of the screen, to generate a video of the user's face for each one of the stimulus videos, each one of the stimulus videos corresponding to a task of a set of tasks; and based on the generated videos, detecting the neurological disease using a pre-trained machine learning model. The method may further comprise detecting a progression of the neurological disease.

In at least one embodiment, stimulus video of the set of the stimulus videos comprises displaying a sequence of targets on the screen for the task, the set of tasks further comprising: a fixation task, a pro-saccade task, an anti-saccade task, a nystagmus task, a smooth pursuit task, a spiral task, and an image fixation task. Determining the eye gaze-pattern abnormality related to the neurological disease may comprise determining the neurological disease. Detecting the neurological disease may comprise determining the eye gaze-pattern abnormality related to the neurological disease. Detecting the eye gaze-pattern abnormality related to the neurological disease may comprise detecting progression of the eye gaze-pattern abnormality related to the neurological disease.

According to a further aspect of the disclosed technology, a method for detecting a neurological disease is provided, the method comprising: performing a set of tasks, each task being distinct from each other and corresponding to a distinct set of features for the task, the set of tasks having a calibration task, and at least one of a smooth pursuit task, a fixation task, a pro-saccade task and an anti-saccade task, performing a set of tasks comprising, for each task, displaying stimulus videos on a screen of an electronic device and simultaneously filming with a camera of the electronic device, the camera located in proximity to the screen, to generate a video of a user's face for each one of the stimulus videos, each one of the stimulus videos corresponding to a task of the set of tasks, a stimulus video comprising displaying a target in a sequence on the screen following a predetermined continuous or disconnected path and the target appearing moving at a pre-determined speed on the screen, the stimulus video prompting the user to deliberately follow the movement of the target on the screen during displaying of the stimulus video, each one of the stimulus video being configured for extraction of the distinct set of features; providing a machine learning model for gaze predictions; based on the generated videos for the tasks and using the machine learning model, generating the gaze predictions for each video frame of each video of the user's face for each task; based on the generated gaze predictions for each video frame of each video of the user's face for each task, determining values of the set of features for each task; and based on the values of the set of features determined for each task, detecting the neurological disease using a pre-trained machine learning model. In at least one embodiment, the calibration task comprises performing an alignment of the eyes of the user with respect to a form displayed on the screen, requesting the user to tilt the head to one side during a first period of the calibration task and to another side during a second period of the calibration task. The method may further comprise determining, during the fixation task, metrics related to intrusions, the method may comprising a square-wave jerk (SWJ) saccade metrics and other saccadic intrusions metrics, and metrics related to gaze drift and stability. During the pro-saccade task, following a displaying of a first target for a period of time, a second target may be displayed in one of a set of pre-determined locations on the screen, and the following metrics may be extracted: a first gain and a final gain, a saccadic velocity, a ratio of the peak velocity between both eyes, and a number of saccades required to reach a target. In at least one embodiment, the anti-saccade task comprises at least three distinct video blocks, each video block being configured to present on the screen a pre-determined number of trials, each trial having a fixation period, a blank screen period and a stimulus period.

The set of tasks further may further comprise an optokinetic nystagmus task which comprises displaying a contrast grating for a pre-determined period of time, the contrast grating moving across the screen. Metrics may be determined for each pair of slow drift and saccade, and based on the metrics, values of the set of features for the optokinetic nystagmus task may be determined. Providing the machine learning model may comprise using another pre-trained model into which calibration data obtained during the calibration task is fed to perform the gaze predictions, and using the other pre-trained model comprises using an internal representation of the machine learning model to perform the gaze predictions. The set of tasks may further comprise a fixation task, a pro-saccade task, an anti-saccade task, an optokinetic nystagmus task, a smooth pursuit task, a spiral task, and a picture free-viewing task. In at least one embodiment, the set of tasks further comprises at least one of an optokinetic nystagmus task, a smooth pursuit task, a spiral task, and a picture free-viewing task, and wherein: the set of features for the fixation task comprises at least one of: an average gaze position, an average gaze error, a number of saccadic intrusions, presence of nystagmus, direction of nystagmus, and a velocity of nystagmus; the set of features for the pro-saccade task comprises at least one of: a saccade latency, vertical and horizontal saccade latencies, a peak saccade velocity, vertical and horizontal peak saccade velocity, a saccade endpoint accuracy, a number of reversals in acceleration, and a direction error rate; the set of features for the anti-saccade task comprises at least one of: an arrow direction error rate, a saccade direction error rate, a correction rate, a saccade latency, and a peak saccade velocity; the set of features for the optokinetic nystagmus task comprises at least one of: presence of nystagmus, velocity of nystagmus in a slow phase, velocity of nystagmus in a fast phase, a direction of nystagmus, an amplitude of nystagmus; the set of features for the smooth pursuit task comprises at least one of: a velocity gain, an average lag, a number of reversals in acceleration, a gaze direction error, and time to correct gaze direction; and the set of features for the spiral task comprises at least one of: an average gaze position error relative to stimulus for each trial, a deviation from stimulus path, an angular velocity error, maximal angular velocity, a measure of circularity of gaze pattern during each spiral revolution, and time during the trial at which error on position reaches a certain threshold.

Displaying the sequence of targets may comprise displaying a target in a sequence on the screen following a predetermined continuous path and the target appearing moving at a constant speed towards and from one of four extremes of the screen, the smooth pursuit task comprising prompting the user to follow the path of the target on the screen, the stimulus video for the smooth pursuit task being configured for extraction of the distinct set of features for the smooth pursuit task. The stimulus video for the smooth pursuit task may comprise displaying a target in a sequence on the screen following a predetermined continuous path and the target appearing moving at a constant speed towards and from one of four extremes of the screen, prompting the user to deliberately follow the movement of the target on the screen during the smooth pursuit task, the stimulus video for the smooth pursuit task being configured for extraction of the distinct set of features for the smooth pursuit task.

It at least one embodiment, the set of tasks further comprises any combination of the following tasks: a fixation task, a pro-saccade task, an anti-saccade task, an optokinetic nystagmus task, a smooth pursuit task, a spiral task, a visuospatial implicit memory task and a picture free-viewing task. The method may further comprise the visuospatial implicit memory task which may comprise displaying a sequence of original images and a sequence of modified images. Each modified image may correspond to one original image and may be displayed in the same order as the original image, each modified image having at least one object removed therefrom or added therein.

In accordance with at least one embodiment, the method may further comprise detecting movement of the eye by measuring movement of areas of interest on the video of the user's face for each one of the stimulus videos. Detecting movement of the eye may comprise determining an eventuality of user's movement of eyes and a velocity of the movement of the eyes. In accordance with at least one embodiment, detecting movement of the eye may further comprise: determining an area of interest for user's eye and an area of interest for user's face in at least one image (in at least one video frame) of the video of the user's face; measuring an eye movement of at least one eye structure of user's eye; measuring a face (or head) movement of the user's face (or head); generating a relative eye movement of the user's eye relative to the user's head by subtracting the face movement to an overall movement of the eyes; averaging velocity vectors of each tracked area of interest to generate an overall instant velocity vector for the areas of interest. Based on the overall instant velocity vector, the method may further comprise determining an eventuality of the movement of user's eye and a velocity of the movement of the user's eye. In at least one embodiment, detecting the neurological disease is based on the detected movement of the user's eye(s), In at least one embodiment, the values of the set of features for each task are determined based on the detected movement of the user's eye(s).

BRIEF DESCRIPTION OF THE DRAWINGS

Further features and advantages of the present disclosure will become apparent from the following detailed description, taken in combination with the appended drawings, in which:

FIGS. 21A-21E are images illustrating a screen of a tablet or similar computing device displaying targets for performing calibration, according to at least one embodiment;

FIGS. 22A, 22B are images illustrating a screen of a tablet or similar computing device displaying targets for a fixation test, according to one embodiment;

FIGS. 24A-24I are images illustrating a screen of a tablet or similar computing device displaying targets for an anti-saccade task, according to one embodiment;

FIG. 25 is an image illustrating a screen of a tablet or similar computing device displaying a V-shape target for an anti-saccade task, according to one embodiment.

FIG. 33A is a flowchart illustrating a method for identifying eye movements in association to the eye gaze-pattern test and eventually detecting an eye gaze-pattern abnormality related to a neurological disease of a user, according to one embodiment;

FIG. 33B is a flowchart illustrating a method for identifying eye movements in association to the eye gaze-pattern test and eventually detecting an eye gaze-pattern abnormality related to a neurological disease of a user, according to another embodiment;

Figure 1:
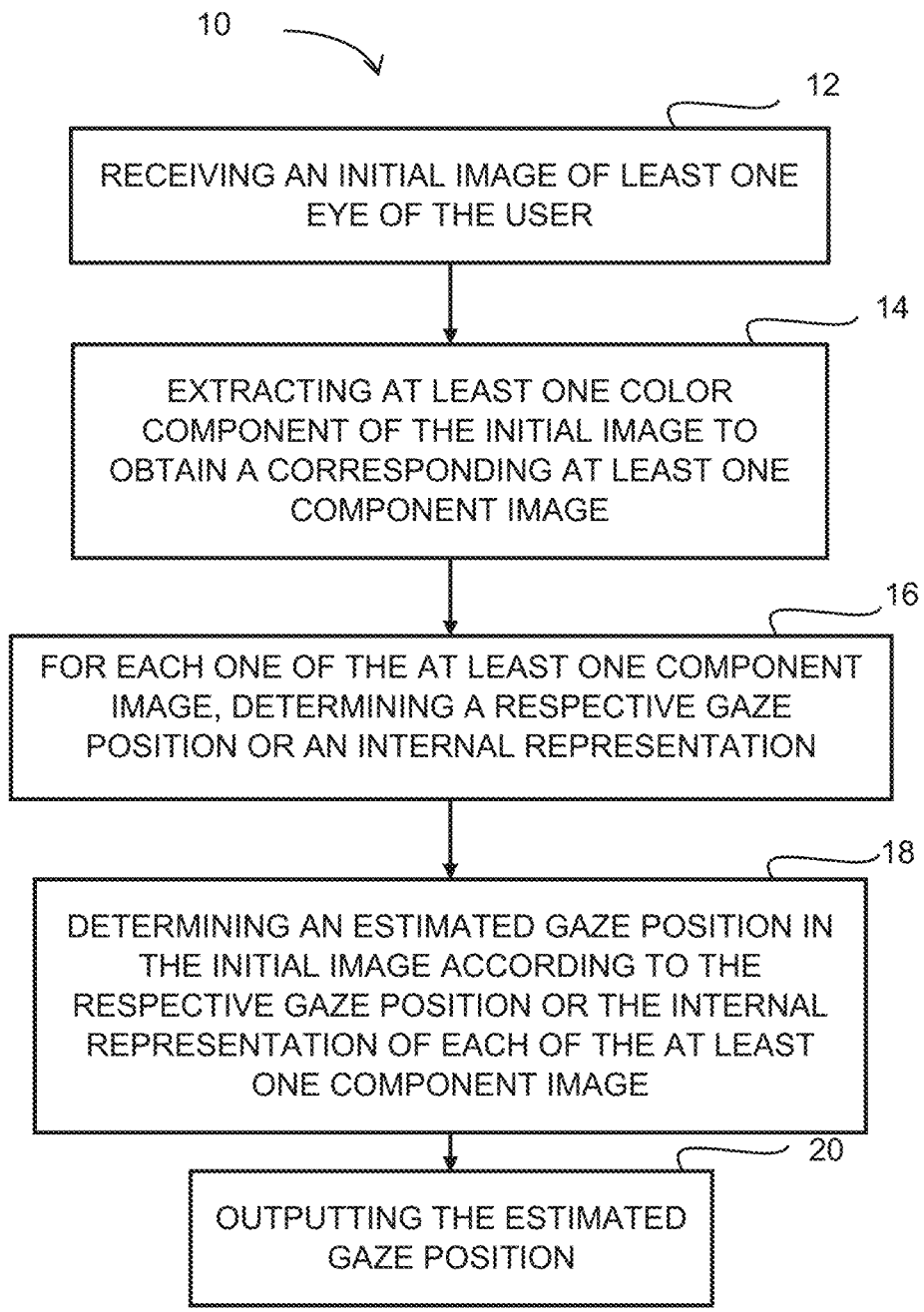
FIG. 1 is a flowchart illustrating a method for determining a gaze position of a user, according to one embodiment.

Further details and advantages will be apparent from the detailed description included below.

DETAILED DESCRIPTION

Referring first to FIG. 33A, there will be described below a method for identifying eye movements in association to the eye gaze-pattern test and detecting eye movement abnormalities related to a neurological disease of a user. The following sections will describe various details for achieving that, including ways to determine gaze position in section 2, while the details of the method for identifying eye movements in association to the eye gaze-pattern test and detecting an eye movement abnormalities related to a neurological disease of a user are described in greater detail in section 3, further below.

To put it briefly, before explaining the method in great detail, FIG. 33A shows the method 250 according to an exemplary embodiment. According to that embodiment, the method comprising the steps of:

Step 251: providing an electronic device comprising a screen for display and a camera in proximity to the screen, where the electronic device may comprise both the screen and the camera built together, wherein the electronic device comprises any one chosen among: a tablet, a smartphone, a laptop computer, a handheld computer; and a tabletop computer comprising the screen having the camera;

Step 252: performing an eye gaze-pattern test by displaying a sequence of targets on the screen while filming with the camera to receive a video of the user's face, the eye gaze-pattern test comprising, for example, detecting eye movements, detecting patterns of eye movements, or both; the eye gaze-pattern test may comprise, for example: fixation task, pro-saccade task, anti-saccade task, and optokinetic nystagmus task;

Optional Step 253: determining an estimated gaze position over time in the video, preferably for each eye, while identifying and removing artifacts in eye movements, such as blinks (described in detail in Section 2 below);

Step 254: extracting features from the video of the user's face, wherein the features are extracted from the angular movement of at least one eye in the video and comprising at least one of: square wave jerk, square wave pulse, ocular flutter, opsoclonus, and an amplitude, a frequency, a velocity or a direction of a nystagmus; and Step 255: detecting an eye gaze-pattern abnormality in the video of the user's face (or in the estimated gaze position overtime), which comprises identifying eye movements in association to the eye gaze-pattern test being performed, such a test comprising at least one of: eye fixation, pro-saccades, anti-saccades, and optokinetic nystagmus, and applying a trained machine learning algorithm on the estimated gaze position overtime in the video to detect the eye gaze-pattern abnormality. Alternatively, the machine learning algorithm may be trained on videos instead of estimated gaze positions. Features may be also extracted from the estimated gaze positions using other algorithms such as expert systems.

FIG. 33B shows a method 260 for detecting an eye gaze-pattern abnormality related to a neurological disease of a user, in accordance with another embodiment. At step 261, an electronic device comprising a screen for display and a camera in proximity to the screen is provided. At step 262, an eye gaze-pattern test is performed for a first time period by displaying a sequence of targets on the screen and simultaneously filming with the camera to generate a video of the user's face during the first time period. At step 263, a first set of features is determined based on the video of the user's face and the sequence of targets displayed on the screen during the first time period. At step 264, the eye gaze-pattern abnormality is detected based on the first set of features determined based on the video of the user's face.

In at least one embodiment, the first set of features may be determined by applying a first trained machine learning algorithm to the video. A second trained machine learning algorithm may be applied to the first set of features to detect the eye gaze-pattern abnormality. The second trained machine learning algorithm is different from the first trained machine learning algorithm as described herein below.

The methods as described herein may be implemented with a camera that operates in a visible spectrum, such as, for example, a video camera integrated with or operatively connected to a laptop, a tablet or a smartphone.

Section 1—Definitions

Machine Learning: A field of computer science that gives computers the ability to learn without being explicitly programmed. To do this, various algorithms will define a method by which a model can be trained, using a set of examples, to classify or predict from new similar examples.

Algorithm: An unambiguous specification of how to solve a class of problems. In machine learning, such an algorithm would provide a general mathematical formulation of a model, as well as a set of steps necessary to assign real values to the variables contained in the general definition of the model.

Model: A model is a complex mathematical construct that describes the relationship between an input and an output. For example, it could describe the relationship between a picture and whether it contains a dog or a cat (classification), or as in this document, between a picture of a person's face and the position of their gaze on a screen. Unless specifically designed otherwise, a model is deterministic. That is, given the same input, it will always produce the same output.

Regression: Regression is a type of problem for which the output is a continuous variable, bounded or otherwise. This is in contrast with classification, where the output of a model can only be one of a finite set of possible outputs.

RGB: RGB a color model in which red, green, and blue light is added together in various ways to reproduce a broad array of colors.

SWJ: SWJ is a square-wave jerk saccade that occurs during fixation. SWJ is defined herein as horizontal saccades that occur during fixation followed between 50 ms and 400 ms by another saccade with an amplitude comparable to the first saccade (<0.75 degree difference) and in the opposite direction.

OSI: Other saccadic intrusions during fixation (all saccades that are not part of SWJ).

SD: standard deviation.

CV: coefficient of variation which is a ratio of the standard deviation to the mean.

BCEA: bivariate contour ellipse area of fixation; encompasses fixation points closest to target for a given proportion (P) of eye positions during one fixation trial. For example, BCEA may be 68% or 95%, which corresponds to one SD around the mean or two SD around the mean.

INO: Internuclear ophthalmoplegia which may be measured multiple ways; the most straightforward is to compute the ratio of the peak velocity of both eyes.

Metrics are extracted from the data on a trial basis (in other words, metrics are extracted from the data collected during each trial).

For the present description, "features" are computed (determined) for learning, classification, prediction, and are obtained by averaging data obtained in several trials, by performing statistics over the metrics applied to ocular motion; in other terms, by determining statistical values of the extracted metrics. The statistical values may comprise, for example, a standard deviation, a coefficient of variation, a maximum value, etc.

Section 2—System and Method for Gaze Tracking

FIG. 1 illustrates a method 10 for determining a gaze position of a user from an initial image, according to one embodiment. As it will be detailed below, in one embodiment, the method 10 is executed by a computer machine provided with at least a processing unit, a memory and a communication unit. The image of the user may be taken using a camera which may be integrated in a mobile and/or portable device such as a smartphone, a tablet, a phablet, a laptop, a computer machine provided with a camera such as a webcam, or the like, or any dedicated device enabling to obtain images of the user. In one embodiment, wherein a calibration procedure has to be performed, a display should be provided to the user, for example the display of the used mobile and/or portable device.

As it will become apparent below, in some embodiments, the method is implemented in using neural networks. Neural networks are machine learning models that employ one or more subsequent layers of non-linear units to predict an output for a received input. Using neural networks conveniently trained enables to greatly improve the accuracy of the determination of the gaze position. The skilled addressee will however appreciate that simpler regression algorithms conveniently implemented may be considered for specific applications, but accuracy of the determination of the position may not be sufficiently satisfactory, as detailed below.

In the following description, the method and associated system for determining the gaze position of a user will first be described in a basic architecture using simple regression algorithms, according to some embodiments. More complex architectures using neural networks will be described later with reference to FIG. 15 to 20.

At step 12 of the method 10, an initial image of at least one eye of the user is received. In one embodiment, the initial image comprises only the eyes of the user. In another embodiment, the received initial image comprises the two eyes of the user. In a further embodiment, the received initial image also comprises other facial features in addition to the eyes of the user, as detailed below. For example, the initial image may comprise eyebrows, ears, a nose, a mouth, etc. In another embodiment, the initial image comprises the whole face of the user.

At step 14, at least one color component is extracted from the initial image to obtain a corresponding at least one component image. In one embodiment, two color components are extracted from the initial image to obtain two corresponding component images. In a further embodiment three color components are extracted from the initial image to obtain three corresponding component images. Indeed, in one embodiment, the initial image of the eye of the user is an RGB (Red-Green-Blue) image provided with a red channel, a green channel and a blue channel. In this exemplary RGB example, a single color channel is selected to build the corresponding component image. More particularly, the decimal code associated with each pixel of the initial image received at step 12 comprises a red value, a green value and a blue value. The red image is generated by taking into account only the red value of the pixels of the initial image, i.e., the red image comprises the same array of pixels as that of the initial image but the green and blue values of the pixels are not taken into account so that only the red value of the decimal code remains associated with each pixel. The red image represents the same image as the initial image but only in red color. Similarly, the green image is generated by taking into account only the green value of the pixels of the initial image, i.e., the green image comprises the same array of pixels as that of the initial image but the red and blue values of the pixels are not taken into account so that only the green value remains associated with each pixel. The blue image is generated by taking into account only the blue value of the pixels of the initial image, i.e., the blue image comprises the same array of pixels as that of the initial image but the green and red values of the pixels are not taken into account so that only the blue value remains associated with each pixel.

As a result, in this example, the output of step 14 consists in the three RBG component images, i.e., the red image of the eye of the user, the green image of the eye and the blue image of the eye.

It should be appreciated that the same extraction or decomposition process could also be applied to other color spaces, such as YCbCr, HSV or HSL for example. However, since the RGB color space is typically the color space in which colors are captured by digital cameras and stored in a computer, the RGB space may be preferred. The use of other color spaces would indeed require an additional processing step to transform the RGB value into the chosen color space. The method is applicable for images collected using color components, such as RGB or other substantially equivalent color components, as described herein. However, the method could be applied under light conditions that would include light components which are not visible, for example using infrared images. Even though the method described herein does not require infrared projectors and cameras, the method can be applied to images comprising a component outside the visible spectrum. It should however be noted that in infrared light conditions, the difference between sclera and iris is very hard to identify as both appear grey in the images, and using infrared is therefore not particularly advantageous.

At step 16, the respective gaze position for each of the at least one component image is determined. It should be understood that any adequate method or algorithm for determining the gaze position may be used, as detailed below. As a result, in the example using the three RGB component images, a first gaze position is determined for the red component image, a second gaze position is determined for the green component image and a third gaze position is determined for the blue component image. In the embodiment in which a single component image is used, a single gaze position will be determined at this step 16. Instead of a respective gaze position, the component image may instead be treated individually by a respective primary stream (such as a respective portion of a larger neural network having convolutional layers) which is used to obtain a respective internal representation. An internal representation is the output, within a neural network, of a given layer of the neural network which is not the output layer.

At step 18, an estimated gaze position in the initial image is determined according to the respective gaze position of each of the at least one component image. In the embodiment in which a single component image is used, the estimated gaze position corresponds to the single respective gaze position determined at step 16.

In the embodiment in which at least two color components are extracted from the initial image, the determined at least two respective gaze positions are combined together using weight factors to obtain the estimated gaze position, using any adequate combination method, as described below. In the example using a RGB image, three respective gaze positions are combined together using weight factors to obtain the estimated gaze position.

The thus-obtained estimated gaze position is then outputted at step 20. For example, the estimated gaze position may be stored in memory for further processing.

It should be understood that the initial image may comprise the representation of a single eye or both eyes. It should also be understood that the initial image may comprise two images, i.e., a first image comprising a representation of a first eye and a second image comprising a representation of a second eye.

In an embodiment in which the initial image comprises at least one additional facial feature in addition to the eyes, the method 10 further comprises a step of cropping the initial image to generate a cropped image having a reduced size with respect to the size of the initial image and comprising a representation of the one or two eyes only (for example, two cropped eye areas, forming a composite image by being joined together, thus effectively removing the upper area of the nose). In order to crop the initial image, the eyes are previously identified within the initial image and extracted. It should be understood that any adequate facial feature recognition method may be used for identifying the eyes within the initial image. For example, this may be done by identifying the outline of the eyes, determining the position of the limbus (i.e., the sclera-iris boundary), and/or the iris and pupil of each eye, within the initial image, as known in the art. It should be understood that any adequate method for identifying eyes within an image may be used.

Once the eyes have been identified within the initial image, the portion of the image that comprises only the eyes is extracted from the initial image to create the cropped image. It should be understood that the size of the cropped image may vary so that the cropped image may comprise more than the eyes for example, while still having a size that is less than that of the initial image.

In one embodiment, the Constrained Local Model (CLM) method is used for identifying the eyes within the initial image. This method uses a number of expert detectors each trained to recognize a specific facial feature such as the inside corner of the right eye or the bridge of the nose. Given the image of a face, each of these experts will produce an estimation of the location of the feature they were trained to detect. Appropriate locations are then connected to produce an outline of the anatomical features of the face. Commonly detected features include: the eyes, the eyebrows, the bridge of the nose, the lips and the jaw. The ears are also sometimes detected. By using the position of different points relative to one another, a three-dimensional model of the face can be constructed.

In one embodiment, the cropping of the initial image for isolating the region of interest, i.e., the eyes, allows improving the signal-to-noise ratio of the data fed to the eye tracking algorithm (feature extraction), as well as decreasing the computational load (dimensionality reduction) and reducing the memory requirements for storing data.

In one embodiment, the extraction of the eyes from the initial image allows greatly reducing the input space to only contain relevant, non-redundant information.

As an example, assuming ideal western male facial proportions, and that the user's face is perfectly inscribed within the frame, the eyes will together represent about 40% of the horizontal space and about 7% of the vertical space of the initial image. This means that the images of both eyes together represent about 2.8% of the pixels of the initial image. The benefits are even greater if the user's face is smaller than the frame of the image. This allows reducing the demands for storage and the computational complexity of the below described regression problem, as further detailed below.

In a further embodiment, at least one additional facial landmark is extracted from the initial image in order to determine the head pose or attitude of the user in this image. In this embodiment, the at least one additional landmark is combined with the respective gaze positions to determine the estimated gaze position. As it will become apparent below, such an embodiment enables to make the method more invariant to head pose.

Head pose is defined as the position of the head relative to the camera. This includes translation and rotation. As measured from an initial image taken from a camera, translation would be measured of the distance between the center of the face and the center of the initial image. Rotation could be expressed in a number of ways, the most intuitive of which, for a human, would be the Euler angles of the head, pitch (head nod), yaw (head shake) and roll (head tilt).

As previously mentioned, modern infrared gaze tracking methods and systems typically make use of a controlled source of light to estimate the rotation of the eyeballs relative to the head, to then produce an estimate of gaze position. Such a system can thus be said to be intrinsically invariant to head pose.

On the contrary, the above described method of FIG. 1 does not make any direct measurement of relative eye rotation, and so cannot be said to be head pose invariant. As previously mentioned, it is expected that the most relevant feature for estimating gaze position is the position of the limbus, or the boundary between the sclera and the iris, and the outline of the eye. This changes when the head is fixed and the position of the gaze changes, but also changes when the gaze is fixed and the position of the head changes, either through translation or through rotation.

Thus, in one embodiment, in order to produce more accurate gaze position estimates, some information about head pose is added to the input data of the method. As all features must be extracted from an image of the user's face, the obvious candidate feature set for this is a set of facial landmarks whose positions relative to each other change as the head moves and rotates. From these features, head translation can be easily determined, for example by taking the distance between a fixed point on the image and a specific facial landmark, or between a fixed point on the image and the centroid of a set of facial landmarks.

The Euler angles of the head are much harder to estimate and require the projections of the 2D coordinates of the facial landmarks onto a 3D model of the user's face. Assuming that the model used is a perfect model of the user's face, the uncertainty on the angles would be the same as the uncertainty on the positions of the facial landmarks. Given that the present method is meant to be deployed for use by the general public, such an assumption cannot be made and a few models of the human face need to be used instead, leading to an added uncertainty on the Euler angles.

In the context of training a machine learning algorithm, an ideal feature set should contain all the information necessary to solve the problem, and only the information necessary to solve the problem. By transforming the coordinates of the facial landmarks into Euler angles, information about the topology of the face model is added to the feature, which is relatively invariant through the dataset, while degrading the quality of the feature by increasing their uncertainty. For these reasons, the coordinates in image space of a set of facial landmarks have been chosen to use as a feature to introduce head pose invariance into our method.

It should be noted that such features already appear naturally in the eye images. Indeed, as the head moves and turns relative to the camera, the apparent height and width of the eyes also change. However, under natural viewing conditions, the angle of the head relative to the camera will hardly ever be greater than 30 degrees, at which point viewing becomes uncomfortable. This means the apparent width and height of the eyes will nearly never vary by more than 15% of their maximum. Given the uncertainty in these measurements, this is unlikely to yield strong head pose invariance.

Figure 2:
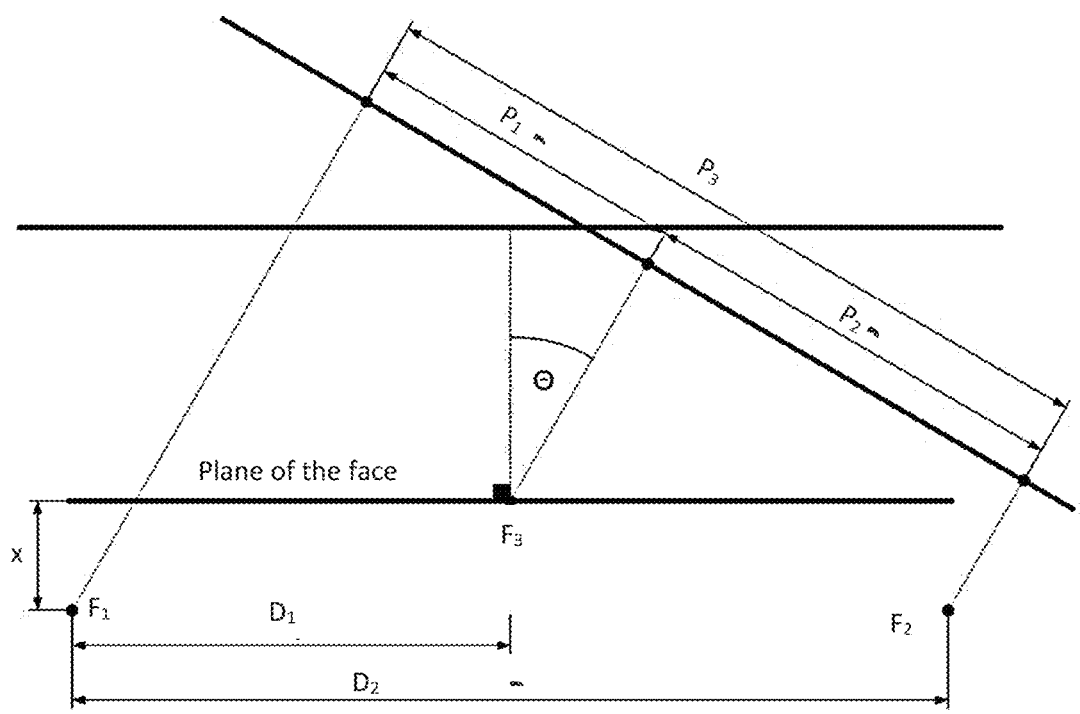
FIG. 2 shows the effects of head rotation on the projections of facial landmarks, according to one embodiment.

To better estimate head pose, in one embodiment, the XY coordinates of certain facial landmarks are used instead, provided that these landmarks do not lie in the same plane in 3D space. This effect is illustrated in FIG. 2. Here, $F_1$, $F_2$ and $F_3$ could represent the positions of the left eye, right eye and nasion, respectively, as seen from the top (the nasion being defined as the most anterior point of the frontonasal suture that joins the nasal part of the frontal bone and the nasal bones, visible on the face as a depressed area directly between the eyes, just superior to the bridge of the nose). Two features could be chosen here: $P_3$, the length of the projection of the distance between the eyes on the viewing surface, or $P_1$-$P_2$, the difference between the lengths of the projections of the distance between the left eye and the nasion, and the right eye and the nasion. The relationships between the values of those features and the angle of the head $\Theta$ is given by equations 1 and 2.

$$P_3 = 2D_1 \cos(\Theta) \quad (1)$$

$$P_1 - P_2 = \quad (2)$$
$$\sqrt{(H^2 + D_1^2)} * (\cos(\Theta - \arctan(HD_1)) - \cos(\Theta + \arctan(HD_1)))$$

One immediate advantage of using $P_1$-$P_2$ over $P_3$ is that the former preserves information about the direction of rotation. Indeed, the value of $P_3$ will always be positive for natural head angles, while $P_1$-$P_2$ will be positive in one direction and negative in the other. Additionally, an important aspect of a good feature is the difference in magnitude between extremes of the features. In other terms, a good feature should maximize the difference between its minimum values and its maximum value. In this example, this will be the case if $D_1$<H, H being the distance between the nasion and the eyes perpendicularly to the plane of the face and $D_1$ being the distance between the nasion and an eye in the plane of the face. In this example, the user's face is considered to be symmetrical, so $D_2$=$2D_1$. As it should now be apparent, a proper choice of facial landmarks can thus ensure these properties, making a choice of features that do not lie in a 2D plane much more interesting for head pose invariance.

Another advantage of using facial landmark coordinates over Euler angles is that the facial landmark coordinates contain information about the distance between the face and the camera, while the Euler angles do not.

Finally, it should be noted that depending on the chosen algorithm and architecture for performing the method, this information is not strictly required for the model to perform well. However, if it is omitted, performance is expected to degrade quickly if the user moves his head away from the typical position it was in during calibration, as it will be detailed thereinafter.

Figure 3:
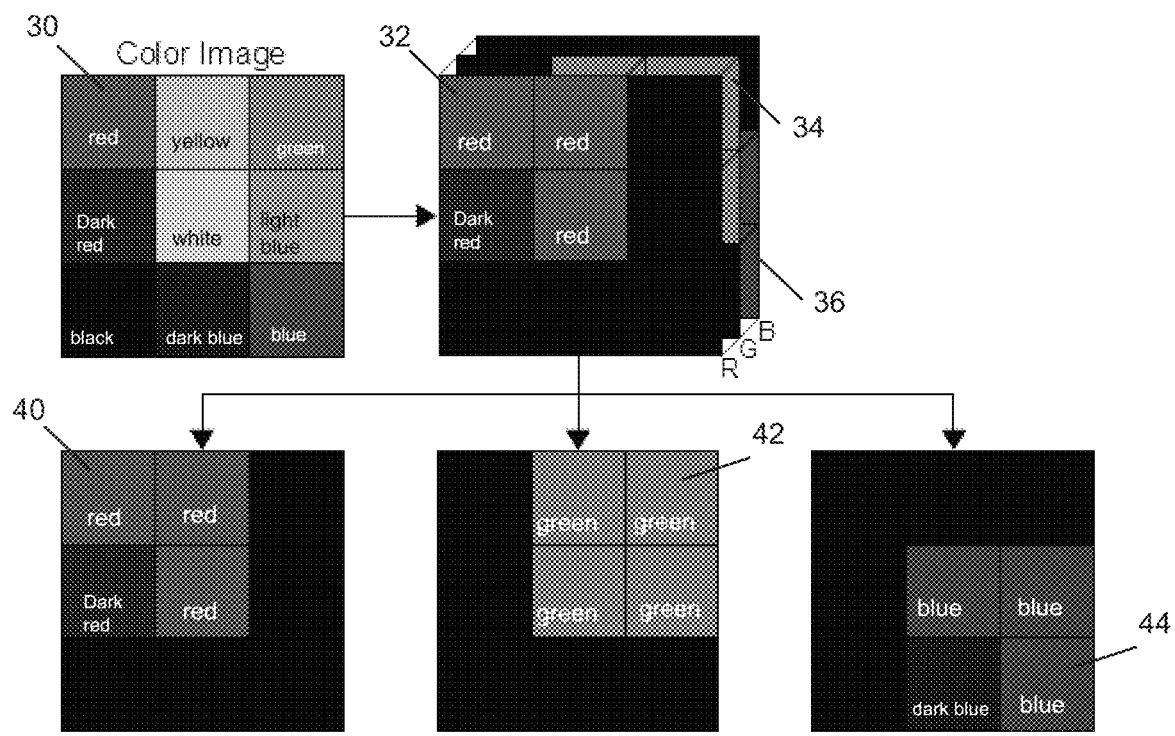
FIG. 3 illustrates a decomposition of an image comprising 9 pixels into three-component RGB images, according to one embodiment.

FIG. 3 illustrates an exemplary decomposition of a color image 30 into its RGB components. It should be understood that the image 30 may be the original initial image or the cropped image as long as it contains the eyes.

The image 30 comprises nine pixels each having a different color. Each pixel has a red value, a green value and a blue value associated thereto, thereby forming the RGB components 32, 34 and 36 of the image 30. The red component 32 comprises only the red value for the nine pixels of the image 30. The green component 34 comprises only the green value for the nine pixels of the image 30. The blue component 36 comprises only the blue value for the nine pixels of the image 30. The RBG components are then isolated to create a red image 40 which includes the nine pixels to which only the red value is associated thereto, a green image 42 which includes the nine pixels to which only the green value is associated thereto, and a blue image 44 which includes the nine pixels to which only the blue value is associated thereto.

It should be understood that each RGB component image corresponds to a greyscale image. Indeed, as the single-color image is a two-dimensional matrix such as a greyscale color image, the new single color image, i.e., the RGB component image, corresponds to a greyscale image, despite representing a color channel. Thus, the greyscaling of the color components is simply a result of the decomposition.

It should be understood that in typical computer vision applications, images are normally fed as M×N×3 tridimensional matrices, comprising 3 layers, each corresponding to one of the RGB components of the image. This matrix would typically be fed to the first layer of the network and treated altogether in bulk (i.e., with the three layers, and using a kernel or filter having the same depth), and the information related to each of the RGB components will be "lost" in the following layers of the network where all data are mixed into the subsequent layers. In such a case, it would not be possible to identify, at an internal representation of the network, information specifically related to one color component only, as everything is already mixed starting at the first layer of the network being applied to the three-dimensional matrix.

Instead, in the present disclosure, the M×N×3 matrix is split in three different two-dimensional matrices of M×N size (or M×N×1), and each one is treated individually by its own portion of neural network (i.e., their own distinct primary stream) before being fused after a few layers of their own distinct primary stream. For example, each of the three M×N×1 matrices is fed to its own individual and distinct primary stream (portion of the neural network), which would comprise more than one layer. For example, these individual and distinct primary streams for each of the color component images could comprise 2 or 3 convolutional layers and 2 or 3 fully-connected layers, before fusion. This ensures that information that can be found in a single color-component image is well analyzed individually. The individual and distinct output of the respective primary stream for each color component image should not be confused with the whole network's output (which can be trained), and it is rather called an internal representation of the network at that layer (to be fused in a step called feature fusion for further processing downstream).

Figure 4:
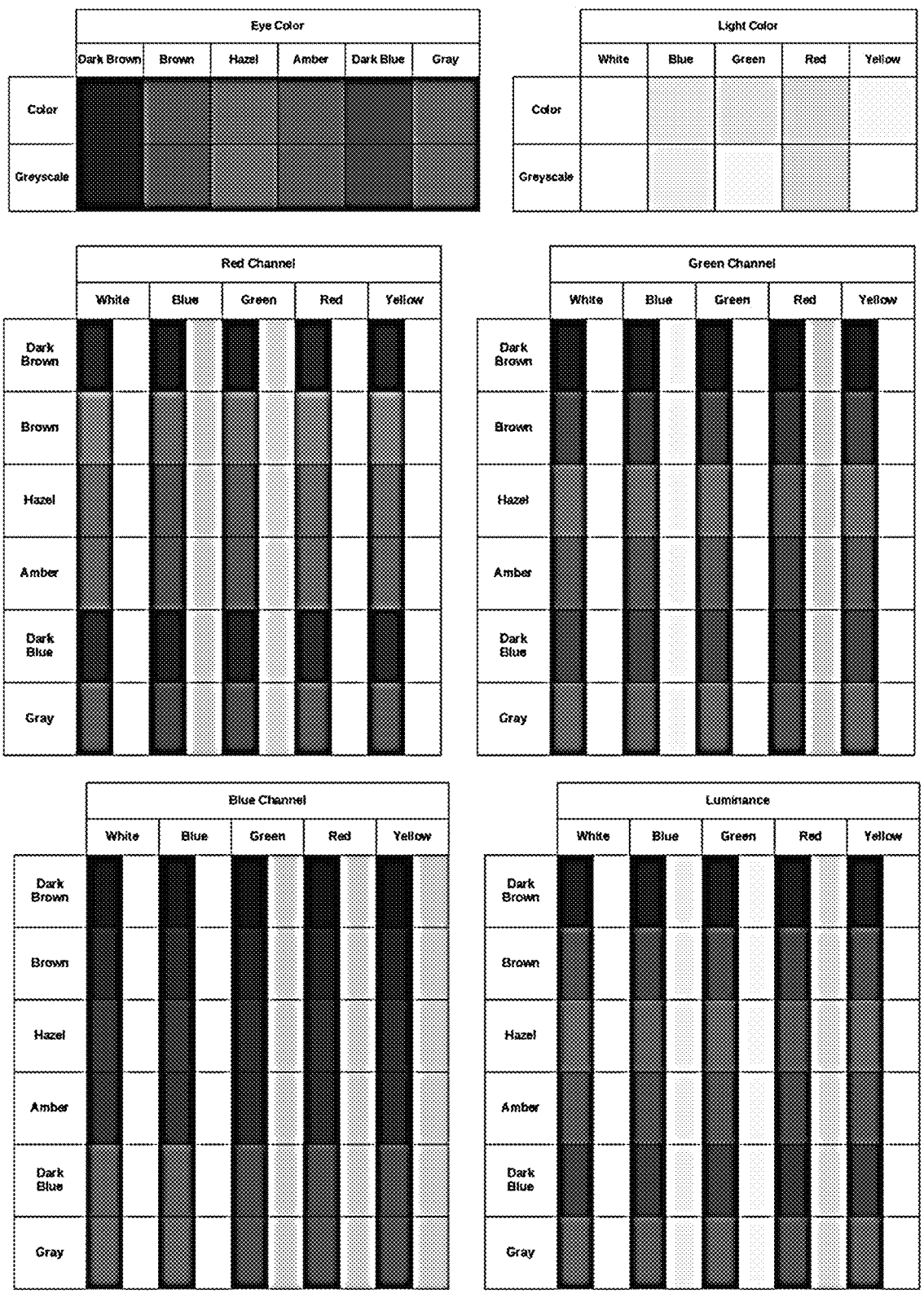
FIG. 4 shows an example of contrast between eye colors and sclera in individual color channels of an RGB image, and between their grayscale equivalents, according to one embodiment.

Making sure that the individual color component images are treated according to their own, distinct primary stream has its advantages. Indeed, we have found empirically that depending on the circumstance, one of the color components (for example, in a RGB color space, one of R, G or B) can be more appropriate or useful than the others. This can improve accuracy, as described below. After applying in parallel the distinct primary streams, all resulting internal representations from the three color component images (or more generally, from the at least one color component image), are fused with the illumination information and facial landmarks (or an internal representation thereof following an auxiliary stream). The conditions in which one of the color component images is more appropriate empirically depend on the illumination information in the environment. There is no single color component which is more adapted than another in every circumstance. Therefore, the neural networks adapt to the illumination context by performing a fusion between each color-component image (at the end of their own individual and distinct primary stream) and with the illumination information (which can also undergo an auxiliary stream). By doing this, the neural network automatically adapts to the real illumination context and uses the most useful color component in this particular circumstance by performing additional operations through subsequent layers of the network, i.e., the internal stream, which is the portion of the neural network downstream of the fusion layer. In one embodiment, the most relevant feature for eye tracking in ambient light may be the position of the sclera-iris boundary, or limbus, relative to the outline of the eye. Thus, a better contrast between the sclera and the iris would allow for a better definition of this boundary and thus a more robust eye tracking method or algorithm. Different eye colors reflect different amounts of red, green and blue light. For this reason, one can expect that the identification of the limbus may depend on the user's eye color and the ambient lighting conditions, and for the reasons described above, the neural network is trained to identify and use an internal representation originating from a specific color component image (or a plurality thereof), for which the edges between sclera and iris, and between sclera and outline of the eye are more easily identified under specific illuminant values, to be fed into the systems and combined with the internal representation of the component images at the fusion layer. By decomposing the image into its RGB components, at least one of the resulting images may have a better contrast between the sclera and the iris. Thus, depending on the user's eye color and the temperature of the ambient light, one of the three RGB component images should provide the best contrast of the limbus. Moreover, we hypothesize that one of the color channels will always have higher contrast than in the equivalent greyscale image. This is illustrated in FIG. 4, in which the contrasts between different eye colors under various lighting conditions, for each of the RGB color channels and for the equivalent grayscale values, are illustrated. It is worth mentioning that, for each eye color and lighting combination, the greatest contrast between all the color channels is always greater than in the grayscale case.

The task of selecting which channel to prioritize is not a trivial one, as there exists infinite combinations of ambient lighting conditions and eye color. In one embodiment, a regression algorithm is used. While the color images could have been converted to grayscale, or the color channels concatenated to each other to be processed in the same pipeline, this would not have allowed the leveraging of these differences between color channels. For this reason, the three color channels are processed separately, and then fused at the decision or feature level, eventually using additional previously computed data such as illuminant values, as described below.

While it is considered that having separate streams to process each color channels separately is beneficial to the performance of the model/algorithm, it is not necessary to include all three color channels. Indeed, considering that the fusion of the single-channel streams is done through a weighted sum of each stream, which, while being an oversimplification in the case of deep-learning models, is not inaccurate, the omission of one or more color channels would amount to setting the weights applied to these channels in the weighted sum to zero. A model that only uses two channels or a single channel, or indeed a grayscale rendition of the color image, can be seen as a special case in which one or two processing streams are essentially ignored.

In one embodiment, as previously mentioned, the determination of the respective gaze position for the three component images is performed using a regression algorithm/method. For example, linear regression, ordinary least squares, decision tree regression and/or artificial neural networks may be used.

In a further embodiment, the determination of the estimated gaze position is also performed using a regression method or algorithm. For example, linear regression, ordinary least squares, decision tree regression and/or artificial neural networks may be used.

Regression algorithms usually follow a same training procedure. For the purpose of the present description, the inputs are named X, the estimates are named Ŷ and the targets are named Y. In the present case, X would be the initial image of the user's eyes, Ŷ would be the estimate of the position of the user's gaze produced by the regression method, and Y would be the actual position of the user's gaze.

The training procedure creates a model F(X) that approximates a mathematical relationship between X and Y, and that yields Ŷ from X. In other words, Y≈Ŷ=F(X). The goal of the training procedure is to adjust this mathematical relationship in a way to minimize the error between Y and Ŷ for any given X.

In the case of linear regression, F(X) may be expressed as:

$$F(X) = B + \sum Wj * Xj \qquad (3)$$

where Xj is the jth feature of the input vector X, Wj is the weight associated to that feature, and B is the Y-intercept, or bias, of the linear regression model. In this case, the goal of the training procedure would be to adjust the weights and the bias so as to minimize the prediction error.

In one embodiment, regression algorithms also have hyperparameters, which affect the training procedure and therefore the final model, which also have to be optimized. In the present example of linear regression, the hyperparameter would tell whether or not to include a bias term in the equation.

Hyperparameter optimization involves splitting the dataset into two parts, the training set and the validation set. Prior to training, a hyperparameter search space is defined, which bounds the possible values of hyperparameters to be explored. For each set of values, the training procedure described above is completed, and the performance of the trained model is obtained from the validation set. The set of hyperparameter values that yielded that best performance will finally be retained as the final model.

As described at step 18 of the method 10, the respective gaze positions determined for the three RGB component images are combined together to provide an estimated gaze position. It should be understood that different combination methods may be used.

In one embodiment, the estimated gaze position corresponds to a weighted average of the respective gaze positions determined for the three RGB component images:

$$\hat{Y}f = \sum W_c * \hat{Y}_c \qquad (4)$$

where Wc is the weight factor associated with each RBG component c.

In one embodiment, the weight factors are determined using a measure of how much each color channel contributes to the color image.

For example, the weight factors may be determined by calculating the relative contribution of each color channel by summing the values of every pixel of a color channel, and dividing the result by the sum of all the pixels in the image. In one embodiment, such a method for calculating the weight factors is simple, fast to compute and fairly invariant to light intensity. Indeed, lowering or increasing the intensity of ambient lighting would lower or increase the value of every pixel in every channel by a same factor, up to the point a pixel starts saturating. In one embodiment, the three values representing the relative contribution of each color channel correspond to the weight factors Wc.

In another embodiment, a further regression algorithm may be used for combining the three respective gaze positions obtained for the three RGB component images. The inputs of the further regression algorithm could be the three values representing the relative contribution of each color channel and the three gaze positions obtained for the three RGB component images, which would through training approximate the relationship between ambient light and color channel contribution.

As previously mentioned, in an improved gaze position estimation, the combination of the three respective gaze positions obtained for the three RGB component images could further been done as a function of the illuminant values representative of the relative contribution of each color channel of the initial image.

In one embodiment, the illuminant values may be determining using the method proposed in Yang, K. F., Gao, S. B., & Li, Y. J. (2015); Efficient illuminant estimation for color constancy using grey pixels; In *Proceedings of the IEEE Conference on Computer Vision and Pattern Recognition* (pp. 2254-2263), but other methods may be used. For example, it may be considered to calculate the relative contribution of each color channel by summing the values of every pixel of a color channel, and dividing the result by the sum of all the pixels in the image, as previously explained.

Other methods such as Gamut Constrained Illuminant Estimation and Grey Pixel Illuminant-Invariant Measure may also be used, as it should be apparent to the skilled addressee.

Once the illuminant values have been determined, they are combined with the respective gaze positions to determine an estimation of the gaze position in the initial image.

Figure 5:
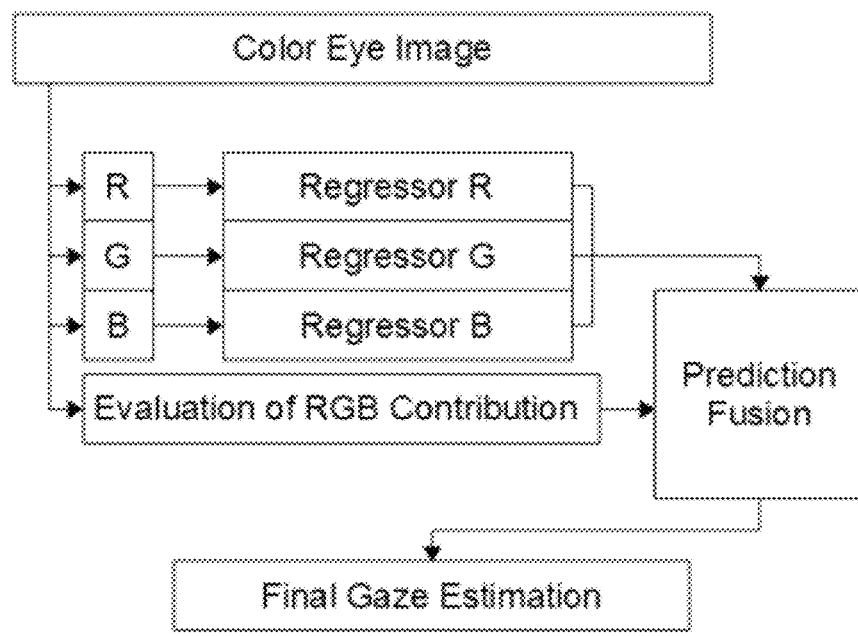
FIG. 5 is a schematic block diagram illustrating a regression algorithm used for implementing the method shown in FIG. 1, according to one embodiment.

FIG. 5 shows a regression algorithm used for implementing the method 10 shown in FIG. 1, according to one embodiment. Three regressors are trained as single channel regressors, each on a different color channel of the full color image of the user's eye. Their decisions are then combined by a fourth regressor, also called prediction fusion, taking as an input the predictions from all three channels and the relative contribution of each color channel to the image.

In this embodiment, four regression algorithms were tested as single-channel regressors, that were deemed appropriate considering the following parameters: small size of the initial dataset, low memory requirements and relatively low training time. These algorithms were: Ridge Regression, a Support Vector Machine (SVM), an Extremely Randomized Trees (ETR) and ElasticNet.

The image database used for training is collected from volunteers who were asked to look at 13 predefined crosses on a computer screen. Each cross appeared one after the other and stayed in view for three seconds. Subjects were given the first second to find the target. During the next two seconds, ten images of the subject's face and surroundings were captured using a camera, to obtain images similar to those obtained from a mobile device's front facing camera. Then, the target disappeared, and the next target appeared. Ten images were captured for every cross to provide usable data in the event of a blink.

To build the dataset used for training, the images containing the subject's right and left eyes were cropped from the initial image using a facial feature recognition algorithm to determine the location of the eyes and eyebrows in the initial image. This information was used to define the bounding boxes for each eye, which were then used to crop the eyes. These two eye images were then associated with an (X,Y) set of coordinates representing the location of the center of the cross on the screen at the time of image acquisition.

Figure 6:
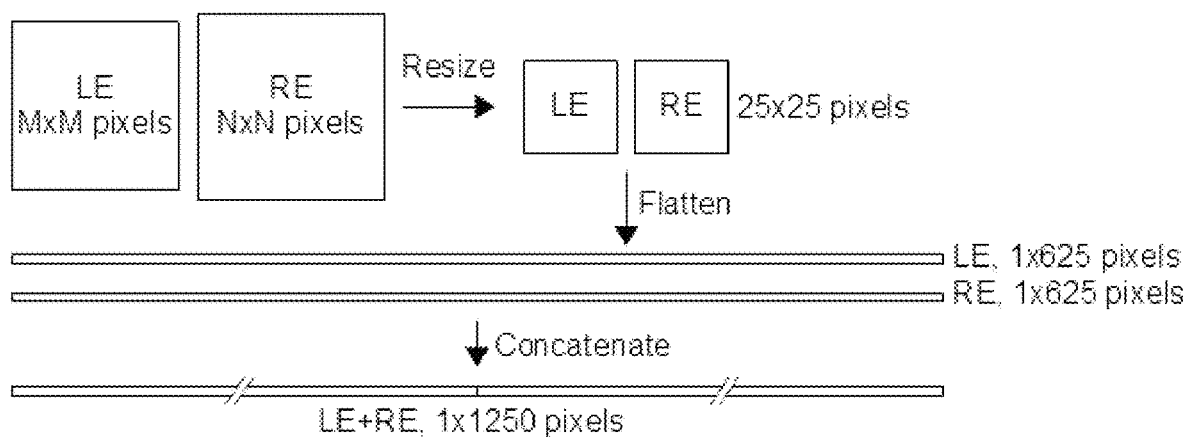
FIG. 6 illustrates the resizing, flattening and concatenation of two images, in accordance with an embodiment.

Referring now to FIG. 6, as the algorithms used in this embodiment only accept one-dimensional matrices (i.e., vectors) of a fixed size as inputs, the eye images need to be resized and flattened before they could be used. The resizing was necessary because there was no guarantee that the cropped eye images would be the same size from frame to frame, or even as each other. Square crops were used to simplify the process, and both images were resized to be 25×25 pixels. This size was chosen empirically, as a compromise between an acceptable loss of resolution and an increased size. The images are then flattened to make them one pixel high, while preserving the total number of pixels. Finally, the images are concatenated to produce a single image with double the number of pixels Finally, the images are concatenated to produce a single image with double the number of pixels. This image is the input to a single-color regressor.

Figure 7:
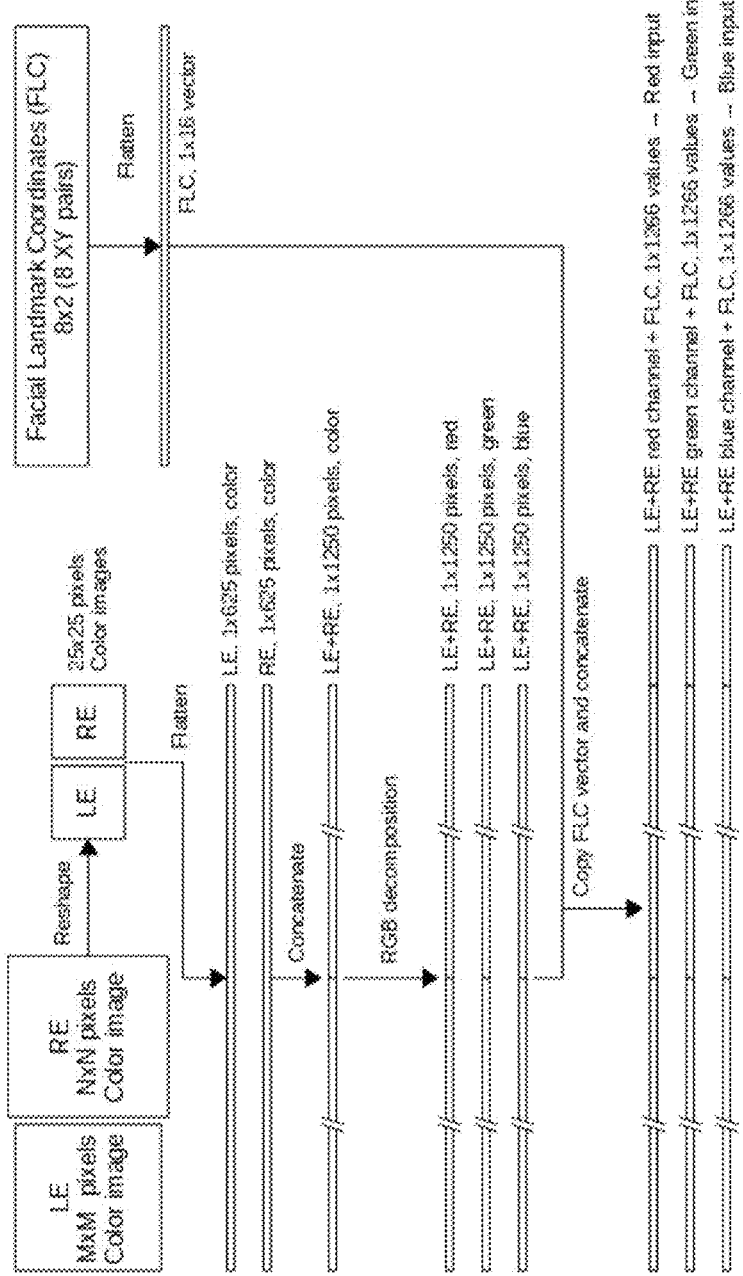
FIG. 7 illustrates the resizing, flattening and concatenation of two images, in accordance with another embodiment.

While the reshaped, concatenated and flattened eye images would be sufficient to train an eye tracking system, the system would be very sensitive to head movements. To obviate this issue, a vector of (X,Y) facial landmark coordinates may also be concatenated to the eye vectors to form the inputs to the algorithms, according to one embodiment and as illustrated in FIG. 7. In one embodiment, the XY coordinates of eight facial landmarks are retrieved using a third-party facial landmark detection algorithm. These coordinates are flattened into a vector of 16 values. After the processing steps described in FIG. 6, the eye vectors are separated into individual color channels. Each of these vectors is then concatenated with a copy of the facial landmark vector. The resulting three vectors are finally used as the inputs to the single-channel regression algorithms.

Before training, a search space of possible hyperparameter values was defined for every algorithm under consideration. Models were then trained and tested for each channel, for each algorithm and for each set of relevant hyperparameters. The performance metrics used to evaluate the performance of a model were the Mean Absolute Error (MAE) and the coefficient of determination R2.

The MAE is the average distance between an estimate and the target value. In this case, as the estimates and targets were sets of two-dimensional coordinates, the Euclidean distance was the distance metric.

The R2 is an indicator of how well future values are likely to be predicted by the model. Values typically range from 0 to 1. A value of 1 represents a model with perfect predictive power, that will yield the target value for any possible input value. A value of 0 represents a constant model that always outputs the same value, regardless of the input value. As a model can be arbitrarily bad, values can range into the negatives.

For each color channel, the model that had achieved the highest R2 was kept as the final model. The hyperparameters used to train this model were saved for future use.

In one embodiment, the architecture that was settled on for the single-channel regressors was a combination of a Ridge Regressor and an SVM, whose outputs were averaged. Testing shown that these two algorithms made complimentary mistakes of the same magnitude. That is, if one overestimated the gaze position by a certain amount, the other underestimated the gaze position by substantially the same amount. By averaging their predictions, their mistakes were averaged, thus making the model more accurate.

For prediction fusion, i.e., the determination of the estimated gaze position based on the respective gaze positions, all the aforementioned regression algorithms were tested in addition to linear regression. Linear regression was added as a candidate due to the very low dimensionality of the input space for this regressor. Indeed, the input was comprised of the two-dimensional outputs of all three single-color regressors, as well as the relative contribution of all three color channels, for a total of 9 dimensions.

Following the same approach as the single-color regressors for model exploration and hyperparameter optimization, the linear regression algorithm was settled to perform color correction, as there was no significant gain from using a more complex regression algorithm. Thus, the method used for combination was the above-described method described in Equation 5, where G is the final gaze estimate, $W_c$ are weights, $I_c$ is the illuminant value for a specific color channel, and $G_c$ is the gaze estimate for a specific color channel.

$$G = B + \sum_{c \in [R,G,B]} W_c * I_c + \sum_{c \in [R,G,B]} W_c * G_c \quad (5)$$

The means by which the weight factors $W_c$ were determined was by computing the relative contribution of each color channel, that is the sum of the intensity of each pixel for a given channel divided by the sum of the intensity of each pixel for each channel, as previously described.

These initial algorithms, although very quick to train, are not capable of incremental learning, which severely limits the size of the dataset the models is trained on, and so its ability to generalize. Tests have shown that the application required constant calibrations and the knowledge gained by calibrating with one user could not feasibly be extended to a large set of users. For these reasons, machine learning algorithms capable of incremental learning may be preferred for a given application, specifically Artificial Neural Networks, as Convolutional Neural Networks seemed particularly well-suited to this problem, as described in details below with reference to FIGS. 15 to 20.

In one embodiment, the above-described method 10 may be embodied as a computer program product comprising a computer readable memory storing computer executable instructions thereon that when executed by a computer perform the steps of the method 10.

In one embodiment, the above-described method 10 may be embodied as a system comprising a communication unit for at least one of receiving and transmitting data, a memory and at least one processing unit configured for executing the steps of the method 10.

Figure 8:
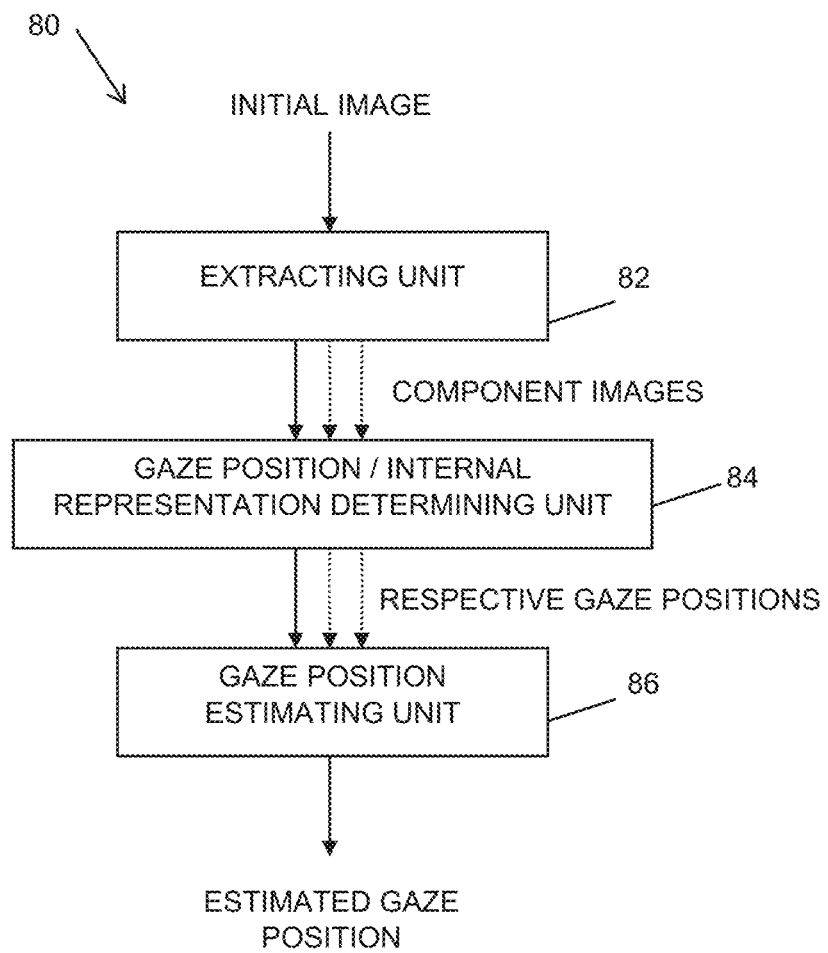
FIG. 8 is a schematic block diagram illustrating a system for determining a gaze position, in accordance with one embodiment.

Referring now to FIG. 8, a system 80 for determining a gaze position of a user in an initial image will now be described, according to one embodiment. The system 80 is provided with an extracting unit 82, a gaze position determining unit 84 and a gaze position estimating unit 86.

The extracting unit 82 is configured for receiving an initial image of at least one eye of the user and extracting at least one color component of the initial image to obtain a corresponding at least one component image, as detailed above. In one embodiment, the extracting unit 82 is configured for extracting at least two distinct color components of the initial image to obtain at least two corresponding component images. In a further embodiment, the extracting unit 82 unit is configured for extracting three distinct color components of the initial image to obtain three corresponding component images. In one embodiment, the extracting unit 82 is configured for extracting each of three RGB components of the initial image, as previously described. In a further embodiment, the extracting unit 82 may be further configured for cropping the initial image, as described above.

The gaze position determining unit 84 is configured for receiving each of the component images from the extracting unit 82 and determining a respective gaze position for each one of the component images, as described above.

The gaze position estimating unit 86 is configured for determining an estimated gaze position in the initial image according to the respective gaze position of each of the at least one component image and outputting the estimated gaze position. In the case where two or three component images are extracted, the gaze position estimating unit 86 is configured for combining each of the respective gaze positions together, for example using weight factors, as previously detailed.

In one embodiment, the received initial image contains additional features other than the at least one eye, and the extracting unit 82 is further configured for identifying the at least one eye within the received initial image; extracting a portion of the initial image containing only the at least one eye to obtain a cropped image; and extracting the at least one color component of the cropped image to obtain the corresponding at least one component image, as previously described.

In an embodiment wherein illuminant values are used, the extracting unit 82 is further configured for, for each of the component images, determining an illuminant value representative of the relative contribution of the corresponding component image to the initial image, as previously described. In this case, the gaze position estimating unit 86 is further configured for combining the illuminant values with the respective gaze positions.

In an embodiment wherein head pose invariance is implemented, the received initial image further contains at least one facial landmark, as detailed above. The extracting unit 82 is further configured for extracting the at least one facial landmark to obtain a corresponding at least one landmark position. In this embodiment, the gaze position estimating unit 86 is further configured for combining the at least one landmark position with the respective gaze positions.

In one embodiment, each one of the units 82, 84 and 86 is provided with a respective processing unit such as a microprocessor, a respective memory and respective communication means. In another embodiment, at least two of the units 82, 84 and 86 may share a same processing unit, a same memory and/or same communication means. For example, the system 80 may comprise a single processing unit used by each unit 82, 84 and 86, a single memory and a single communication unit.

Figure 9:
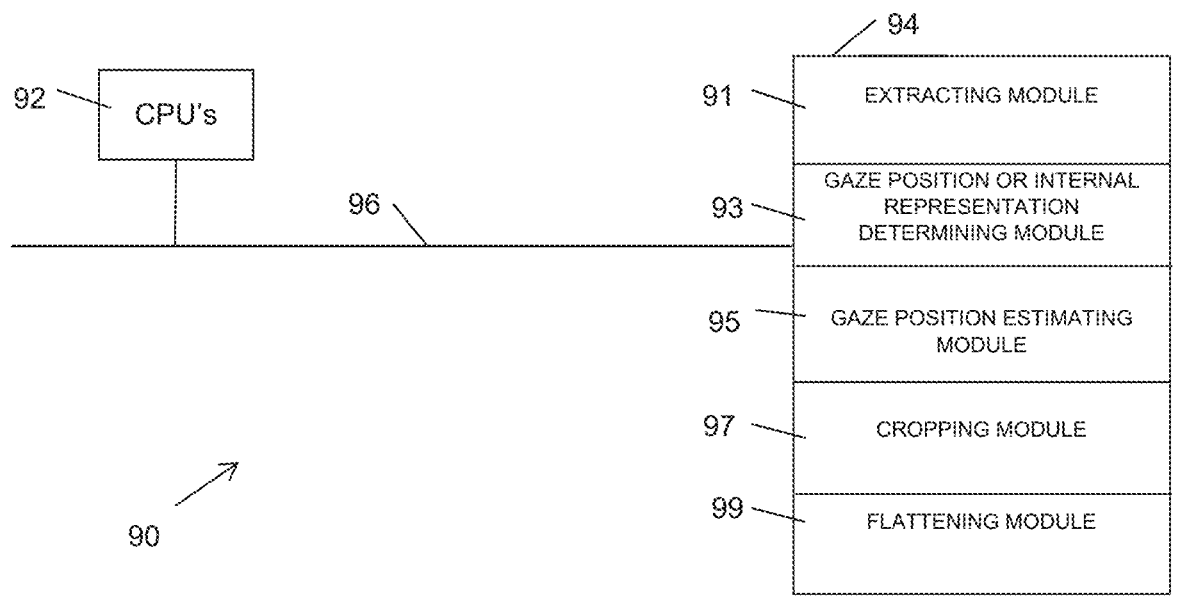
FIG. 9 is a block diagram illustrating a processing module adapted to execute at least some of the steps of the method of FIG. 1, in accordance with one embodiment.

FIG. 9 is a block diagram illustrating an exemplary processing module 90 for executing the steps 12 to 20 of the method 10, in accordance with some embodiments. The processing module 90 typically includes one or more Computer Processing Units (CPUs) and/or Graphic Processing Units (GPUs) 92 for executing modules or programs and/or instructions stored in memory 94 and thereby performing processing operations, memory 94, and one or more communication buses 96 for interconnecting these components. The communication buses 96 optionally include circuitry (sometimes called a chipset) that interconnects and controls communications between system components. The memory 94 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 94 optionally includes one or more storage devices remotely located from the CPU(s) 92. The memory 94, or alternately the non-volatile memory device(s) within the memory 94, comprises a non-transitory computer readable storage medium. In some embodiments, the memory 94, or the computer readable storage medium of the memory 94 stores the following programs, modules, and data structures, or a subset thereof:

An extraction module 91 for extracting at least one color component of the initial image to obtain a corresponding at least one component image;
  a gaze position determining module 93 for determining the gaze position in the component images;
  a gaze position estimating module 95 for determining an estimated gaze position in the initial image according to the respective gaze position of each of the at least one component image;
  a cropping module 97 for cropping images; and
  a flattening module 99 for flattening images.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, the memory 94 may store a subset of the modules and data structures identified above. Furthermore, the memory 94 may store additional modules and data structures not described above.

Although it shows a processing module 90, FIG. 9 is intended more as a functional description of the various features which may be present in a management module than a structural schematic of the embodiments described herein. In practice, and as recognized by those of ordinary skill in the art, items shown separately could be combined and some items could be separated.

The following description will now describe the use of deep learning algorithms or models that may be used to improve the estimation of the gaze position in the initial image, as previously mentioned. The method using deep learning has similarities with the method described above; however, one notable difference is that the result of the first "primary" treatment of the distinct color component images is an "internal representation", which is generally not the same as a respective gaze output. The internal representation has already been mentioned above and is the output of a layer inside the neural network, to be fused with other internal representations. Normally, it has no concrete meaning as it is not a final network output which results from training and is not designed to be an estimation of any sort (it is merely the output of that layer).

However, the method not involving neural networks that was described above outputs the respective gaze output in an intermediate step, and this the respective gaze output such as the respective outputs of the Regressor R, G or B in FIG. 5, can be viewed as a specific case of the "internal representation" in which the internal representation happens to have a meaning, i.e., the respective gaze output, as it is the result from training and is designed to be an intermediate estimate.

Figure 10:
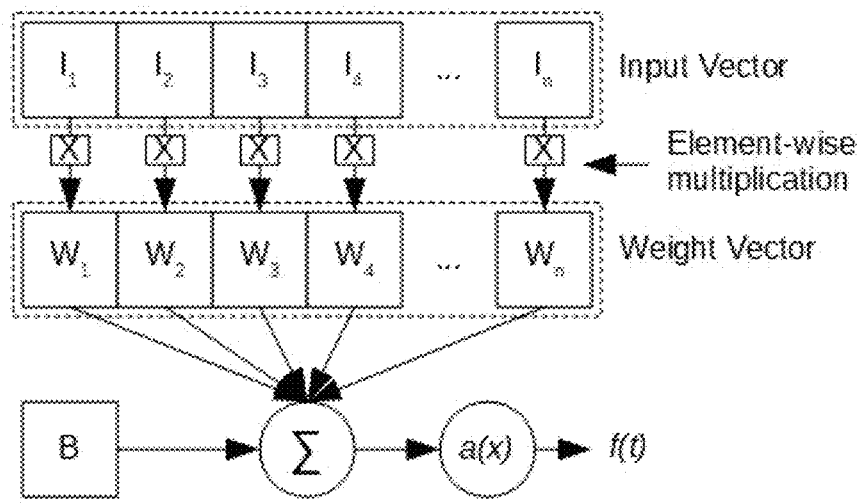
FIG. 10 illustrates the structure of an artificial neuron of a neural network.

Referring now to FIG. 10, there is shown the typical structure of an artificial neuron, the fundamental unit of Artificial Neural Networks, which can be arranged in several connected layers of neurons. The artificial neuron represents a mathematical operation applied to a weighted sum to produce an output. The artificial neuron has four main components. The neuron's input is a vector $I_N$ of numbers of size N. The neuron's weights are also a vector $W_N$ of size N, multiplying element-wise the input vector. The neuron can have a bias term B. Finally, the neuron has an activation function f(x) which determines its output, or activation a(t). The output of a neuron can thus be expressed as $a(t)=ft(B+\Sigma Ii \cdot Wi)$.

Figure 11:
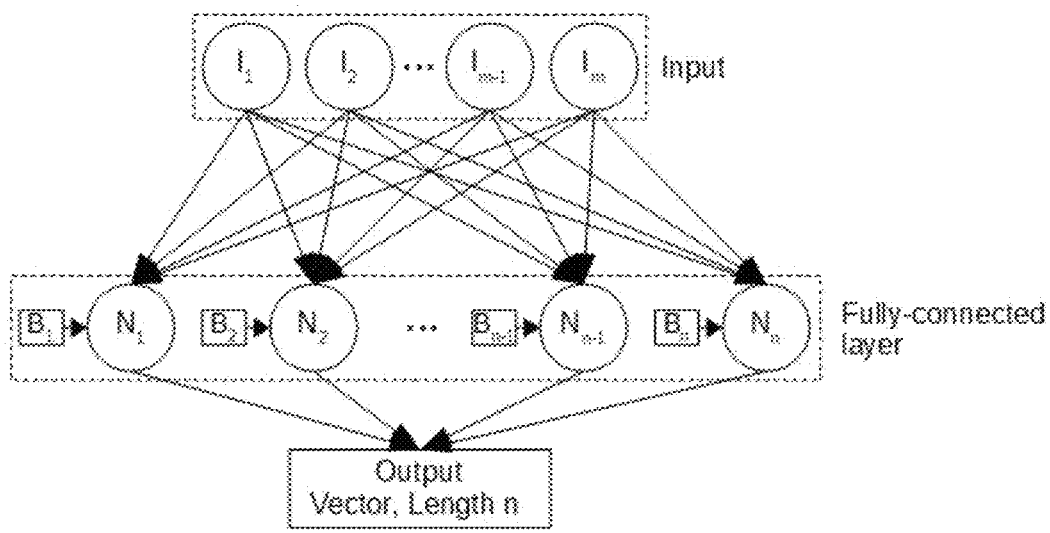
FIG. 11 illustrates the structure of a fully-connected layer of a neural network, according to one embodiment.

FIG. 11 illustrates the structure of a fully-connected layer of neurons, which is a layer of neurons whose neurons have as an input all the outputs of the previous layer. That is, each neuron of the layer accepts as an input vector the entire output vector of the previous layer. Given a fully connected layer of size N and an input vector I of size M, each neuron will have M inputs and so M weights, and so the layer has an M×N weight matrix W and a bias vector B of size N. To simplify computations, all the neurons are made to have the same activation function. The output of the layer is thus a vector given by the application of the activation function to each element of the vector obtained by the matrix operation I·W+B.

Figure 12:
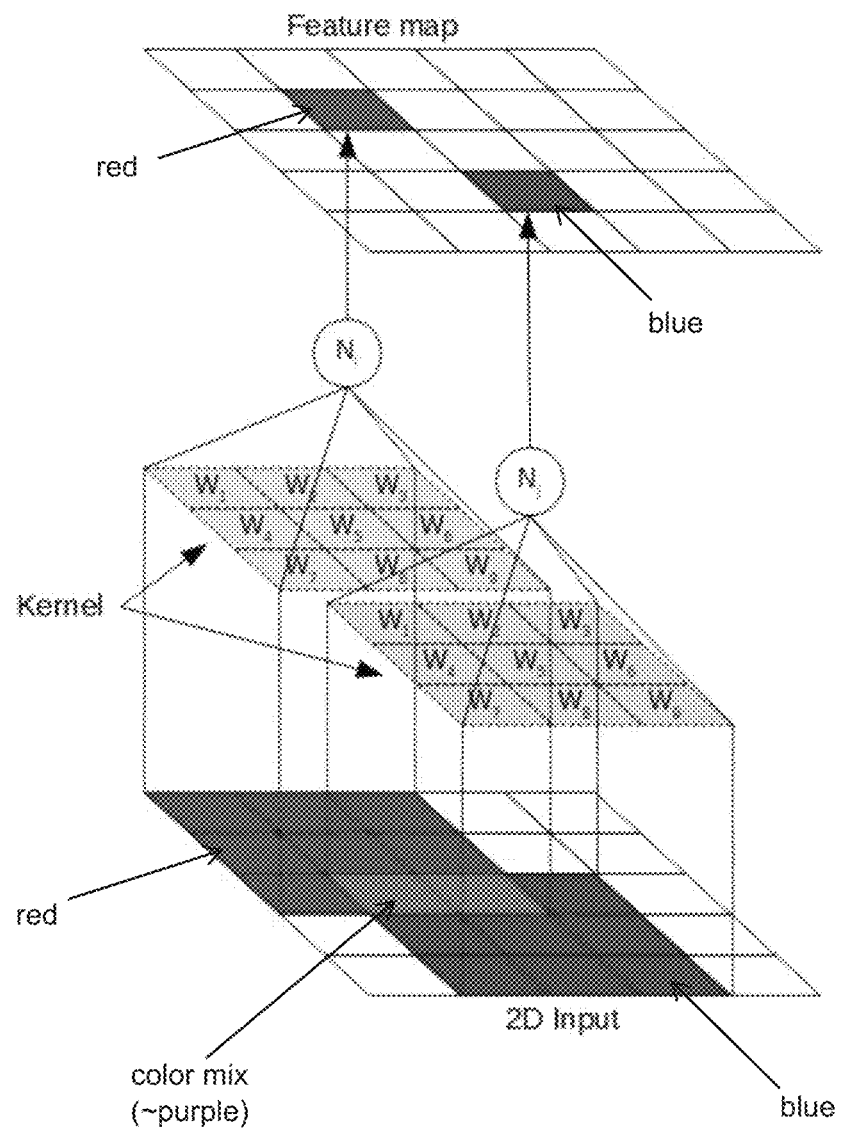
FIG. 12 illustrates the structure of a convolutional layer of a neural network, according to one embodiment.

FIG. 12 illustrates a structure of a convolutional layer of neurons, which is a layer that takes as an input a multi-dimensional matrix instead of a single-dimension vector. The layer is defined by its convolutional kernels instead of being defined by the number of neurons it contains, as a fully-connected layer would be. These layers were initially designed to be used on greyscale images, but their working principle can be extended to a higher dimensional input. For simplicity, we will refer to an element of the input as a pixel, but it needs only be an element of a matrix that may not be an image.

The workings of a convolutional layer are described here and illustrated in FIG. 12. For a given input of size H*W, a convolutional layer is said to have H*W neurons, each associated with a pixel. The layer is also given a set of M*N convolutional kernels, which are essentially a set of weights.

However, unlike the fully-connected layer in which each neuron has its own set of weights, in a convolutional layer, all neurons share the same weight. Each neuron will have a receptive field on the input, of the same size as the convolutional kernels, with the neuron centered in the receptive field. In FIG. 12 for example, we use a single 3*3 kernel. The receptive fields of neurons $N_i$ and $N_j$ are shown.

The output of the layer is a set of feature maps, one for each kernel, of the same size as the input. Each pixel of a feature map is given by the application of the activation function to the sum of the pixel values multiplied by the appropriate weight of a kernel. The result of this operation is the same as convolving the kernel over the input, so filtering the input with the kernel, and applying the activation function to the result, hence the name "convolutional".

Figure 13:
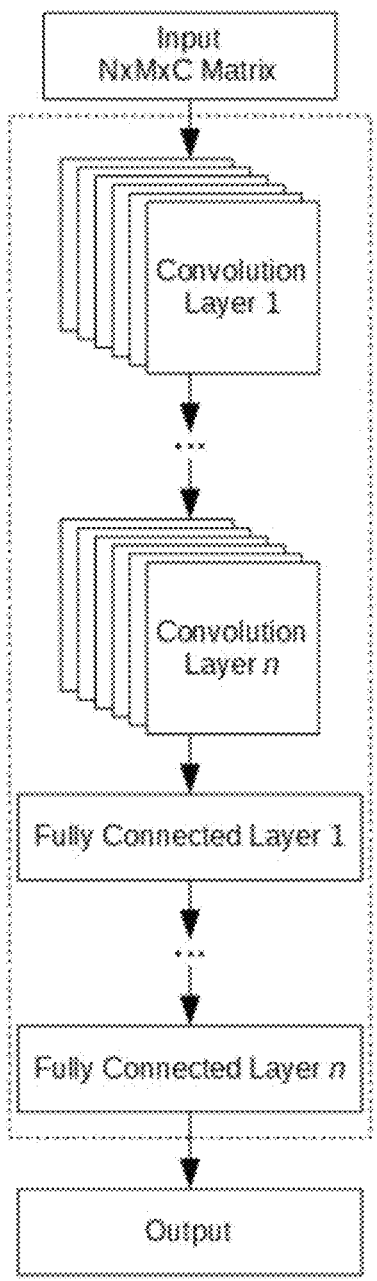
FIG. 13 illustrates the structure of a convolutional stream, according to one embodiment.

FIG. 13 illustrates a structure of a convolutional stream of a neural network using fully-connected layers of neurons that can be used to implement the method, according to one embodiment.

Primary convolutional streams are processing streams of neural network layers that can be used to process the individual color channels of the eye images. As they are convolutional, at least one convolutional layer is included in each stream but a plurality of streams is used in one embodiment. After a certain number of convolutional layers, a number of fully-connected layers may be added downstream, although not required. In fact, it is common practice to add fully-connected layers to a set of convolutional layers as this tends to improve the predictive power of the model. For example, and without limitation, the primary stream of a given color component image can include two or three convolutional layers, and two or three fully-connected layers, before arriving at the fusion layer downstream, which receives the internal representation from the respective primary stream for this given color component image. Batch normalization method can be used on the convolutional layers, while L2 regularization and Dropout regularization method can be used on the fully-connected layers. Other regularization methods or combinations thereof can also be applied to these convolutional layers. It has however been empirically determined that the above mentioned methods are well suited for the application. Additionally, max pooling can be used after each convolutional layer in order to reduce the dimensionality of the input to the next layer. Again, pooling is a widely used tool but is not required. Other pooling methods may also be used, such as average pooling. A pooling operation reduces a neighborhood of pixels to a single value by performing some operation on the neighborhood, such as averaging the values or taking the maximum value.

If the convolutional stream does not use fully-connected layers, the output of a convolutional stream is a set of feature maps, the number of which corresponds to the number of kernels in the last convolution layer. If one or more fully-connected layers are used, the output of a convolutional stream will be a vector containing the same number of elements as the number of neurons in the last fully-connected layer. Additionally, if one or more fully-connected layers are used, the output of the last convolutional layer must be flattened into a vector to be accepted as an input by the first fully-connected layer, as previously described with reference to FIGS. 6 and 7.

Figure 14:
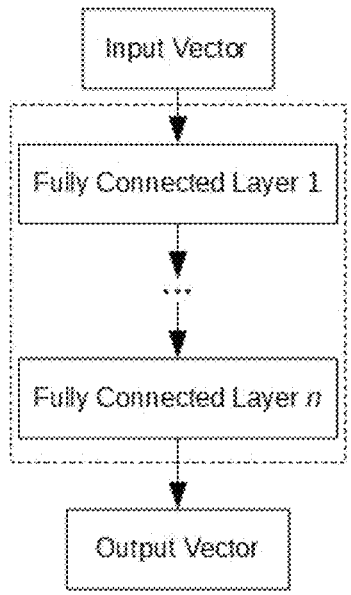
FIG. 14 illustrates the structure of a fully-connected stream, according to one embodiment.

FIG. 14 illustrates a structure of a fully-connected stream of a neural network that can be used to implement the method, according to another embodiment.

Primary fully-connected streams are streams of neural network layer that can be used to process the individual channels of the eye images. As they are composed exclusively of fully-connected layers, the eye images need to be flattened into vector form to be accepted as inputs by the first fully-connected layer of the stream, as previously detailed with reference to FIGS. 6 and 7. If no fully connected-layer is used, the output of such a stream is the vectorized input image. Such a case may be rare but may be useful in the case where the output of the stream is inputted into another stream for further processing. If one or more fully-connected layer is used, the output is a vector containing the same number of elements as the number of neurons in the last fully-connected layer.

In one embodiment, L2 regularization and Dropout regularization methods are used on the fully-connected layers but other regularization methods or combinations thereof can also be applied to these fully-connected layers.

In the case where auxiliary inputs are used, namely the illuminant values and the facial landmark coordinates for example, they can be fed directly to the fusion layer, or alternatively and advantageously, auxiliary input streams of neural network can be used to apply some processing to the auxiliary inputs. The fusion layer will then receive the internal representation originating from these auxiliary inputs (illuminant values and the facial landmark coordinates). Since these inputs are of low dimensionality, being of size 3 and 16 respectively in the previously described example, the layers used in these streams are fully-connected layers in one embodiment. If one or more fully-connected layers are used, the output of an auxiliary stream will be a vector containing as many elements as there are neurons in the last fully-connected layer. If no fully-connected layer is used, the output of an auxiliary stream is its input. In one embodiment, L2 regularization and Dropout regularization method or algorithm can be used on the fully-connected layers, although other methods may be considered. The structure of an auxiliary input stream is similar to the one of a primary fully-connected stream illustrated in FIG. 14.

As it will become more apparent below, a fusion layer is used to fuse the outputs of the upstream layers (i.e., respective internal representation from the plurality of distinct primary streams and auxiliary streams) into a single vector. This is required since at least one fully-connected layer is used to produce the output of the system, and as discussed above, a fully-connected layer accepts one and only one vector. This means that one or more fusion layers may be needed to fuse the outputs of the convolutional and auxiliary streams into a single vector to be used as the input to the output layer.

The inputs to this layer are the outputs of at least two upstream streams. If no fully-connected layers are used in a convolutional stream, the output of this stream needs to be flattened into a vector prior to a fusion operation, as previously described.

The fusion operation itself consists in concatenating the input vectors into a single vector whose length is equal to the sum of the length of all the input vectors. Fusion at this level is said to be feature fusion, as opposed to the prediction fusion used in the embodiment shown in FIG. 5. Feature fusion in a neural network can also be referred to as the fusion of internal representations.

An internal stream of neural layers is an optional set of fully-connected layers that can be used to apply further processing to the output of a fusion layer. The input of the stream is thus the output of a fusion layer. If one or more fully-connected layers are used, the output of the stream is a vector containing the same number of elements as there are in the last fully-connected layer. If no fully-connected layers are used, the output of this stream is its input, so the output of the fusion layer. The output of an internal stream can itself be used as an input to a fusion layer. L2 regularization and Dropout regularization method or algorithm can be used on the fully-connected layers, although other methods may be considered.

It should be noted that while fully-connected layers can exclusively be used in this type of stream, it is also possible to use 1 D convolutional layers instead, given the potentially relatively high dimensionality of some inputs. Convolutional layers however appear to be inappropriate, mostly because this type of layer is meant to exploit relationships between neighboring values, or within a neighborhood of values. The structure of an internal stream is similar to the one of a primary fully-connected stream illustrated in FIG. 14.

As it will become more apparent below, in one embodiment, the output of the system is provided by a fully-connected layer of size one or two, depending on whether the system is to produce both X and Y gaze coordinates, or only one of these, as further described in more details below. In this embodiment, the input to this layer is either the output of an internal stream or the output of a fusion layer.

A great many activation functions are commonly used in Artificial Neural Networks, and any function can be used so long as it is differentiable. Such functions include but are not limited to: the identity function, the logistic function (such as the sigmoid function), the tanh function and the rectified linear unit (ReLU) function.

In one embodiment, the ReLU function is used for all layers except for the output layer, which used the identity function. Such embodiment has shown good results, but other functions may be used to yield models with different performance metrics.

Referring now to FIGS. 15 to 20, a method and a system for determining a gaze position of a user that rely on neural network architectures, according to some embodiments, will now be generally described in more details.

As it will become apparent below, in one embodiment of the method 10, the steps of determining a respective gaze position, or internal representation for neural networks as it is presently the case, and determining an estimated gaze position are performed in combination. Indeed, the at least one component image is processed using a neural network. The neural network is implemented by one or more computers and has one or more neural network layers. The neural network is configured to, at run time and after the neural network has been trained, process the at least one component image using the one or more neural network layers to generate the estimated gaze position. Training of the neural network will be described below.

This method is implemented using the system 80 previously described wherein the system is provided with a neural network. In this embodiment, the neural network is configured to, at run time and after the neural network has been trained, process the at least one component image using the one or more neural network layers to generate the estimated gaze position. In one embodiment, the system 80 has at least one primary stream forming a first portion of the neural network, each corresponding to a color component of the acquired images, each primary stream, each being configured to generate the respective internal representation to be fused with the others, and in some cases, to be also fused with the internal representation from auxiliary inputs such as illuminant values and facial landmark coordinates. In other words, in the case the three component images of a RGB image are used, the system 80 has three distinct primary streams, as it will become apparent below upon description of FIGS. 15 and 16. The system 80 also has a second portion of the neural network, i.e., the internal stream, configured to generate the estimated gaze position. As it should be apparent, the outputs of the first portion of the neural network (i.e., at least one primary stream from the at least one color component image, and the auxiliary streams, if any) are used as the inputs of the second portion of the neural network. Various architectures for the first neural networks may be used. It may comprise one or more fully-connected layers only and/or one or more convolutional layers. If convolutional layers are used, a fully-connected layer is provided downstream the last convolutional layer, as detailed below. The second portion of the neural network has at least one fusion layer, each having at least one fully-connected layer. This second portion of the neural network, or internal stream, starts from at least one of the at least one fusion layer. The second neural network may also comprise an output layer downstream the one or more fusion layer. The output layer may comprise one or more fully-connected layer.

Two general types of architectures will now be described with reference to FIGS. 15 and 16, in accordance with some embodiments. The architectures are only described generally since the specifics of the layers of the neural networks fall within the domain of hyperparameter optimization and many combinations of number of layer and layers parameters can be explored for a given architecture.

Figure 15:
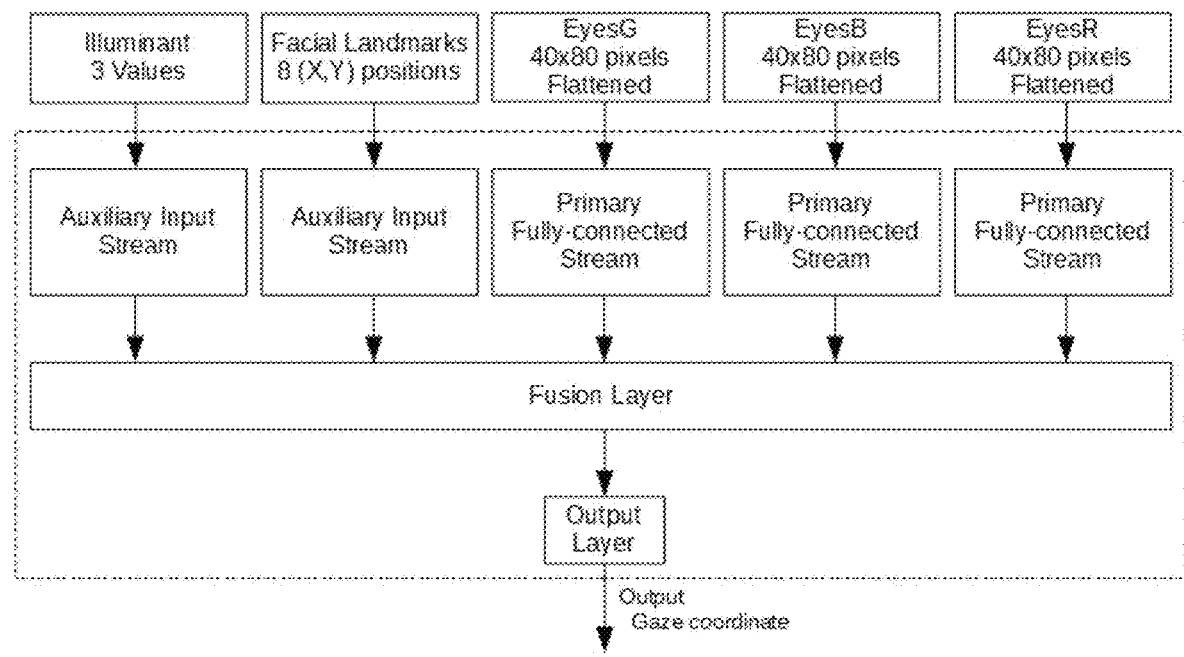
FIG. 15 is a schematic block diagram illustrating an architecture using a multi-layer perceptron for implementing the method of FIG. 1, according to one embodiment.

Referring now to FIG. 15, an embodiment of the system using a multi-layer perceptron will be described. This architecture contained five fully-connected streams of neural layers, one for each input. Three of the streams act as three distinct neural networks for the three color channels of the eye images, outputting a respective internal representation (not a network output) at the last layer thereof. The two remaining streams are auxiliary input streams, one for the illuminant values and one for the facial landmark coordinates. The outputs of these five streams are fused into a single vector with a fusion layer to be used as the input to an output layer. In this example, the fusion layer is comprised in the second neural network previously described.

As mentioned previously, a multi-layer perceptron is used to get an estimate of an appropriate model size, to provide a starting point to do hyperparameter optimization. In one embodiment, MLPs is chosen because they are much easier than ConvNets to condition properly, that is to choose a set of hyperparameters that produce a viable model. While the models trained under this architecture produced some viable results, MLPs are much less powerful than ConvNets on image processing problems. For this reason, ConvNets will be used in subsequent embodiments described below.

The architecture shown in FIG. 15 only contained input streams of neural layers and a fusion layer. There was no internal stream between the fusion layer and the output layer. Additionally, the eye images used were of size 40×80 pixels. The same size was used in early convolutional architectures, before it was increased to 80×160 pixels in an effort to improve results.

Figure 16:
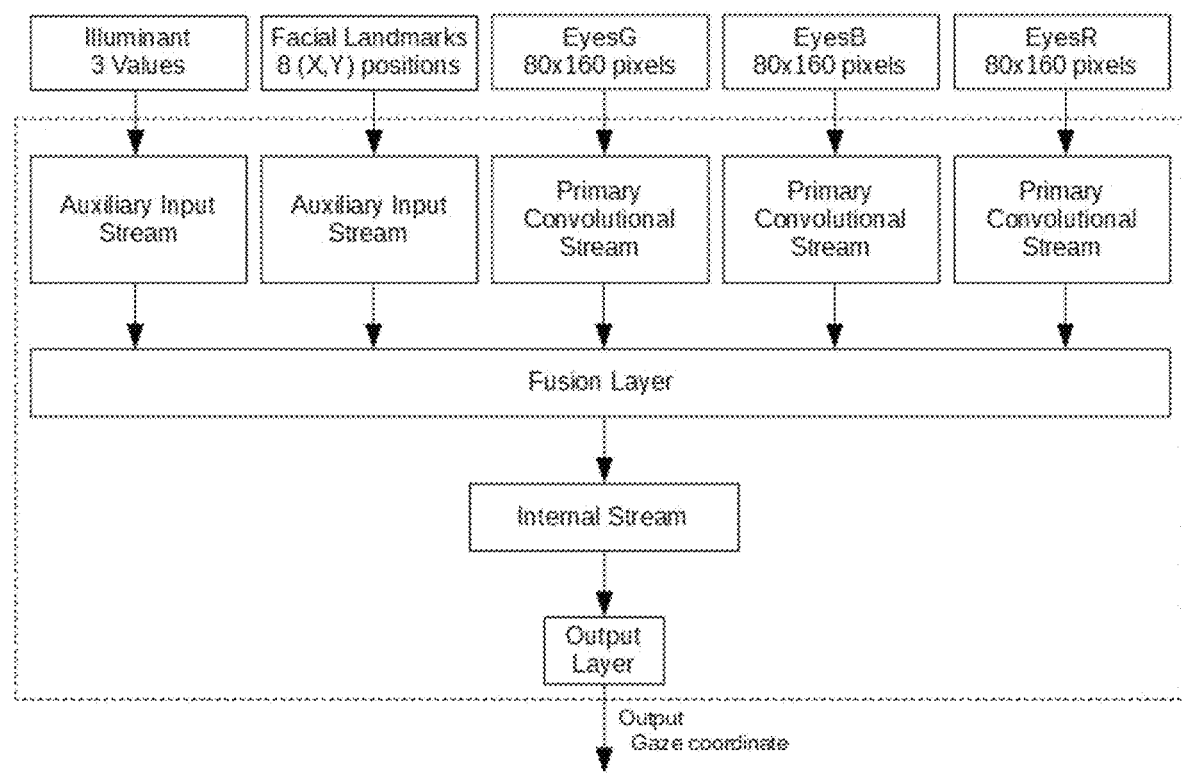
FIG. 16 is a schematic block diagram illustrating an architecture using a convolutional neural network for implementing the method of FIG. 1, according to another embodiment.

FIG. 16 shows an embodiment of the system using convolutional neural networks. Indeed, the architecture that appears to provide the best results uses three convolutional streams as the respective three first neural network streams, one for each of the color channels of the eye images, as well as two auxiliary input streams, one for the illuminant values and one for the facial landmark coordinates. A single fusion layer is used to fuse these five streams. The fusion layer is then fed into an internal stream, and the architecture is capped by the output layer which produces the gaze estimate.

Some attempts to fuse the convolutional streams and the auxiliary streams at different depths in the architecture were made, but they did not yield better results. In these architectures, and according to one embodiment, the convolutional streams would be fused in one fusion layer and the auxiliary streams would be fused in another. Internal streams would then be used to process the outputs of these two fusion layers. Another fusion layer would then fuse the outputs of these internal streams. The output of this fusion layer would be fed to a third internal stream, which would finally output to the output layer.

In order to implement such architectures, a training of the neural network has to be done. The used database was composed of 2.5 million face images, belonging to about 1500 people. The database was split into a training set, a validation set and a test set using a 70-20-10% split. These images were obtained from volunteers tasked to look at a series of stimuli on the screen of a mobile device of different screen sizes, be it a smartphone (such as an iPhone) or a tablet (such as an iPad). For each captured image, some metadata was captured which included: the device type, the screen size, the position of the stimulus in screen coordinates, the position of the stimulus in centimeters from the camera, the orientation of the device (one of portrait, portrait Upside Down, landscape Right, landscape Left), as detailed below.

In accordance with one exemplary embodiment, and without limitation, model training was performed on servers in the cloud, for instance an Amazon EC2 p3.8xlarge instance, using Keras and Tensorflow as machine learning function libraries. Model regularization included batch normalization on the convolutional layers, and L2 and Dropout on the fully-connected layers. The weight of the L2 regularization was 0.01 for all models. The Dropout rate was 25% for all models. These values were found empirically and may not represent the best possible values. The chosen architectures of the various models are given in Tables 1 to 3 below. For all convolutional layers, max pooling with size 2×2 was used. To simplify hyperparameter optimization, the same architecture is used for all convolutional streams, and the same architecture is used for both auxiliary streams.

Table 1 below shows the sizes of the convolutional layers. The layer sizes are given in the order that they are traversed by the data, so from input to output. For a convolution layer, X M×N kernels means that X number of kernels were used in this layer, with each kernel being of size M×N. Table 2 shows the number of layers in the auxiliary streams, and size of each layer. Table 3 shows the number of layers in the internal stream, and size of each layer.

TABLE 1

| Model | # Convolution Layers | Convolution Layer Sizes | # Fully-connected Layers | Fully-connected Layer Sizes |
|---|---|---|---|---|
| Portrait, horizontal | 3 | 16 11 × 11 kernels<br>8 5 × 5 kernels<br>4 3 × 3 kernels | 2 | 200 neurons<br>100 neurons |
| Portrait, vertical | 3 | 16 11 × 11 kernels<br>8 5 × 5 kernels<br>4 3 × 3 kernels | 3 | 200 neurons<br>100 neurons<br>50 neurons |
| Portrait Upside-Down, horizontal | 3 | 16 11 × 11 kernels<br>8 5 × 5 kernels<br>4 3 × 3 kernels | 2 | 200 neurons<br>100 neurons |
| Portrait Upside-Down, vertical | 3 | 16 11 × 11 kernels<br>8 5 × 5 kernels<br>4 3 × 3 kernels | 3 | 200 neurons<br>100 neurons<br>50 neurons |
| Landscape Right, horizontal | 3 | 16 11 × 11 kernels<br>8 5 × 5 kernels<br>4 3 × 3 kernels | 2 | 200 neurons<br>100 neurons |
| Landscape Right, vertical | 3 | 16 11 × 11 kernels<br>8 5 × 5 kernels<br>4 3 × 3 kernels | 3 | 200 neurons<br>100 neurons<br>50 neurons |
| Landscape Left, horizontal | 3 | 16 11 × 11 kernels<br>8 5 × 5 kernels<br>4 3 × 3 kernels | 2 | 200 neurons<br>100 neurons |
| Landscape Left, vertical | 3 | 16 11 × 11 kernels<br>8 5 × 5 kernels<br>4 3 × 3 kernels | 3 | 200 neurons<br>100 neurons<br>50 neurons |

TABLE 2

| Model | # Fully-connected Layers | Fully-connected Layer Sizes |
|---|---|---|
| Portrait, horizontal | 1 | 32 neurons |
| Portrait, vertical | 1 | 32 neurons |
| Portrait Upside-Down, horizontal | 1 | 32 neurons |
| Portrait Upside-Down, vertical | 1 | 32 neurons |
| Landscape Right, horizontal | 1 | 32 neurons |
| Landscape Right, vertical | 1 | 32 neurons |
| Landscape Left, horizontal | 1 | 32 neurons |
| Landscape Left, vertical | 1 | 32 neurons |

TABLE 3

| Model | # Fully-connected Layers | Fully-connected Layer Sizes |
|---|---|---|
| Portrait, horizontal | 3 | 182 neurons<br>91 neurons<br>45 neurons |
| Portrait, vertical | 2 | 107 neurons<br>53 neurons |
| Portrait Upside-Down, horizontal | 3 | 182 neurons<br>91 neurons<br>45 neurons |
| Portrait Upside-Down, vertical | 2 | 107 neurons<br>53 neurons |
| Landscape Right, horizontal | 3 | 182 neurons<br>91 neurons<br>45 neurons |
| Landscape Right, vertical | 2 | 107 neurons<br>53 neurons |
| Landscape Left, horizontal | 3 | 182 neurons<br>91 neurons<br>45 neurons |
| Landscape Left, vertical | 2 | 107 neurons<br>53 neurons |

In the event that the algorithms previously described does not produce sufficiently accurate gaze estimates for a given application, a calibration procedure can be used during which a small dataset is collected from the specific user to adjust the general model's predictions.

For performing the calibration procedure, an additional set of pictures would need to be captured. For each of these captured pictures, some stimulus would be displayed on screen, whose position (the target) would be recorded and at which the user would need to look when the picture is taken.

This would constitute the minimal database for the calibration procedure. This database could contain other metadata, such as device type, screen size, screen resolution and device orientation.

Figure 17:
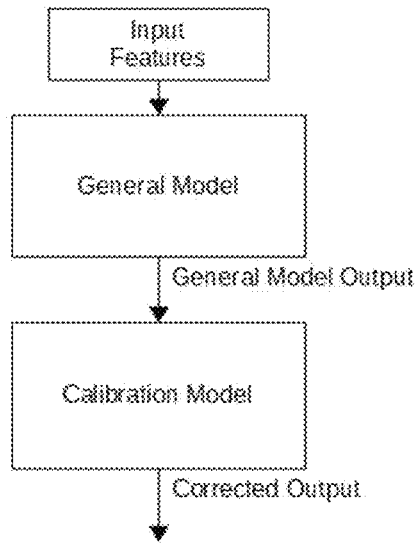
FIG. 17 is a schematic block diagram illustrating the method of FIG. 1, wherein a calibration model is used, according to one embodiment.

From there, for each captured image, the same features used by the general model would be extracted from the pictures and would be fed to the general model for processing. Here, two options are available to train the calibration model. One option, would be to capture the output of the general model for each image. These gaze estimates would constitute the inputs of the calibration model, while the true position of the stimulus at the time of image capture would be the target. Once trained, such a model would be appended to the output of the general model, taking it as an input and producing a new gaze coordinate. Such a model is shown in FIG. 17.

Figure 18:
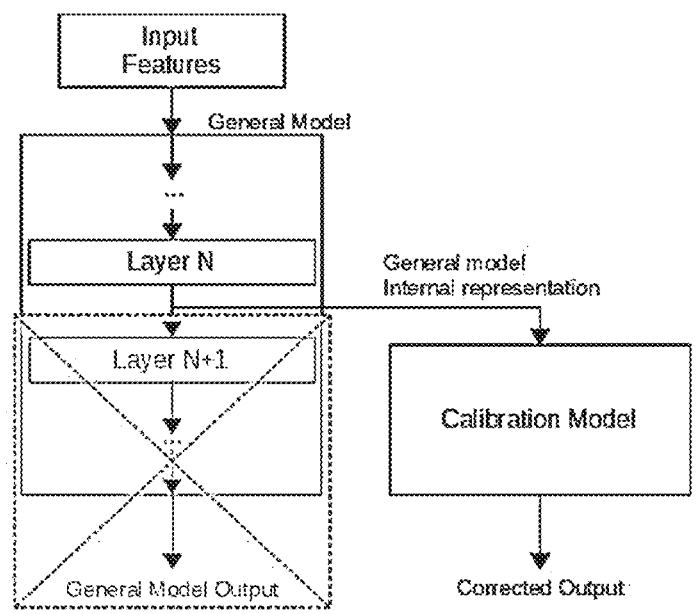
FIG. 18 is a schematic block diagram illustrating the method of FIG. 1, wherein another calibration model is used, according to another embodiment.

The second option, as illustrated in FIG. 18, would be to feed the features to the general model as described above, but capturing the output of a layer other than the output layer, so an internal representation of the model, as the input to the calibration model. The targets for training would again be the true position of the stimulus on screen at the time of image capture. Once trained, the calibration model would replace all of the layers downstream of the layer used for training, as illustrated.

The data collection procedure for the calibration database would involve showing a series of stimuli to the user, while ensuring that the screen is covered entirely and evenly, as known in the art. To ensure the quality of the data, the calibration procedure should also be kept as short as possible and should try to maximize user engagement.

Many strategies are available here. The stimuli could be made to appear at random locations throughout the screen, requiring the user to find each stimulus before the pictures are taken. The stimuli could be made to appear in a sequence between pairs of points on the screen, chosen at random, requiring the user to find the start point. The stimuli could be made to appear in a sequence between a set of predetermined, but disconnected pairs of points, thus making a single stimulus appear to move along a predetermined but disconnected path. Finally, the stimuli could be made to appear in a sequence along a predetermined, continuous path, thus creating the illusion (in other terms, appearing to the user on the screen providing a perception) of a single stimulus moving along said path. These strategies could be mixed, thus creating a calibration procedure during which each strategy is used for a certain amount of time.

In one embodiment, the chosen stimulus moves along a predetermined path while capturing a video of the user's face. The same effect could be achieved by capturing pictures at a certain framerate. By using this strategy, the user never has to find a new stimulus position after it having jumped, thus reducing the likelihood of bad datapoints being captured while the user was looking for the stimulus. This strategy also allows to capture a maximum of datapoints in a set amount of time, since by having the stimuli "jump" from location to location, some time would need to be allocated for the user to find the next stimulus to avoid the aforementioned problem. Finally, this strategy, being deterministic, allows the user to become familiar with the calibration procedure, thus increasing the likelihood of the user following the path of the stimulus exactly.

Once the data is captured, a machine learning algorithm needs to be chosen with which the calibration models will be trained. Given the relatively low complexity of the data, these algorithms would likely be the types of algorithms previously described, so ridge regression, decision trees, support vector machine, or even linear regression. More complex algorithms like artificial neural networks could also be used for a specific application.

Figure 19:
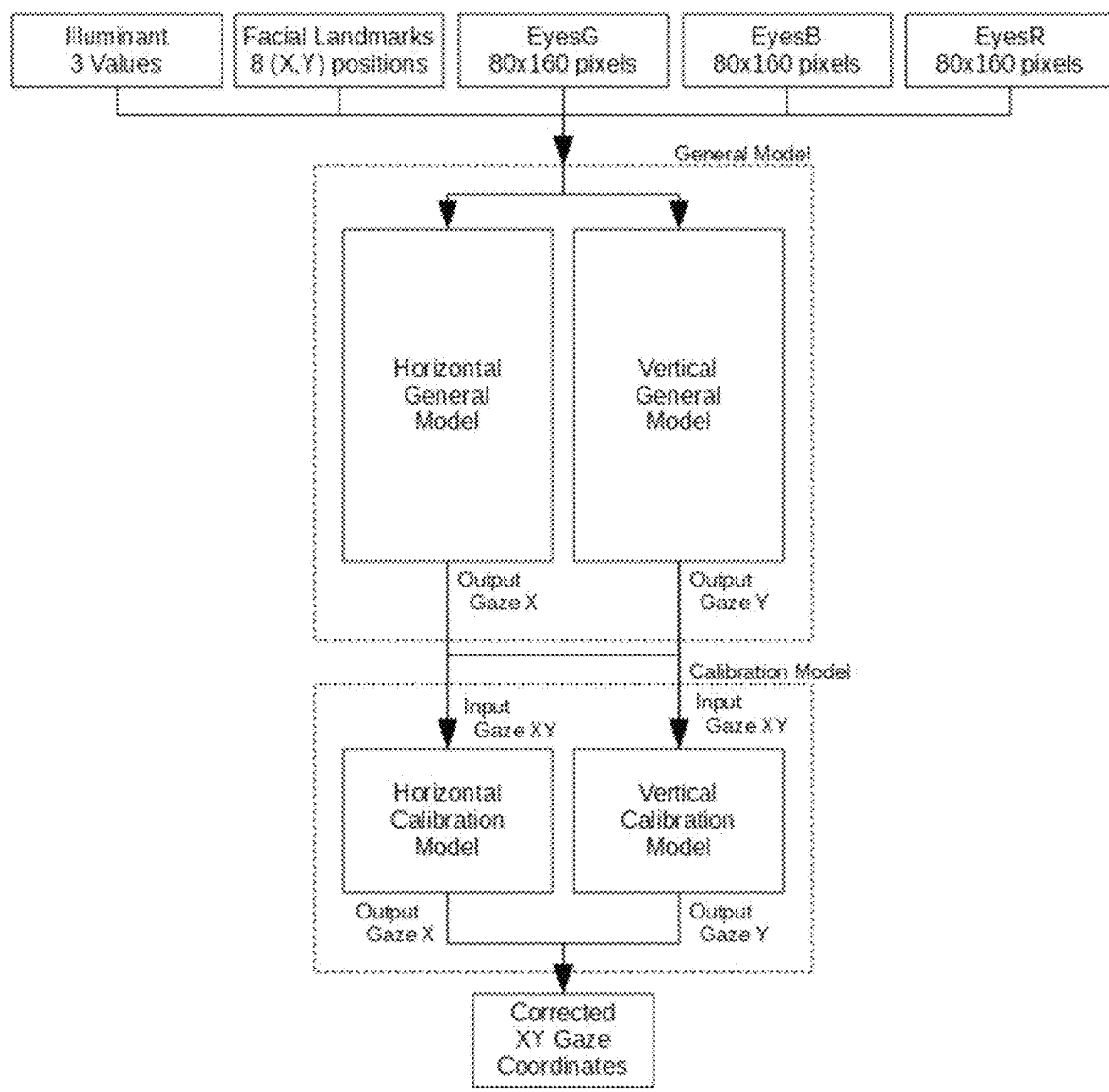
FIG. 19 is a schematic block diagram illustrating the method of FIG. 1, wherein the calibration model has a vertical calibration model and a horizontal calibration model, according to another embodiment.

FIG. 19 illustrates a schematic of the implementation of the proposed calibration model, according to one embodiment. The general model is composed of two subsystems, each of which takes in the same features and outputs either the X or the Y gaze coordinates. These gaze positions are then both fed to the calibration model, which is also composed of two subsystems. Each of those subsystems takes in both gaze coordinates and outputs either a corrected X or Y gaze coordinates.

Calibration models were then trained using support vector machines. For each device orientation, two calibration models were trained. Each model takes in the XY gaze coordinates output by the general models proper to the appropriate device orientation, and outputs either the X or Y corrected gaze coordinate. It would also have been possible to have a single model outputting both gaze coordinates, but tests have shown that the independent determination of X or Y corrected gaze coordinate provides better results.

Figure 20:
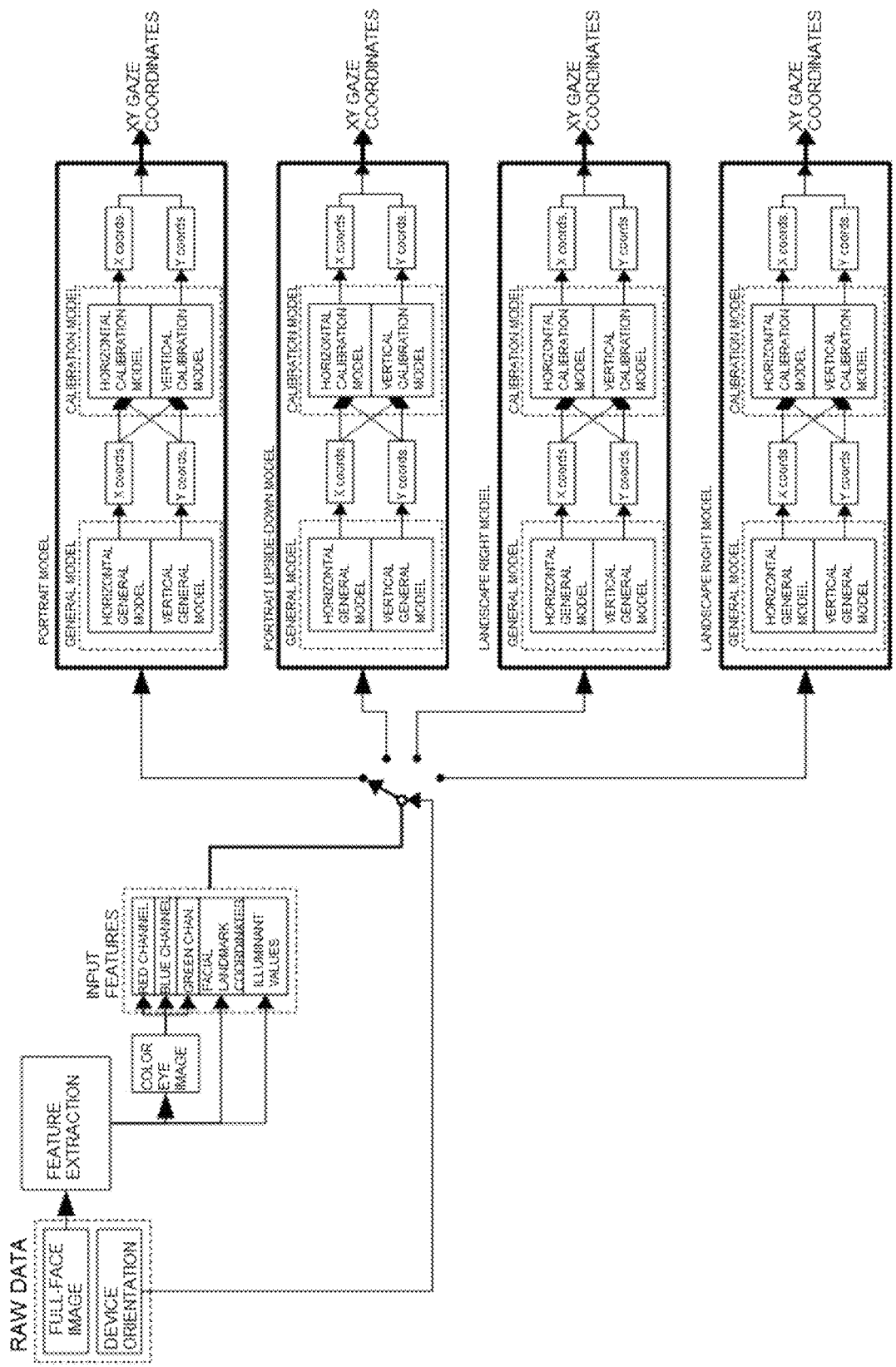
FIG. 20 is a detailed block diagram of an entire system for determining a gaze position of a user, according to one embodiment.

Reference is now made to FIG. 20 which shows an entire system for determining a gaze position of a user, according to one embodiment.

For every gaze position to be estimated, the device on which the system is installed will produce an image taken with a digital camera that shows the face of the user, and the orientation of the device or camera, depending on the system. For example, a smartphone or tablet device would use the front-facing camera, and would also provide the orientation of the device, while a desktop computer would use a webcam, typically mounted on top of a screen, and would provide the orientation of the webcam.

From the initial image, five input features are extracted. These features include the three crops of the original image that contains both of the user eyes, or the region of the face where the eyes would be. These features also include the XY coordinates of a set of facial landmarks, and the estimated illuminant values of the initial image.

The system has four prediction streams, one for each of the four following device orientations: portrait, portrait upside-down, landscape right and landscape left. Each of these prediction streams contains a general model and, if calibration has been performed for this orientation, a calibration model. Both the general and calibration models for each stream contain two subsystems. One subsystem estimates the horizontal gaze coordinate from the input features, while the other subsystem estimates the vertical gaze coordinates from the same features.

The predictions stream to be used is determined by the device orientation, which acts like a selector. The system could either have all streams produce a gaze position estimate, with the selector being used to select which output to use. Alternatively, the selector could be used to select which of the prediction streams should be used for a given feature set. The latter option enables to reduce computational costs.

The method described herein performs particularly well for making various applications involving gaze tracking for user interfaces, such as a user interface on a smartphone, on a tablet, or on a screen of some sort. Practical application involving interactions with contents appearing on these interfaces can be made by taking advantage of the high accuracy (smaller than 1 cm) that can be achieved using the present method. This accuracy is notably achieved by a judicious selection of input images (such as a concatenation of cropped eye images with the environment removed). This accuracy also originates from ensuring, through the architecture as described above, that the algorithm, namely the neural network, can adapt automatically to the illumination context and gives a preference to the internal representation originating from one of the color component images which gives the best results in that illumination context. The complete separation of color component images (e.g., three color-component images of the concatenated cropped eyes) before applying a distinct neural network stream to each of them, ensures that each one is treated distinctly and can later be selected alone for further treatment by the neural network using the most appropriate color component image given the illumination context.

The method described herein performs particularly well when compared to other methods found in the literature, for example the study made by Krafka et al., "Eye Tracking for Everyone" from MIT, available at http://gazecapture.csail.mit.edu/cvpr2016_gazecapture.pdf. This study uses four inputs: each separate eye (cropped), the whole image, and a binary mask indicating face position in the image.

The present disclosure describes using only facial landmark coordinates and not the whole face. In the MIT project, the first layer needs considerable time to be trained to identify a person's head and its position in the complete image. The presence in the image of the environment around the head is superfluous and complicates the training of the model. The MIT model also indicates a precision of 1.34 cm-2.12 cm on mobile phones. This accuracy is not sufficient for real-life applications such as the identification of keyboard elements which have a screen height or width below 1 cm. The method describes herein takes advantage of inputs and an architecture which allow identifying the buttons of a typical smartphone keyboard, with an accuracy in either X or Y below 1 cm, therefore sufficient for real-life applications. This is at least because we have identified that using the whole image being acquired is not useful and requires significant computational resources. In the present method, in addition to the composite image of the cropped eye images (cropped images of the eyes put together in single image) used as the input for color component images, the facial landmark coordinates (alone) are fed to the first layer of the network. The requirement for computational resources is thereby reduced. Instead of the whole picture of the environment fed to the neural network, we use the illuminant values as a proxy for the environmental conditions, again reducing the requirement for computational resources, both in real-time application and during training. Moreover, the MIT project failed to identify the benefit of separating RGB components of the image at the input as described herein, which also provides technical advantages in terms of accuracy when detecting edges in the eye anatomy that are useful for gaze tracking.

The method described herein also performs particularly well when compared to other methods found in the literature. For example, Zhang et al., available at https://arxiv.org/pdf/1504.02863.pdf, describes a method which is only sequential, with no parallel networks. They also teach using only one eye, from which they lose accuracy. The method also solves a different problem, namely finding an eye angle, which has its own specificities as it does not deal with head position, which needs to be taken into account if the desired output is ax X,Y position.

The method described herein also performs particularly well when compared to EVA Facial Mouse, a mobile application developed by Vodafon and available at http://www.fundacionvodafone.es/app/eva-facial-mouse. This application uses facial movements, not the eyes, to control the mouse pointer on a device screen. This is not at all applicable to a completely paralyzed person, who cannot move their face.

The method described herein also performs particularly well when compared to U.S. patent U.S. Pat. No. 10,127, 680. In this document, there is no prior training of the network. Calibration images need to be fed to the network in the first place. After collecting calibration images, the network is trained. Actual accuracy is expected to be very low due to various factors, notably the lack of training of the network. This method should therefore not be expected to work in real-life conditions as it is described therein.

The hardware necessary to perform the method includes any device capable of image acquisition, which is normally called a camera. The camera is essential as it collects the images in a proper format at a proper rate and color conditions to be fed to the analysis system. Since the analysis system needs to be trained, an appropriate computer system needs to be used. This appropriate computer system is required for training, but may not be required for steps other than training. Actual real-time gaze determination needs to be performed by a computer system, but the requirements for computing power can normally be met by a typical mobile device such as a smartphone or tablet of good quality. Therefore, having a computer system (not necessarily the same one as for training) in communication with the camera for image acquisition is essential for running the method.

Computing may be performed in various specific manners depending on the context. As stated above, training of the system needs a significant computing power to be performed, but once it is trained, the algorithms can run on a simpler computer such as a tablet computer. However, if calibration needs to be done, calibration images can be advantageously sent over a network to a remote server (or to a server in a cloud computing arrangement) where the calibration model can be prepared. Once the model is calibrated on the remote server (with a presumably more significant computing power than a tablet or smartphone), the calibrated model is sent back to the tablet or smartphone or other similar device for actual use of the calibrated model, locally, on the client computer. One may also contemplate performing the calibration directly on the client computer, assuming it has enough computing power to do so and also assuming the complete calibration model is installed thereon, in which case the step of sending calibrations images to a remote server and retrieving a calibrated model can be bypassed.

The embodiments of the gaze tracking method described above can be used for various purposes. An example of an implementation of the gaze-tracking method described above, can involve using it in an application installed on an electronic device such as a smartphone, tablet and the like, for tracking the gaze of the user with respect to the screen in order to trigger operations thereon, or collect information, related to what is presented on the screen.

The output of the method, i.e., X,Y coordinates with respect to a reference point defined with respect from the camera, can be transformed to a screen coordinate using other inputs. For example, the relative position (normally fixed) between the camera and a reference point (e.g., the top left corner of the screen) should be known, as well as the screen size and screen resolution which can be queried in the device settings/parameters by the mobile application installed on the device. Using these data, the X,Y output can be transformed to pixel coordinate on the screen, or any other equivalent thereof. If only an X or Y value is needed, then this is transformed into a pixel row or column on the screen.

Using this transformation into a screen location being looked at can be useful to provide a way for a user to interact with the contents presented on the screen being looked at using only eye movements. Other types of body movement may exist but are not required to use the method described above, as eye direction is sufficient. This is useful for a user who is paralyzed or suffers from another problem which prevents all movements (including small facial movements) and verbal communication. Usually, a paralyzed person is able to move their eyes.

For example, on-screen elements which make up the graphical user interface can be triggered or actuated using only the gaze, identified by the method as being pointing toward them. These on-screen elements can include buttons, links, keyboard elements, and the like. Integrating the gaze-tracking method with the larger context of electronic device usage can therefore ensure proper interactivity of the paralyzed person with the screen of the electronic device, thereby using a user interface effectively using their eyes only. This requires the gaze-tracking application to communicate the results of the tracking in terms of screen position to the operating system of the device or to applications running thereon, to allow real-time interactivity, as if the person was using a mouse pointer or tapping on a touch screen. If the method is applied in such a context, then the use of the electronic device having a screen becomes essential.

Other applications can also be contemplated, for example by assessing where on a display element of some sort the person is looking. For example, a camera may acquire images of a person looking at a poster or panel and the method can be used to identify the location on the poster or panel where the person is looking. This can also apply to user interfaces which are displayed using technologies other than a device screen, for example using projection or immersive environments. The method can therefore determine, through geometrical transformations of the referential (e.g., into a pixel location on the screen), that the person is looking at displayed user-interface elements such as buttons, links, keyboard elements, and the like, on a projected image or virtual image, and user interaction with the interface elements can then be triggered.

Section 3—Neurological Disease-Related Eye Gaze-Pattern Abnormality Detection

Now referring to neurological disease-related eye gaze-pattern abnormality detection, and according to an embodiment, a similar approach to that described in the previous sections of the present description is used to develop a diagnostics suite for neurological conditions that affect eye movement patterns. This section relates to the method shown in FIG. 33, already described above, and contains numbered subsections for greater clarity, since references are made to such subsections later in the description. It is well documented in the medical literature that certain neurological conditions cause abnormal movement patterns in the eyes. The system as described herein comprises, according to an embodiment, three main parts that will be explored in the following sections. These parts are: a stimuli library, a dataset and expert models.

3.1 Stimuli Library

As mentioned herein, a link exists between certain neurological pathologies and abnormal eye movement patterns. Different pathologies elicit different abnormalities in eye movement patterns, however, and so the method described herein comprises performing tests from a bank of tests. The tests, referred to herein also as "eye gaze-pattern tests" are designed to facilitate the detection of different abnormalities in the eye movement patterns, associated to pathologies.

The bank of tests comprises a set of visual stimuli to be presented to the user using the computing device having a display on which gaze tracking is performed, as described above. Each of the visual stimuli is designed to elicit a specific eye movement pattern abnormality, if it is present in the user ocular movement. Such tests include saccade tests, anti-saccade tests, fixation tests and free-viewing tests. In the free-viewing test, the user is tasked with simply looking at a specific image, such as a face or a landscape. The tests in the bank of tests may also comprise an optokinetic nystagmus test. The tests in the bank of also comprise a moving visual target test, in which the movement of a target may be linear or non-linear.

These tests may be strung together into a single, longer test to be administered as a "broad-spectrum" test of sorts, or as individual tests if a specific pathology is suspected.

According to an embodiment, the following tasks may form one or more eye gaze-pattern tests and may be included in a software application installed on the computing device and being executed thereon.

In this document, positions of various points on the screen is provided in degrees of visual angle. The conversion in mm or inches may be done by estimating a distance of the eyes from the screen and by using the screen dimensions which may be extracted from the model of the display (typically a tablet computer from which dimensions may be known from the model which is determined from the operating system).

Since the tablet computer screen dimensions are typically given in Width (in pixels), Height (in pixels), and pixels per inch (ppi), the width and height of the screen in inches may be calculated as Width/ppi and Height/ppi.

3.1.1 Calibration Task

The calibration is similar to the one used in the gaze-tracking method described above, with several differences. In the context of the calibration task, the application instructs the display of a target and its movement around the edge of the screen, and its subsequent movement to cross the screen diagonally along both diagonals. A video of the user including the eyes is captured, preferably by the built-in camera of the computing device on which the target is displayed (i.e., the tablet or smartphone, as described above) while they perform the task, and each frame from of this video is matched to the position of the target on screen when the frame was acquired. This, as well as some metadata about the device that was used to display the stimuli and acquire the videos, and information about the user, forms a raw data set. This is discussed in more detail in a later section.

Now in greater detail (referring to FIGS. 21A-21C), the calibration task begins with a target having, for example, an outer black circle, an inner white circle, and a black cross in the center of the circle.

1. At the first step, the target appears in the top left corner of the screen, at position p0. The target remains stationary for 2 seconds.
2. After the first 2 seconds, the target begins to move horizontally to the right at a speed of 8.65 degrees/second until it reaches the upper right corner of the screen, p1. For example, the target begins to move horizontally to the right at a speed of 350 points/second (which roughly corresponds to 8 degrees/s for a user positioned 45 cm from the screen) until it reaches the top right corner of the screen, p1.

3. Once at the upper right corner of the screen, the target begins to move vertically at the same speed as before, downwards towards the bottom right corner of the screen, p2.
4. Once at the lower right corner of the screen, the target begins to move horizontally at the same speed as before, leftward towards the bottom left corner of the screen, p3.
5. Once at the bottom left corner of the screen, the target begins to move vertically at the same speed as before, towards the upper left corner of the screen, p4.
6. Once at the upper left corner of the screen, the target begins to move diagonally at the same speed as before, downwards and rightward to the bottom lower right corner of the screen, p5.
7. Once at the lower right corner of the screen, the target begins to move vertically at the same speed as before, towards the upper right corner of the screen, p6.
8. Once at the upper right corner of the screen, the target begins to move diagonally at the same speed as before, downwards and leftward to the bottom lower left corner of the screen, p7.

Once these 8 steps are finished, the calibration task may be completed. A visual explanation of each step's path is shown in FIGS. 21A-21C. No metric extraction is required for the calibration task.

In at least one embodiment, the calibration sequence is repeated an additional time, with the subject asked to change their head position in between both sequences.

The second calibration sequence follows the following order (using the target positions outlined for FIGS. 21A-21C). Starting at P3 (2113), the target moves vertically to P4 (2114). Then the target 2130 follows a down/up parabolic trajectory to P6 as illustrated with a down/up parabolic trajectory in FIG. 21D (arrows 2125*a*, 2125*b* show the directions of the target). FIG. 21D provides an illustration of an example of the down/up parabolic trajectory. Then the target 2130 moves down to P5. Then the target follows an up/down parabolic trajectory to P3 as illustrated in FIG. 21E and the direction is illustrated with arrow 2125*c*. Then the target moves up to P4 (2114).

Examples of accompanying on-screen instructions may be: "Look at the black and white circle that will appear in the upper left hand corner of the screen." "Follow it as accurately as possible with your eyes until it stops."

According to an embodiment, for any of the instructions mentioned herein, there can be an audio recording of the instructions being read. According to an embodiment, for any of the instructions mentioned herein, there can be a video/demo with indications overlaid explaining how to perform the task.

In at least one embodiment, the system prompts the user to change the head position. The calibration sequences may be interrupted twice (for example and without limitation, at the ⅓ and ⅔ time points of the calibration task) to request the subject (user) to change their position by aligning their head orientation with that of a centrally presented rectangle (or, for example, another form such as a circle, ellipse, polygon, etc., which has a shape generally enclosing a typical head shape) on the screen. Thus, the system performs an alignment of the eyes of the user with respect to the rectangle (or, for example, an ellipse) displayed on the screen.

The following on-screen instructions may be shown before the task begins: "Throughout this task, you will be shown a rectangle frame at the center of the screen to help you position your head. Adjust the position of your head as indicated until the outer screen frame turns green. An image will then appear in the top left corner and start moving. Please follow it with your eyes as accurately as possible while it moves across the screen until it stops."

The following on-screen instructions may be shown at the beginning of the task and is common to all tasks for head positioning: "Place your head in the center of the screen, vertical, not tilted." The following on-screen instructions may be shown approximately at ⅓ through the task: "Tilt your head to the left a bit." The following on-screen instructions may be shown approximately at ⅔ through the task: "Tilt your head to the right a bit."

Thus, the position of the user's (subject's) head is controlled during the calibration task. During approximately the first third of the calibration task, the user's head is slightly (for example, by about 5 to about 15 degrees) tilted towards one side of the user—for example, to the left. During approximately the following two thirds of the calibration task, the user's head is slightly (for example, by about 5 to about 15 degrees) is tilted towards another side of the user—for example, to the right. Requesting tilting towards different sides of the head of the user results in the user's head being tilted in response to (and according) to such a request. In at least one embodiment, the position of the user's head is taken into account later when the calibration data, collected during the calibration task, is used later to compare with the data collected during the other tasks.

3.1.2 Fixation Task

The fixation task is a task in which the user is asked to look steadily (fixate) at a number of points, indicated by some shape, on the screen of the mobile computing device. According to an embodiment, nine points are used: one in the center to evaluate primary position fixation, one point in each corner and one point in the center of each side of the screen. The positions of the points are shown in FIG. 22.

Task Parameters

To perform the fixation task, a black cross is positioned at 9 different points on the screen to be displayed for 7 seconds each, as shown in FIG. 22. The 9 positions are as follows:
a) 16 degrees in the top left corner (2.41 inches left, 3.63 inches up);
b) 15 degrees above the centre (3.63 inches);
c) 16 degrees in the top right corner (2.41 inches right, 3.63 inches up);
d) 10 degrees to the left of centre (2.41 inches);
e) The centre of the screen;
f) 10 degrees to the right of centre (2.41 inches);
g) 16 degrees in the bottom left corner (2.41 inches left, 3.63 inches down);
h) 15 degrees below the centre (3.63 inches);
i) 16 degrees in the bottom right corner (2.41 inches right, 3.63 inches down).

Each stimulus position from the positions a)-i) described above is presented in order from left to right, top to bottom. FIG. 22A shows the combination of all crosses which, in practice, are displayed successively as described herein, in accordance with at least one embodiment.

In at least one embodiment, the fixation task may be implemented as follows. A white cross on a black screen positioned at 5 different positions on the screen to be displayed for 7 seconds each. The 5 positions may be pre-determined as follows, and presented in random order for each subject: 583 points above the center (which roughly corresponds to 14 degrees of visual angle when positioned at a distance of 45 cm from the screen); 583 points below the center; 412 points left of the center (which roughly corresponds to 10 degrees of visual angle when positioned at a distance of 45 cm from the screen); 412 points right of the center; and the screen center.

FIG. 22B shows a combination of all five crosses which, in practice, are displayed successively as described herein, in accordance with at least one embodiment.

For example, the visual angle may be converted to a distance (points) on the electronic device, such as a tablet, for example an iPad™. The angle conversion formula for this task and the other tasks described herein may be used as follows:

$$POINTS=132*(TAN(RADIANS(ANGLE)))*(DISTANCE), \quad (1)$$

where the number of POINTS depends on the chosen ANGLE (in degrees) relative to the screen center, and the expected DISTANCE (in inches) between the screen and the user. For example, the chosen DISTANCE may be 17.17 inches (45 cm). The chosen ANGLE may vary as a function of the task and visual target.

Eye-movement metrics (also referred to herein as "features" when the metrics are averaged over several trials) that may be determined based on the video captured (filmed) during the fixation test are: a. Mean error for each target; b. Mean absolute error for each target; c. Saccadic intrusions (x number of saccades per fixation period) for each target, such as, for example: square wave jerk; square wave pulse (SWPs are similar to SWJ in their morphology and conjugacy, but they usually oscillate on one side of fixation, have a higher amplitude (usually greater than 5°) and a distinctive shorter intersaccadic interval (ISI) (about 80 ms)); ocular flutter; opsoclonus. d. Presence of nystagmus for each fixation period (pendular or jerk, wherein, for jerk nystagmus there is a slow eccentric drift followed by corrective jerk towards the target, whereas for pendular nystagmus both components are considered slow), which may be determined based on: amplitude for each fixation period, frequency for each fixation period, velocity of slow phase for each fixation period, direction of nystagmus for each fixation period.

Intrusions

In at least one embodiment, metrics, that may be extracted and are related to intrusions from the data on a trial basis (in other terms, averaged per trial) are: SWJ rate, SWJ amplitude, SWJ peak velocity during first saccade, SWJ deviation from horizontal (vertical component) wherein SWJ are by definition horizontal in HC, SWJ duration which represents time elapsed between the rise and fall of a SWJ, SWJ interval—time elapsed between SWJs (ignoring OSIs). Such metrics related to SWJ rate are also referred to herein as SWJ saccade metrics. The following metrics may be also extracted: OSI rate, OSI amplitude, OSI peak velocity, OSI duration—time elapsed between the onset and offset of OSI, OSI interval—time elapsed between OSIs (ignoring SWJs), and blink rate.

Features for the intrusions, that are averaged across trials, are: average SWJ rate, average SWJ amplitude, average SWJ peak velocity, average SWJ deviation from horizontal, average SWJ duration, average SWJ interval, average OSI rate, average OSI amplitude, average OSI peak velocity, average OSI duration, average OSI interval, average blink rate, average blink to SWJ rate.

Gaze Drift and Stability

To take into account the gaze drift and stability, SWJ and OSI are removed from trace to compute drift and stability metrics. Metrics that may be extracted with regards to the gaze drift and stability, are: BCEA 68%; BCEA 95%; percentage of time within a defined radius around a target (2 degrees); percentage of time within a defined radius around a target (4 degrees); average vertical position; average horizontal position; length of fixation periods that is a period of fixation uninterrupted by saccades, blinks or noise.

The following features may be extracted with regards to the gaze drift and stability, are: average BCEA 68%; average BCEA 95%; average percentage of time within a defined radius around a target (2 degrees); average percentage of time within a defined radius around a target (4 degrees); horizontal gaze SD which is a standard deviation of the horizontal/vertical gaze position; vertical gaze SD; horizontal gaze drift which is a drift calculated by a linear fit (regression line) through all the consecutive gaze samples of the fixation period. The regression coefficient (expressed in degrees per second) of this line was considered as the mean drift during this fixation period. The other features that may be extracted with regards to the gaze drift and stability: vertical gaze drift; SE horizontal gaze drift which is the standard error of the estimate, reflecting the mean deviation of the gaze from the regression line, and which defines the fixation stability around the drift line (the SE horizontal gaze drift reflects any fixation instability that is not caused by either saccadic intrusions or drift); SE vertical gaze drift; average maximal fixation period; average fixation period.

An example of accompanying on-screen instructions is: —"Please fixate on the cross for 7 seconds, try to keep your gaze steady and avoid looking around the screen."

3.1.3 Pro-Saccade Task

Figure 23A:
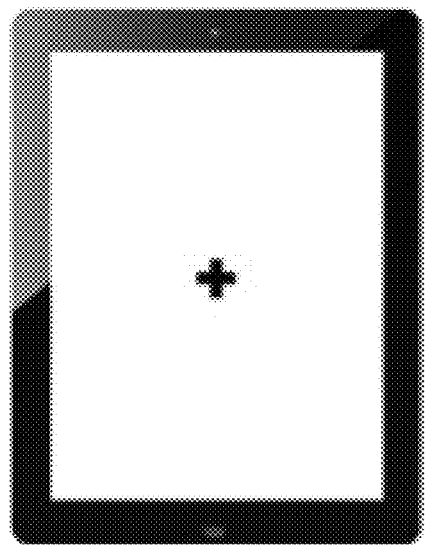
FIGS. 23A-23B are images illustrating a screen of a tablet or similar computing device displaying targets for a pro-saccade task, according to one embodiment.
Figure 23B:
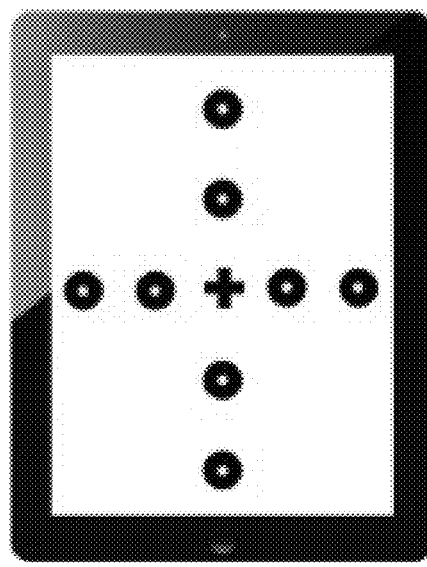

The pro-saccade task is a task in which the user is asked to fixate on a central cross, and when a stimulus (or target) is shown on screen off-center from the cross, to fixate on said stimulus. After a fixation time of about 1.5 second, the stimulus disappears and the central cross reappears, at which time the user should fixate on the central cross again. FIGS. 23A-23B show the central fixation cross (FIG. 23A) and the central fixation cross with all possible positions at which the targets can appear (FIG. 23B).

More precisely, the central fixation time of about 1.5 second may vary at random between 1 and 3.5 seconds. This may be done to prevent the user from anticipating the next appearance of a target. Alternatively, the central fixation time may be fixed.

The pro-saccade task is meant to evoke, if present, saccadic dysmetria, saccadic breakdown, and to evaluate the dynamics of the user's saccades, namely saccadic latency and peak velocity.

The pro-saccade task has the following steps.

a) The pro-saccade task begins with a black cross (target) positioned in the centre of a white screen (or, in some embodiments, with a white cross positioned in the center of a black screen), as shown in FIG. 23A. In other terms, a cross positioned in the center of the screen has color different from (contrast to) the background. This step is called the fixation period, and it lasts for a random duration for example, between 1.0 and 3.5 seconds.

b) After the fixation period ends, the central cross disappears and at the same time, a target consisting of an outer black circle, an inner white circle, and a black cross in the center of the circle, appears on the screen for 1.5 seconds at one of eight possible random locations, shown in FIG. 23B. This step is called the stimulus period. All 8 possible pre-determined stimulus locations are shown in FIG. 23B, but only one stimulus is randomly selected to appear for each stimulus period.

The coordinates for the 8 possible random locations of the target may be as follows: i. 15 degrees above the centre (3.63 inches); ii. 15 degrees below the centre (3.63 inches); iii. 8 degrees above the centre (1.93 inches); iv. 8 degrees below the centre (1.93 inches); v. 10 degrees to the right of centre (2.41 inches); vi. 10 degrees to the left of centre (2.41 inches); vii. 7 degrees to the right of centre (1.69 inches); viii. 7 degrees to the left of centre (1.69 inches).

According to an exemplary embodiment of the disclosure, the coordinates for the 8 possible random locations of the target may be as follows:
  i. 500 points above the centre (which roughly corresponds to 12 degrees of visual angle when positioned at a distance of 45 cm from the screen); ii. 250 points above the centre (which roughly corresponds to 6 degrees of visual angle when positioned at a distance of 45 cm from the screen); iii. 500 points below the centre (which roughly corresponds to 12 degrees of visual angle when positioned at a distance of 45 cm from the screen); iv. 250 points below the centre (which roughly corresponds to 6 degrees of visual angle when positioned at a distance of 45 cm from the screen); v. 400 points to the right the centre (which roughly corresponds to 10 degrees of visual angle when positioned at a distance of 45 cm from the screen); vi. 200 points to the right the centre (which roughly corresponds to 5 degrees of visual angle when positioned at a distance of 45 cm from the screen); vii. 400 points to the left of the centre (which roughly corresponds to 10 degrees of visual angle when positioned at a distance of 45 cm from the screen); viii. 200 points to the left of the centre (which roughly corresponds to 5 degrees of visual angle when positioned at a distance of 45 cm from the screen).
  c) After this 1.5 second period, the target disappears, the cross simultaneously re-appears, and the task begins with a new fixation period (at step 1).
  d) Once the fixation and stimulus periods have occurred 3 times each (for example, other number of repetitions can be used), the task ends. Once the target has appeared three times in each of the eight locations, the task ends.

All 8 possible stimulus locations (also referred to herein as a set of pre-determined locations on the screen) described above are shown in FIG. 23B, but only one stimulus is randomly selected to appear for each stimulus period.

The central cross disappears when the fixation period ends/stimulus period begins. The cross then reappears. In some embodiments, the cross reappears following the completion of the stimulus period.

The following features (eye-movement metrics) may be determined using the pro-saccade task: For correctly executed saccades: saccade latency, vertical/horizontal saccade latency (ratio), peak saccade velocity, vertical/horizontal peak saccade velocity (ratio), saccade endpoint accuracy (both signed and unsigned), number of reversals in acceleration (i.e., whether the movement from central fixation to a target is performed in a single saccade, or in a series of smaller saccades). When incorrect movements are made, the error rate (proportion of trials moved in correct direction).

Saccadic Onset and Timing

In at least one embodiment, for the saccadic onset and timing, the following metrics may be determined (extracted) from the data for each trial (test): latency which is time elapsed between onset of target appearance and the onset of the first saccade; time to reach target which corresponds to time elapsed between onset of target appearance and end of final saccade; and duration of first saccade.

For the saccadic onset and timing, the following features may be determined for learning, classification and prediction: average latency; latency SD—individual latency standard deviation; latency CV which is an individual latency coefficient of variation (which may be determined as a ratio of the standard deviation to the mean) which is a measure of individual variability when comparing populations with different means; average time to reach target; time to reach target SD; time to reach target CV; average duration/amplitude of first saccade; duration/amplitude of first saccade SD; duration/amplitude of first saccade CV; and vertical-to-horizontal average latency ratio.

Saccadic Amplitude and Precision

For the saccadic amplitude and precision, the following metrics may be determined (extracted) from the data for each trial (test): first gain which is the ratio of the actual first saccade amplitude divided by the desired saccade amplitude; final gain which is the ratio of the actual total saccade amplitude divided by the desired saccade amplitude.

For the saccadic amplitude and precision, the following features may be determined for learning, classification and prediction: average final gain correct saccade—measure of accuracy (average final position); average final gain correct saccade mean absolute error—measure of precision (average error from target); first gain SD; first gain CV; vertical-to-horizontal average first gain ratio; average final gain correct saccade—measure of accuracy (average final position); average final gain correct saccade mean absolute error—measure of precision (average error from target); final gain SD; final gain CV.

Saccadic Velocity

For the saccadic velocity, the following metrics may be determined (extracted) from the data for each trail (test): mean saccadic velocity, peak saccadic velocity, peak saccadic velocity/amplitude of saccade, leftward INO (ratio of the peak velocity between both eyes: ipsi/contralateral), rightward INO.

For the saccadic velocity, the following features may be determined for learning, classification and prediction: average mean saccadic velocity; mean velocity SD; mean velocity CV; average peak saccadic velocity; peak velocity SD; peak velocity CV; average peak saccadic velocity/amplitude of first saccade; peak saccadic velocity/amplitude of first saccade SD; peak saccadic velocity/amplitude of first saccade CV; average leftward INO; average rightward INO; vertical-to-horizontal average peak saccadic velocity/amplitude of first saccade ratio.

The following metrics may be also determined (extracted) from the data for each trail (test): a number of saccades required to reach target.

For the number of saccades, the following features may be determined for learning, classification and prediction: average number of saccades required to reach target; number of saccades required to reach target SD; number of saccades required to reach target CV.

The following metrics may be also determined (extracted) from the data for each trial (test): correct direction (binary); incorrect direction (binary). With regards to the saccadic errors, the following features are determined for learning, classification and prediction: percentage of trials with errors (direction).

It should also be noted that saccade detection in itself is a part of the feature extraction pipeline, though an important part. In the pro-saccade task, for example, saccade detection may be used to determine when the stimulus-induced saccade occurs, to cut other ones out of the signal to obtain accurate saccade metrics, and to determine if the saccade occurred in a single step or in multiple steps. Similar kinds of algorithms may be added on top of the saccade detection.

Examples of accompanying on-screen instructions may be: "Please fixate on the central cross." "When a round target appears, move your eyes (but not your head) as quickly as possible to the target." "When the target disappears, please return your eyes to fixate on the central cross."

Thus, the user is prompted to fixate his/her eyes on the central cross. The user is then prompted to move the eyes but not the head as quickly as possible to the target when a round target appears during the stimulus period. The user is then prompted to fixate on the central cross when the target disappears.

3.1.4 Anti-Saccade Task

The anti-saccade task is similar to the pro-saccade task in that it contains a central fixation point and eccentric stimuli, but the user is asked to look away from the stimuli. The anti-saccade task also comprises a fixation period and a stimulus period.

Figure 24A:
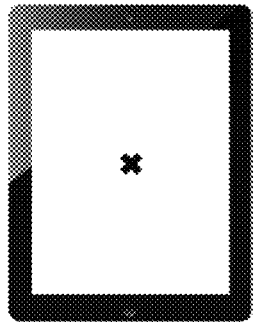

In the context of the anti-saccade task, and referring to FIGS. 24A-24D, the process starts with a fixation target in the center of the device's screen. For example, the target may be a black cross appearing in the center of a white screen as illustrated in FIG. 24A. This step is called the fixation period, and it lasts for a random duration between about 1.0 and about 3.5 seconds, where the random duration is chosen independently within this interval each time the task is repeated.

After an amount of time, which varies randomly between 1.5 and 3.5 seconds for each iteration, a stimulus appears either to the left side or the right side of the screen, also randomly. This stimulus remains on-screen for 100 milliseconds. The screen then remains blank for an amount of time varying between 600 and 400 milliseconds, decreasing as the task goes on to increase task difficulty. After this period, a second stimulus appears on the opposite side of the screen (i.e., opposite to the first).

This stimulus stays on-screen for 150 milliseconds, and contains a V-shaped symbol having an apex which can be pointing up, down, left or right, as shown in FIG. 25.

Finally, a screen is shown for 3 seconds displaying all four possible V-shaped symbols, and the user is asked to vocally express which of the four symbols they saw.

This task is configured to measure saccade latency and peak velocity, and to evaluate the error rate and correction rate for the anti-saccades themselves, as well as the success rate for the symbol identification part of the task.

Anti-Saccade Task Parameters

The anti-saccade task is similar to the pro-saccade task described above in Section 3.1.3 in that it also contains fixation and stimulus periods.

The anti-saccade task is shown in FIGS. 24A-24D. The task begins with a black cross appearing at position w/2×h/2, but rotated 45 degrees as seen in FIG. 24A. This step is called the fixation period, and it lasts for a random duration between 1.0 and 3.5 seconds. FIG. 24A depicts the fixation period, with central cross rotated 45 degrees (variable duration: 1 to 3.5 seconds), in accordance with one embodiment of the present disclosure.

Figure 24B:
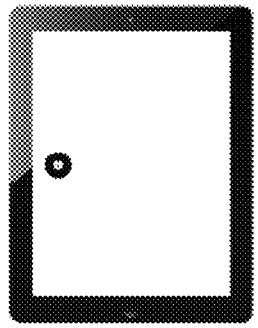

After the fixation period ends, the central cross disappears and at the same time, a target consisting of an outer black circle, an inner white circle, and a black cross in the center of the circle, appears on the screen for 100 milliseconds at one of two possible locations, as seen in FIG. 24B. This step is called the stimulus period.

Figure 24C:
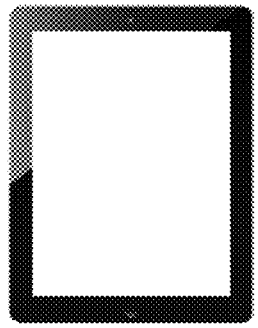
Figure 24D:
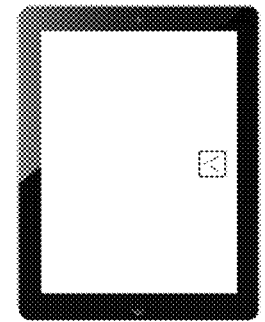

FIG. 24B depicts step one of the stimulus period (fixed duration: 100 ms), in accordance with one embodiment. FIG. 24C depicts step two of the stimulus period (variable duration: 600 ms to 400 ms), in accordance with one embodiment. FIG. 24D depicts step three of the stimulus period (fixed duration: 150 ms), in accordance with one embodiment. The coordinates for the 2 possible random locations may be, for example, as follows: 10 degrees to the right of centre (2.41 inches, or ~727 px to the right of centre on iPad 6), or 10 degrees to the left of centre (2.41 inches, or ~727 px to the left of centre on iPad 6).

After being displayed for 100 ms, the target disappears, and the screen is left blank for a period which decreases in length from 600 ms to 400 ms, in 50 ms increments, after every 10 successive stimulus periods (7 blocks of 8 trials with a blank period of [800 ms @250 ms], [600 ms, 550 ms, 500 ms], [450 ms, 400 ms]).

Following the blank screen, a symbol appears in the other stimulus location where the circle shape is not present. This symbol (a square with a v-shape inside) appears for a period of 150 ms and the v-shape will point in one of 4 random directions, either left, right, up, or down (for more information see FIGS. 24C and 24D). This concludes the stimulus period.

After one run through of the fixation and stimulus periods, a screen is displayed for 3 seconds prompting the user to answer which symbol they saw. FIG. 25 depicts the screen prompting the user after each run through of the task, asking the user to identify which symbol they saw during the task. At this point, the user may say out loud in which direction they perceived the v-shape was pointing (up, down, left or right), see FIG. 25 for more details. Note that during the display of this screen, the microphone should be activated to capture a vocal recording documenting the user's answer. The camera also continues to record video for eye-movement extraction during this screen.

In an alternative embodiment, the following steps may be performed as illustrated in FIGS. 24E-24H. 1. The anti-saccade task begins with a white cross appearing in the center of a black screen, as seen in 24E. This step is called the fixation period, and it lasts for a random duration between about 1.0 and about 3.5 seconds, where the random duration is chosen independently within this interval each time the task is repeated. 2. After the fixation period ends, the central cross disappears and at the same time, a target consisting of a white round target symbol, appears on the screen for 100 milliseconds at one of two possible locations, as seen in FIG. 24F. This step is called the stimulus period. The coordinates for the 2 possible random locations may be as follows: i. 409 points to the right of center (which roughly corresponds to 10 degrees of visual angle when positioned at a distance of 45 cm from the screen). ii. 409 points to the left of the center. 3. After being displayed for 100 ms, the target disappears, and the screen is left blank as in FIG. 24G (the duration of the blank screen is described below), which may be referred to a blank screen period. 4. Following the blank screen, a symbol appears in the opposite location of where the initial stimulus appeared (e.g. if the initial stimulus appears to the left of center, the symbol will appear to the right, and vice-versa). This symbol may be a white square with an arrow inside (for example, FIG. 24H), and the arrow may be oriented in one of 4 random directions: either left, right, up, or down. This concludes the stimulus period. 5. Task-difficulty may be modulated by changing both the duration of the blank screen between the initial stimulus and the arrow symbol and the on-screen duration of the arrow symbol. 6. In at least one embodiment, there are three distinct video blocks of 8 trials each. All trials in the first block have a blank screen period 1200 ms and an arrow symbol duration (stimulus period duration) of 400 ms. All trials in the second block have a blank screen period of 800 ms and a symbol duration of 250 ms. All trials in the final block will have a blank screen period of 550 ms and a symbol duration of 100 ms.

In at least one embodiment, the anti-saccade task comprises at least three distinct video blocks, each video block being configured to present on the screen a pre-determined number of trials, each trial having a fixation period, a blank screen period and a stimulus period. Thus, the system executes a pre-determined number of sets of trials (for example, the predetermined number of sets may be 3, while the set of trials may have 8 trials) and displays on the screen a target during a fixation period, a blank screen during a blank screen period and an arrow symbol during a stimulus period. The arrow symbol is oriented to a pre-determined direction. In at least one embodiment, the length of the fixation period, black screen period and the stimulus period shortens from the first video block to the third video block.

After each trial, a message on the screen is displayed for 5 seconds prompting the user to answer which symbol they saw (see FIG. 24H) by directing their gaze towards the arrow orientation (in other words, the arrow oriented) corresponding to what the user believes is the correct answer.

In at least one embodiment, the following eye-movement metrics (features) may be determined based on the analysis of the video recorded during the anti-saccade task: —Correct answers for the direction of the v-shape with respect to the duration of the blank period; —Audio recording of the user's answer; —Time spent in each response quadrant during the quiz period; —The error rate (proportion of trials where subject's gaze moved in the incorrect direction vs the correct direction); —Correction rate (proportion of trials where an error followed by a correction of direction was performed); —Saccade latency; —Peak saccade velocity.

Saccadic Onset/Timing

For the saccadic onset and timing, the following metrics may be determined (extracted) from the data for each trial (test): latency correct direction; latency incorrect direction; time-to-correct latency which is a latency between end of incorrect saccade and onset of saccade correct direction; time to reach target. For the saccadic onset and timing, the following features may be determined for machine learning, classification and prediction: average correct latency; correct latency SD; correct latency CV; average incorrect latency; incorrect latency SD; incorrect latency CV; average time-to-correct latency; time-to-correct latency SD; time-to-correct latency CV; average time to reach target; time to reach target SD; time to reach target CV; average duration/amplitude of first saccade; duration/amplitude of first saccade SD; duration/amplitude of first saccade CV; latency cost which refers to the cognitive cost of the antisaccade on latency (which is a difference between prosaccade average latency and antisaccade average latency (correct trials only)).

Saccadic Amplitude/Precision. For the saccadic amplitude/precision, the following metrics may be determined (extracted) from the data for each trial (test): first gain correct saccade; final gain correct saccade. For the saccadic amplitude/precision, the following features may be determined for machine learning, classification and prediction: average first gain correct saccade–measure of accuracy (average position); average first gain correct saccade mean absolute error–measure of precision (average error from target); first gain correct saccade SD; first gain correct saccade CV; average final gain correct saccade–measure of accuracy (average final position); average final gain correct saccade mean absolute error–measure of precision (average error from target); final gain SD correct saccade; final gain CV correct saccade.

Saccadic Errors. For the saccadic errors, the following metrics may be determined (extracted) from the data for each trial (test): correct direction (binary); incorrect direction (binary); corrected (binary). For the saccadic errors, the following features may be determined for machine learning, classification and prediction: percentage of trials with errors (direction); percentage of trials.

Correct responses. For the correct responses, the following metrics may be determined (extracted) from the data for each trial (test): pass/fail which is pass if gaze is within half the distance between the target (correct response) and the screen center. For the correct responses, the following features may be determined for machine learning, classification and prediction: percentage of correct (pass) responses.

Examples of accompanying on-screen instructions may be: "Please fixate on the x-shape at the centre of the screen." "When a round target appears, look in the opposite direction as fast as you can." "If you look in the correct direction, you will briefly see a v-shaped symbol pointing either left, right, up, or down. Remember the direction." "You will then be asked to say out loud which direction it was, and also look at the corresponding symbol which will be displayed on the screen." "You will have 3 seconds to answer, and then the task will start anew."

Alternatively, with regards to the alternative embodiment described above and illustrated in FIGS. 24E-H, the instruction may be: "If you look in the correct direction, you will briefly see an arrow symbol pointing either left, right, up, or down. Remember the direction." "You will then be asked to look at the corresponding symbol which will be displayed on the screen. There is no need to touch the screen, simply look at the correct answer with your eyes." "You will have 5 seconds to answer, and then the task will start anew multiple times."

After the first block of trials, the following message may be displayed: "Part 2 of 3. When you are ready, click Continue." After the 2nd block of trials, the following message may be displayed: "Part 3 of 3. When you are ready, click Continue."

FIG. 24E illustrates the fixation period, with central cross. FIG. 24F illustrates step one of the stimulus period. FIG. 24G illustrates step two of the stimulus period. FIG. 24H illustrates step three of the stimulus period. FIG. 24H illustrates the screen prompting the user after each run through of the task, asking the user to identify which symbol they saw during the task.

With regard to pro-saccade and anti-saccade tasks (anti-saccades are only horizontal), the saccade/anti-saccade targets appear at points corresponding to four possible degrees of visual angle from the screen center: vertical max: +/−15 degrees of visual angle; vertical mid: +/−8 degrees of visual angle; horizontal max: +/−10 degrees of visual angle; horizontal mid: +/−7 degrees, approximately. Although vertical anti-saccades may be used as well, the horizontal anti-saccades were determined to be particularly relevant to the diagnostics.

Assuming D stays constant at 50 cm, the following S values in inches would be: Vertical max S=3.63 inches; Vertical mid S=1.93 inches; Horizontal max S=2.41 inches; Horizontal mid S=1.69 inches.

3.1.5 Optokinetic Nystagmus Task

In the context of the optokinetic nystagmus task, the user is presented with either a vertical or horizontal full contrast, square-wave grating, moving across the screen. The vertical grating is a series of vertical, alternating black or white lines, preferably of equal width. The horizontal grating is identical, but with horizontal lines instead.

The optokinetic nystagmus task starts with a white screen comprising a central fixation cross, for a duration of 3 seconds. The vertical grating then appears and starts to move from left to right for 15 seconds. The fixation cross disappears while the vertical grating is on screen to not give users a fixation point that they can latch onto, thereby invalidating the task. After the vertical grating has been moving from left to right for the 15 seconds, the start screen reappears for 3 seconds. The vertical grating then reappears and moves from right to left for 15 seconds, after which the start screen appears for another 3 seconds. This sequence is repeated for the horizontal grating, but in this case, the grating moves up or down.

The optokinetic nystagmus task is meant to elicit optokinetic nystagmus. In the event that optokinetic nystagmus appears in any of the sequences, the amplitude and velocity of the nystagmus will be quantified and recorded.

Optokinetic Nystagmus Task Parameters

Note: the pixel measurements defined in this task are based on the dimensions of an iPad 6: width=1563 px, height=2048 px.

Figure 26:
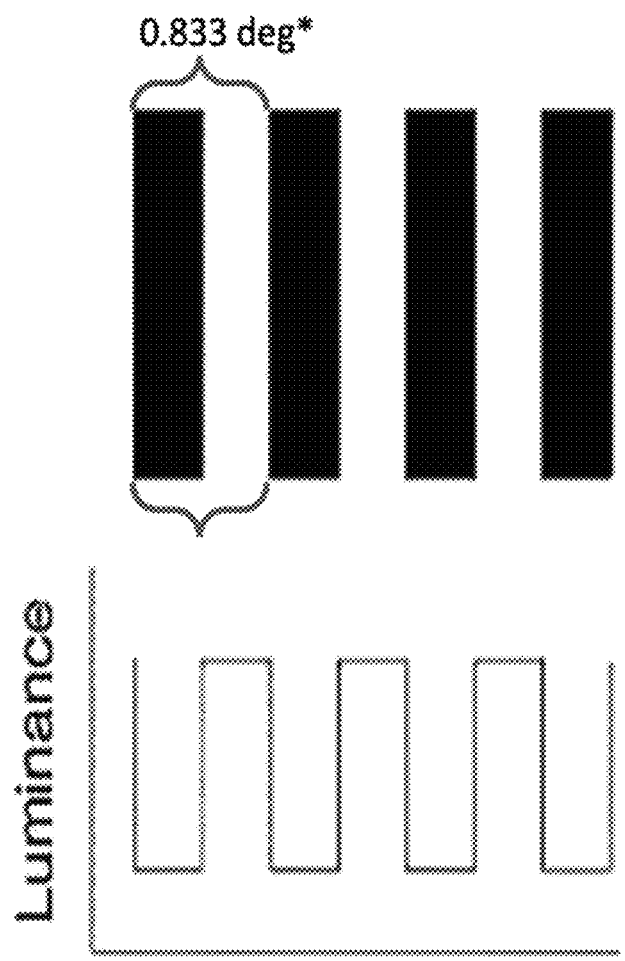
FIG. 26 is an image illustrating a screen of a tablet or similar computing device displaying an example of a 100%-contrast square wave grating, according to one embodiment.

The user is presented with a 100% contrast square wave grating (either in the vertical plane or the horizontal plane) with a fundamental spatial frequency of 0.833 cycles/deg (see FIG. 26 for more details). The 100% contrast square wave grating is displayed either as black lines of the grating on a white background, as illustrated in FIG. 26. Alternatively, the 100% contrast square wave grating is displayed as white lines of the grating on a black background. In at least one embodiment, the square wave grating is vertical as illustrated in FIG. 26, and moves horizontally. In at least one embodiment, the grating is displayed full-screen with a fundamental spatial frequency of one cycle per 100 points (or linewidth of 50 points).

Before and after the presentation of the gratings, there are screens displaying a white background with a black cross at the centre when the background is white. In other terms, before and after displaying of the square wave gratings, a white background (if the lines of the grating are black) is displayed with a black cross at the center of the display (screen). If the grating Before and after the presentation of the gratings, there will be screens displaying a white cross centered on a black screen.

The order of screen displays may be as follows: First, a 3-second white screen with a black cross at the centre is displayed on the screen. After the 3 second period, the cross disappears and the first grating screen appears. A horizontal grating, as described above, is presented moving left to right at a velocity of 5 deg/s (~363 px/s) for 15 seconds. After 15 seconds, the horizontal grating continues to move left to right, but at an increased velocity of 10 deg/s (~726 px/s), for 15 seconds. After 15 seconds, a white screen and a black cross in the centre is displayed for 5 seconds. After the 5 second period, the cross disappears and the horizontal grating re-appears. A horizontal grating is presented, this time moving from right to left at a velocity of 5 deg/s (~363 px/s) for 15 seconds. After 15 seconds, the horizontal grating continues to move right to left, but at an increased velocity of 10 deg/s (~726 px/s), for 15 seconds. After 15 seconds, a white screen and a black cross in the centre is displayed for 5 seconds. After the 5 second period, the cross disappears and a new vertical grating screen appears.

A vertical grating, with the same spatial frequency described above, is presented moving up to down at a velocity of 5 deg/s (~363 px/s) for 15 seconds. After 15 seconds, the horizontal grating continues to move up to down, but at an increased velocity of 10 deg/s (~726 px/s), for 15 seconds. After 15 seconds, a white screen and a black cross in the centre is displayed for 5 seconds. After the 5 second period, the cross disappears and the vertical grating re-appears. A vertical grating is presented, this time moving from down to up at a velocity of 5 deg/s (~363 px/s) for 15 seconds. After 15 seconds, the horizontal grating continues to move from down to up, but at an increased velocity of 10 deg/s (~726 px/s), for 15 seconds.

FIG. 26 depicts an example of a 100% contrast square wave grating. 1 cycle (0.833/deg) is equal to about 92 pixels of width).

In at least one embodiment, the order of screen displays may be as follows:

1. A 3 second white cross centered on a black screen. After the 3 second period, the cross disappears, and the first grating screen appears. 2. A horizontally moving grating, as described above, is presented moving left to right at a velocity of 150 points/s for 15 seconds. 3. After 15 seconds, the horizontal grating continues to move left to right, but at an increased velocity of 300 points/s for 15 seconds. 4. After 15 seconds, a white cross centered on a black screen is displayed for 5 seconds. After the 5 second period, the cross disappears and a new horizontal grating re-appears, this time moving from right to left at a velocity 150 points/s for 15 seconds. 5. After 15 seconds, the horizontal grating continues to move right to left, but at an increased velocity of 300 points/s for 15 seconds. In at least one embodiment, the following eye-movement metrics (features) need to be extracted and recorded for each eye: presence of nystagmus for each grating presentation which may be characterised with: amplitude of nystagmus, frequency of nystagmus, velocity of slow phase, direction of fast phase; and persistence of nystagmus during fixation. In at least one embodiment, the following metrics may be calculated (determined) for each pair of slow drift and saccade (slow drift-saccade pair).

Slow drift phase. For slow drift phase, the following metrics may be determined: latency before initiation of slow drift which comprises only one measure, prior to first pair; duration of drift which is a time lapse between onset of grating motion and initiation of return saccade; maximal velocity during drift; velocity gain which is a ratio of eye velocity to grating velocity; distance travelled during drift which may be also referred to as amplitude of slow drift.

Saccade fast phase. During the saccade fast phase, the following metrics may be determined: max velocity during first saccade; distance traveled (amplitude) of first saccade; duration (time) of first saccade; number of saccades before return to slow-drift phase; distance between center of screen and final position (position at the end of the final saccade) before initiation slow drift; duration (time) between last saccade and initiation of next slow drift.

During the fixation of the optokinetic nystagmus task, when a central cross is presented for 5 seconds between the two grating directions (in other terms based on the data collected during the fixation), the following metrics are determined: amplitude of slow drift; amplitude of return saccade; maximal velocity during drift; maximal velocity during return saccade.

The following features, which are averaged for each of the 2 speeds and 2 directions, may be determined. The specific features are determined for each one of the phase (period) of the task: for slow drift phase, for saccade fast phase and during fixation phase when the central cross is presented for 5 seconds between the two grating directions.

Slow drift phase. Based on the data obtained during the slow drift phase, the following features may be determined: latency before initiation of slow drift; average duration of drift; SD duration of drift; CV duration of drift; average max velocity during drift; SD max velocity during drift; CV max velocity during drift; average velocity gain which is a ratio of eye velocity to grating velocity; SD velocity gain; CV velocity gain; average distance travelled—amplitude of slow drift; SD distance travelled; CV distance travelled.

Saccade fast phase. Based on the data obtained during the saccade fast phase, the following features may be determined: average max velocity during first saccade; SD max velocity during first saccade; CV max velocity during first saccade; average distance traveled (amplitude) of first saccade; SD distance traveled (amplitude) of first saccade; CV distance traveled (amplitude) of first saccade; average duration (time) of first saccade; SD duration (time) of first saccade; CV duration (time) of first saccade; average number of saccades before return to slow-drift phase; SD number of saccades before return to slow-drift phase; CV number of saccades before return to slow-drift phase; average distance between center of screen and final position (position at the end of the final saccade) before initiation slow drift; SD distance between center of screen and final position (position at the end of the final saccade) before initiation slow drift; CV distance between center of screen and final position (position at the end of the final saccade) before initiation slow drift; average duration (time) between last saccade and initiation of slow drift; SD duration (time) between last saccade and initiation of slow drift; CV duration (time) between last saccade and initiation of slow drift; total number of slow drift which refers to fast phase pairs.

During the fixation phase, when the central cross is presented for 5 seconds between the two grating directions, the following features may be determined: number of slow drift—fast phase pairs during fixation cross presentation; average amplitude of slow drift; average amplitude of return saccade; average max velocity during drift; average velocity during return saccade.

An example of accompanying on-screen instructions may be: "Please fixate on the cross at the center of the screen and hold your gaze there throughout the entire task, even once the cross has disappeared, until instructed otherwise." Additionally, there may be the following instruction: "Your eyes may feel drawn away during the task, which is perfectly normal. Do your best to maintain your gaze at the center where the cross was." Thus, the system prompts the user to keep the gaze at the center of the screen during the whole task and therefore manipulating (in other word, forcing) the gaze to stay focused while measuring various metrics and features described above.

3.1.6 Smooth Pursuit (Processing Speed) Task

Figure 27:
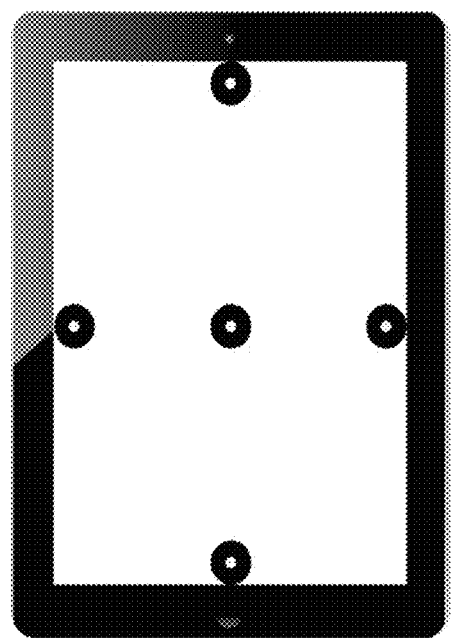
FIG. 27 is an image illustrating a screen of a tablet or similar computing device displaying a target (initial target and four different possible extremal targets, where one of them would follow the initial target) for a smooth pursuit task, according to one embodiment.

Task Parameters of the Smooth Pursuit Task a) In at least one embodiment, the smooth pursuit task begins with a target comprising an outer black circle, an inner white circle, and a black cross in the center of the circle, positioned in the centre of a white screen, as shown in the center of FIG. 27. This stimulus remains present at the centre of the screen for 2 seconds.

b) After this 2 second period ends, the target or stimulus moves smoothly along either the x or the y axis at a constant speed of 8.65°/s to one of the four extremes which are illustrated (all shown at once, and concurrently with the initial central target, for the purpose of illustration) in FIG. 27.

c) Once at one of the extremes, the stimulus immediately changes direction and moves, at the same rate and along the same axis, in the opposite direction until reaching the opposite extreme.

d) Once at the other extreme, the stimulus immediately changes direction again and moves at the same rate along the same axis back towards the centre.

e) Once at the centre, the stimulus immediately changes direction again, and moves along the other axis towards one of the extremes.

f) Once at one of the extremes, the stimulus immediately changes direction and moves, at the same rate and along the same axis, in the opposite direction until reaching the opposite extreme.

g) Once at the other extreme, the stimulus immediately changes direction again and moves at the same rate along the same axis back towards the centre.

h) Once back at the centre, the stimulus stops immediately, and stays stationary for 2 seconds. After this 2 second period ends, steps 2 through 8 are repeated 2 more times, but with increased speeds of 17.1°/s and 25.9°/s.

Thus the user's eyes are forced to follow the moving target, where the speed of the target's movement and the trajectory (or, in some embodiments, the options of the trajectory) are pre-determined. Each possible combination of directions and speeds are programmed so that the task may be randomized (within the pre-determined ranges of the speed and the options for the trajectory of the target's movement) effectively. One example of a possible run-through of this task may be: —The stimulus starts at the centre, —The stimulus moves along the x-axis to the left, —The stimulus moves along the x-axis to the right, —The stimulus moves back to the centre, —The stimulus moves along the y-axis to the top, —The stimulus moves along the y-axis to the bottom, —The stimulus returns to the centre.

In at least one embodiment, the smooth pursuit (processing speed) task has the following phases: initial fixation target phase and smooth pursuit trials phase. During the initial fixation target phase, which is implemented prior to each trial, a fixation target is displayed in the center of a black screen. In other words, each trial begins with a fixation target in the center of a black screen. The fixation target is presented by a pseudorandomly variable period of either 1000 or 2000 ms. Once the presentation period of the fixation target ends, this fixation target is then immediately replaced by the motion target in a different varying position (see below). Once the motion target appears it will immediately move at a constant velocity in one of several predetermined directions and speeds (see below).

In at least one embodiment, there are between 10 and 14, and preferably about 12 smooth pursuit trials. For each trial, there are 4 possible motion directions (up, down, left, right) with 3 possible target velocities (slow, fast, medium).

Each motion direction has its own starting position relative to the center (e.g., if going up, it starts below the center; if going left, it starts right of the center). Each target has its own starting distance from the center, with slower speeds starting closer to the center and faster speeds starting closer to the edge of the screen. In at least one embodiment, only 4 possible motion endpoints are used, one per direction, between about 5 and about 15 degrees, and preferably about 10 degrees from the center (e.g. if an up motion is presented, it finishes 10 degrees above the center, regardless of the speed and initial distance below the center).

For example, in an "up slow" trial, the motion target appears below the center of the screen at a first position (for example, 57 points corresponding to 1.4° below the center of the screen), moves up at a first velocity (speed) (for example, at a speed of 353 points/s corresponding to 8.65°/s) and stops above the center of the screen (for example, stops at 409 points—corresponding to 10°—above the center). For example, in an "up medium" trial, the motion target appears below the center (for example, 110 points or 2.69° below the center), moves up at a speed higher than the first speed (for example, at a speed of 703 points/s or 17.1°/s) and stops above the center (for example, at 409 points or 10°). In an "up fast" trial, the motion target appears below the center (for example, at 168 points or 4.12° below the center), moves up at the fastest speed that is approximately 3 times higher than the first speed (for example, at a speed of 1075 points/s or 25.9°/s) and stops above the center (for example, at 409 points or 10° above the center). In a "down slow" trial, the motion target appears above the center (for example, 57 points above the center), moves down (for example, at a speed of 8.65°/s corresponding 353 points/s) and stops at 409 points (10°) below the center.

In at least one embodiment, the trial order in the smooth pursuit task is as follows: start with the 4 slow trials (such as "up slow", "down slow", "left slow" and "right slow"), then medium, and then fast. In at least one embodiment, the order of the different motion directions between speeds is random.

The following eye-movement metrics (features) may be determined based on the video filmed during the execution of the smooth pursuit task:

Velocity gain (ratio of pursuit eye velocity to stimulus velocity), for right, up, left, and down.

Average lag (how far is the gaze lagging behind the stimulus) for right, up, left, and down.

Number of reversals in acceleration (to detect saccadic breakdown).

Gaze direction error relative to stimulus for when there is a change in stimulus direction.

Time it takes to correct gaze direction.

Smooth Pursuit features are the following metrics and features are extracted/computed for horizontal and vertical pursuits and slow, medium, fast and the other pursuits.

The following metrics are extracted based on the smooth pursuit: onset latency; pursuit gain which is a ratio of eye velocity to target velocity during pursuit (excluding catch-up saccades); proportion of time in pursuit; number of catch-up saccades; total amplitude of saccades; pursuit lag; first saccade latency; initial pursuit velocity; peak velocity; time to peak velocity; post-saccadic enhancement of pursuit eye velocity which is determined as a mean eye velocity after first saccade minus the mean eye velocity before the saccade.

The following features are determined: average onset latency; average pursuit gain; average proportion of time in pursuit; average number of catch-up saccades; average total amplitude of saccades; average pursuit lag; average first saccade latency; average initial pursuit velocity; average peak velocity; average time to peak velocity; average post-saccadic enhancement of pursuit eye velocity.

Examples of accompanying on-screen instructions may be: "Look at the circle that will appear in the centre of the screen." or "Follow it as accurately as possible with your eyes until it stops, you may make some mistakes, and this is perfectly normal."

In an embodiment where the cross displayed, the following on-screen instructions are displayed: "Look at the cross in the centre of the screen. When a moving target appears follow it as accurately as possible with your eyes until it stops. You may make some mistakes, and this is perfectly normal. Just keep doing your best." Thus, the system prompts the user to follow the target when it moves thus the system forces the user to control the gaze and to follow the path (also referred to herein as "trajectory").

3.1.7 Spiral Task

Spiral Task Parameters

Figure 34A:
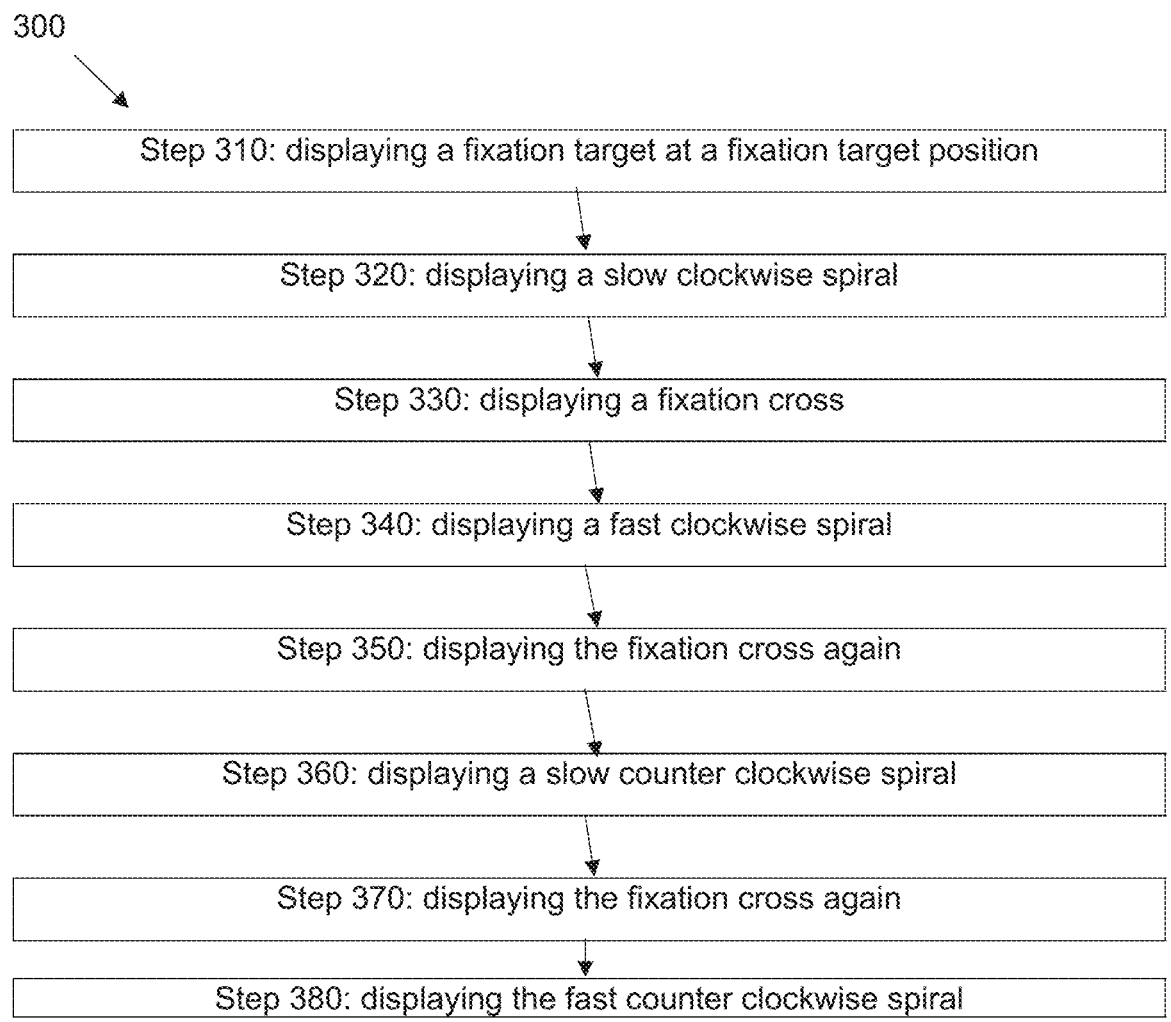
FIG. 34A is a flowchart of a spiral task method for detecting an eye gaze-pattern abnormality related to a neurological disease, in accordance with one embodiment.

FIG. 34A depicts a flowchart of a spiral task method 300 for detecting an eye gaze-pattern abnormality related to a neurological disease, in accordance with one embodiment. The spiral task method 300 implements the following steps of the spiral task.

1. In at least one embodiment, at step 310, a fixation target, such as, for example, a fixation cross, is displayed at a fixation target position. The fixation target position may be, for example, at the center of the screen. For example, the fixation cross (or another fixation target) may be displayed for 1 second at the center of the white screen.

2. Then, at step 320, a slow clockwise spiral starts to be displayed. The slow clockwise spiral emanates from a point where the fixation cross has been displayed (for example, at the center of the screen or at another fixation target position), moving farther away as it revolves around that point. The clockwise spiral function may be, for example:

$$x = r \cdot \phi \cos(-\phi),$$
$$y = r \cdot \phi \sin(-\phi),$$

where r, ϕ are the polar coordinates (r, ϕ), r is a radial coordinate and ϕ is an angular coordinate. Steps of increase of the angular coordinate ϕ may be adjusted. It should be understood that other spirals, described with other functions may be implemented. Such spirals are characterized as a curve which emanates from a starting point, moving farther away as it revolves around the starting point.

Figure 34B:
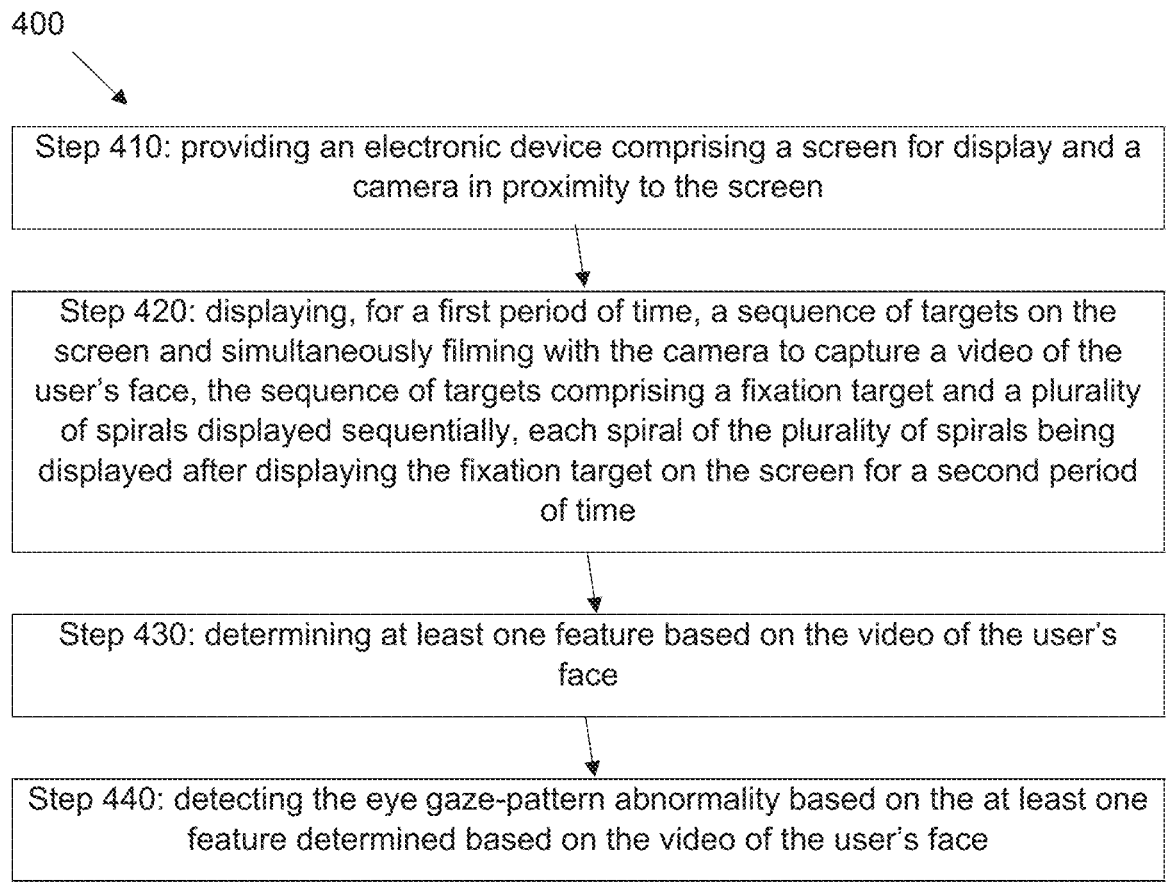
FIG. 34B is a flowchart of a spiral task method for detecting an eye gaze-pattern abnormality related to a neurological disease, in accordance with another embodiment.

FIG. 34B depicts a flowchart of a spiral task method 400 for detecting an eye gaze-pattern abnormality related to a neurological disease, in accordance with one embodiment. At step 410 an electronic device comprising a screen for display and a camera in proximity to the screen is provided. At step 420 a sequence of targets is displayed for a first period of time on the screen. The camera simultaneously films a video of the user's face. The sequence of targets comprise a fixation target and a plurality of spirals displayed sequentially, each spiral of the plurality of spirals is displayed after displaying the fixation target on the screen for a second period of time. In at least one embodiment, displaying of each one of the plurality of spirals is preceded by displaying of the fixation target at the fixation target position for the second period of time. The plurality of spirals may comprise two clockwise spirals and two counter clockwise spirals, and each one of the plurality of spirals revolve around the fixation target position.

At step 430, at least one feature based on the video of the user's face is determined. At step 440, the eye gaze-pattern abnormality based on the at least one feature determined based on the video of the user's face is detected.

Figure 35:
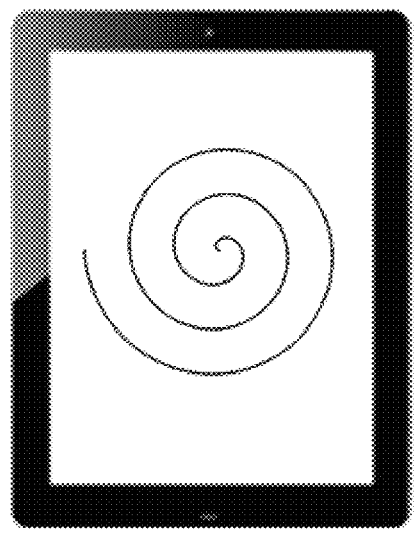
FIG. 35 is an example of a slow clockwise spiral displayed when implementing the spiral task, in accordance with one embodiment.

FIG. 35 depicts an example of a slow clockwise spiral when implementing the spiral task, in accordance with an embodiment.

For example, assuming coordinates in pixel on an iPad Pro® with an origin in the center of the screen, the angular coordinate φ may increase gradually between 0 and approximately 65 in 25 seconds, which corresponds to about 10.3 turns (for example, there may be 8 turns). The radial coordinate r may remain constant, for example, at approximately 15 (assuming coordinates in pixel on an iPad Pro® with an origin in the center of the screen). In at least one embodiment, the angular coordinate may be adjusted such that φ varies between 0 and 65 (about 10.3 turns) in 25 seconds while r remains constant at 0.05, with an origin at the center of the screen, so that x and y are in point units.

3. At step 330 of the method 300, fixation cross is displayed at the center of the white screen. For example, the fixation cross may be displayed for 1 second.
4. At step 340, a fast clockwise spiral starts to be displayed. Such clockwise spiral may also be described with the function:

$$x = r \cdot \phi \cos(-\phi),$$
$$y = r \cdot \phi \sin(-\phi).$$

Gradual rendering of the fast clockwise spiral on the screen may be adjusted. For example, the angular coordinate φ may increase (may be adjusted) between 0 and 65 and render on the screen about 10.3 turns (or, for example, between 7 and 13, for example about 8 turns) in 14 seconds. The radial coordinate r may remain constant. For example, the radial coordinate r may be approximately 15 (assuming coordinates in pixel on an iPad Pro® with an origin in the center of the screen) or 0.05, with an origin at the center of the screen, so that x and y are in point units. This fast clockwise spiral is displayed faster than the slow clockwise spiral displayed earlier at step 320. In other words, this fast clockwise spiral is displayed in a shorter period of time compared to the slow clockwise spiral displayed earlier at step 320.

In some embodiments, the following steps 350-380 are performed.

5. In some embodiments, at step 350, the fixation cross is displayed again at the center of the white screen. For example, the fixation cross may be displayed for 1 second.
6. In some embodiments, following the step 250, at step 360, a slow counter clockwise spiral starts to be displayed. Such counter clockwise spiral may be described with the functions:

$$x = r \cdot \phi \cos(\phi),$$
$$y = r \cdot \phi \sin(\phi).$$

Frame rates (in other words, steps of gradual rendering the spiral on the screen) may be adjusted such that φ increases between 0 and 65 and displays about 8 turns in 25 seconds. The radial coordinate r may remain constant. For example, the radial coordinate r may be approximately 15 (assuming coordinates in pixel on an iPad Pro® with an origin in the center of the screen).

7. At step 370, the fixation cross is displayed again at the center of the screen. For example, the fixation cross may be displayed for 1 second.
8. At step 380, a fast counter clockwise spiral starts to be displayed. The counter clockwise spiral function is:
x=r·φ cos (φ), y=r·φ sin (φ).

Frame rates (in other words, steps of gradual rendering the spiral on the screen) may be adjusted such that φ increases between 0 and 65 and displays about 8 turns in 14 seconds. The radial coordinate r may remain constant. For example, the radial coordinate r may be approximately 15 (assuming coordinates in pixel on an iPad Pro® with an origin in the center of the screen). The spiral task method 300 ends after step 380.

It should be noted that the spirals described above are displayed gradually, within the time periods, starting from the center of the screen.

The following features (eye-movement metrics) may be determined based on a video of the user's face obtained during the spiral task (in other words, during the implementation of the spiral task method 300): average gaze position error relative to stimulus for each trial; deviation from stimulus path; angular velocity error; maximal angular velocity; measure of circularity of gaze pattern during each spiral revolution; and time during the trial at which error on position reaches a certain threshold.

In at least one embodiment, by monitoring eye movement during a task, the following metrics which characterize the person's ocular motion may be determined during the spiral task: frame to frame for velocities; at each frame for distances; latency is measured once); latency of motion onset; linear (tangential) velocity; angular velocity; linear (tangential) acceleration; angular acceleration; radial distance from current point of spiral; angular distance from current point of spiral; distance from spiral path which is the shortest distance between any point on the path and gaze (signed, whether inside or outside path); lag along the circular path—distance between spiral stimulus position and projection of gaze position onto circular path (signed, whether ahead or behind stimulus).

In at least one embodiment, the following features may be determined during the spiral task (per ⅒ of each of the two spirals, which corresponds to one spiral revolution of the target): latency of motion onset; average linear (tangential) velocity gain; average angular velocity gain; average linear (tangential) acceleration gain; average angular acceleration gain; SD linear (tangential) velocity gain; SD angular velocity gain; SD linear (tangential) acceleration gain; SD angular acceleration gain; CV linear (tangential) velocity gain; CV angular velocity gain; CV linear (tangential) acceleration gain; CV angular acceleration gain; maximum linear (tangential) velocity; maximum angular velocity; maximum linear (tangential) acceleration; maximum angular acceleration; average radial distance from current point of spiral; SD radial distance from current point of spiral; CV radial distance from current point of spiral; average angular distance from current point of spiral; SD angular distance from current point of spiral; CV angular distance from current point of spiral; average distance from spiral path which is the shortest distance between any point on the path and gaze (signed, whether inside or outside path); SD distance from spiral path; CV distance from spiral path; average lag along the circular path which is distance between spiral stimulus position and projection of the gaze position onto circular path (signed, whether ahead or behind stimulus); average absolute value of the lag along the circular path; SD lag along the circular path; CV lag along the circular path.

Examples of the on-screen instructions during the implementation of the spiral task method may be: "Look at the target that will appear in the centre of the screen." "As it moves around the screen, follow it as accurately as possible with your eyes until it stops, you may make some mistakes, and this is perfectly normal." The target may be a circle or a star symbol.

Figure 36:
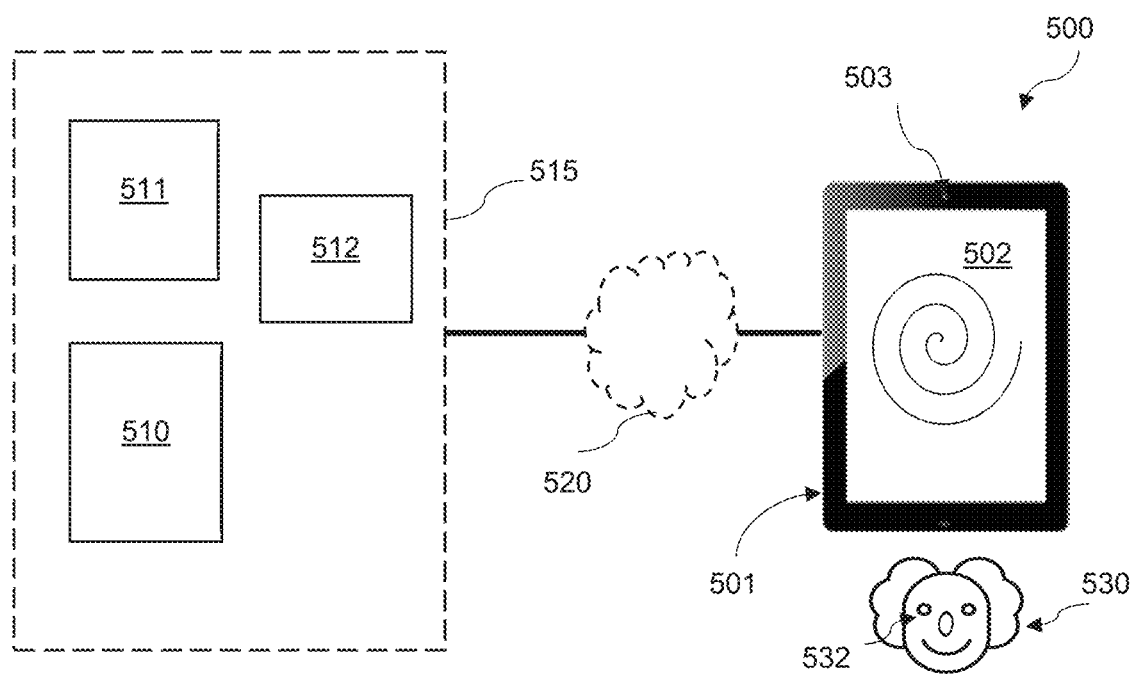
FIG. 36 is a block diagram of a system for detecting an eye gaze-pattern abnormality related to a neurological disease of a user, in accordance with one embodiment.

FIG. 36 shows a system 500 for detecting an eye gaze-pattern abnormality related to a neurological disease of a user 530, in accordance with one embodiment. The system 500 comprises: an electronic device 501 comprising a screen 502 for display and a camera 503 in proximity to the screen 502. The camera 503 is configured to film the user's face 532 while the user 530 is watching various stimulus videos displayed on the screen 502. The system 500 also comprises a memory 510 having a description of various sequences of targets of various tasks as described herein. The system 500 also has a processing unit 511 and a non-transitory computer readable medium 512 with computer executable instructions stored thereon. In some embodiments, the memory 510, the processing unit 511, and the non-transitory computer readable medium 512 are located on a server 515 and the electronic device 501 may communicate with the server via the network 520. In some other embodiments, the memory 510, the processing unit 511 and the non-transitory computer readable medium 512 are located in the electronic device 501.

3.1.8 Picture Free-Viewing Task
Task Parameters of the Picture Free-Viewing Task During the implementation of the picture free-viewing task, a random image is displayed for a certain period of time to the user. In at least one embodiment, several images are presented during a certain period of time. For example, there may be between 7 and 13, preferably about 10 random images displayed (presented to the user) one after another on the screen (for example, chosen from a set of pre-determined images). For example, the random image(s) may be displayed for 15 seconds.

The following features (eye-movement metrics) may be determined based on a video of the user's face obtained during the picture free-viewing task (in other words, during the implementation of the picture free-viewing task): total gaze distance travelled, numbers of saccades produced in the horizontal plane, characteristics of saccades produced in the horizontal plane (latency, amplitude, velocity), numbers of saccades produced in the vertical plane, characteristics of saccades produced in the vertical plane (latency, amplitude, velocity), area of the picture examined. These features may be collectively referred to as "free-viewing features".

In at least one embodiment, the following metrics are determined for each image: fixation, image coverage, saccades, fixation clusters.

For the fixation task, the following metrics characterizing ocular motion may be determined: total time in fixation; total number of fixation points. For the image coverage, the following metrics may be determined: total gaze distance travelled; percentage of the picture covered. With reference to saccades, the following metrics may be determined: total number of saccades; average amplitude of saccades; SD amplitude of saccades; CV amplitude of saccades; average saccade peak velocity/amplitude. With reference to fixation clusters, the following metrics may be determined: total number of fixation clusters; total time spent within fixation clusters; percentage of total number of saccades within fixation clusters; percentage of total number of saccades going from one cluster to another.

During the picture-free viewing task, the features (averaged across all images) are determined for fixation, image coverage, saccades, and fixation clusters. With regard to the fixation, the following features may be determined: average total time in fixation; average total number of fixation points. For the image coverage, the following features may be determined: average total gaze distance travelled; average percentage of the picture covered. With regards to the saccades, the following features are determined: average total number of saccades; average amplitude of saccades; average SD amplitude of saccades; average CV amplitude of saccades; average saccade peak velocity/amplitude. For the fixation clusters, the following features may be determined: average total number of fixation clusters; average total time spent within fixation clusters; average percentage of total number of saccades within fixation clusters; average percentage of total number of saccades going from one cluster to another.

On-screen instructions during the implementation of the picture free-viewing task may be, for example: "Please examine (observe) the following image".

3.1.9 Visuospatial IM Task

A visuospatial implicit memory (IM) task is an implicit memory task, and as such participants are not made aware that this is a memory task. The order of image presentation is the same across all individuals (i.e. a fixed predetermined order).

To implement the visuospatial IM task, the following steps are performed.

1. Following displaying of the first set of on-screen instructions (such as, for example, "Please enjoy the following set of images"), and once the participant has pressed "continue" (in other words, in response to a confirmation of readiness to proceed received from the user), a sequence of original images is presented. For example, if the number of original images is 10, then 5 images are modified to have an object added, and 5 images are modified to have an object removed. Each original image is displayed (presented) for a duration of several seconds (for example, 5 seconds each), with a white fixation cross appearing in the middle of the screen for, for example, one second between each image.

2. Second on-screen instructions are displayed, for example, for 20 seconds. For example, the following instructions are displayed: "Please wait while we load the following set of images. Please keep your head as still as possible and keep looking at the center of the screen."

3. A sequence of modified images (for example, a sequence of 10 modified images) are displayed for a duration of several seconds (for example, 5 seconds each), with a white fixation cross appearing in the middle of the screen for, for example, one second between each image. For example, each one of one portion of the original images (for example, there may be 5 original images) are modified to generate a first set of a first-type modified images, where each modified image has an object added, thus generating 5 modified images. Each one of other portion of the original images (for example, of the other 5 original images) is modified to generate a second set of a second-type modified image each with one object removed.

The modified images (first-type and second-type modified images) are presented (displayed) in the same order that the original images were presented in. In other words, each modified image is presented in the same order as the original image, from which the modified image has been generated. The modified images are the original images with either one or more objects added (for example, 5 images with an object(s) added) or one or more objects removed (for example, 5 images with an object(s) removed).

Figure 38A:
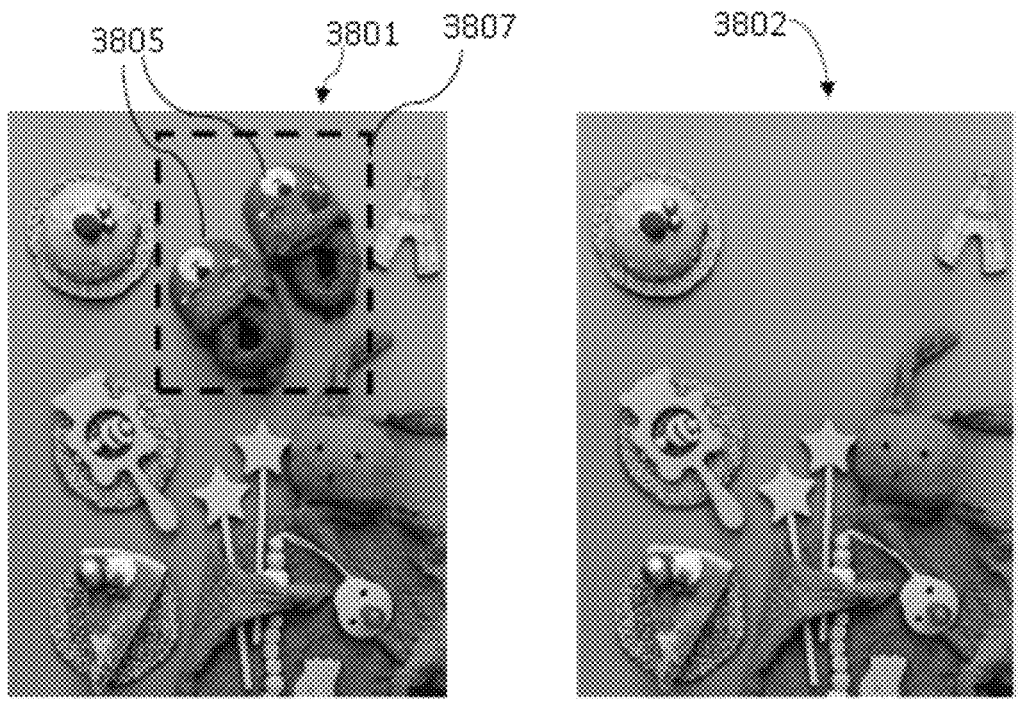
FIGS. 38A, 38B illustrate examples of original and modified images, in accordance with at least one embodiment of the present disclosure.
Figure 38B:
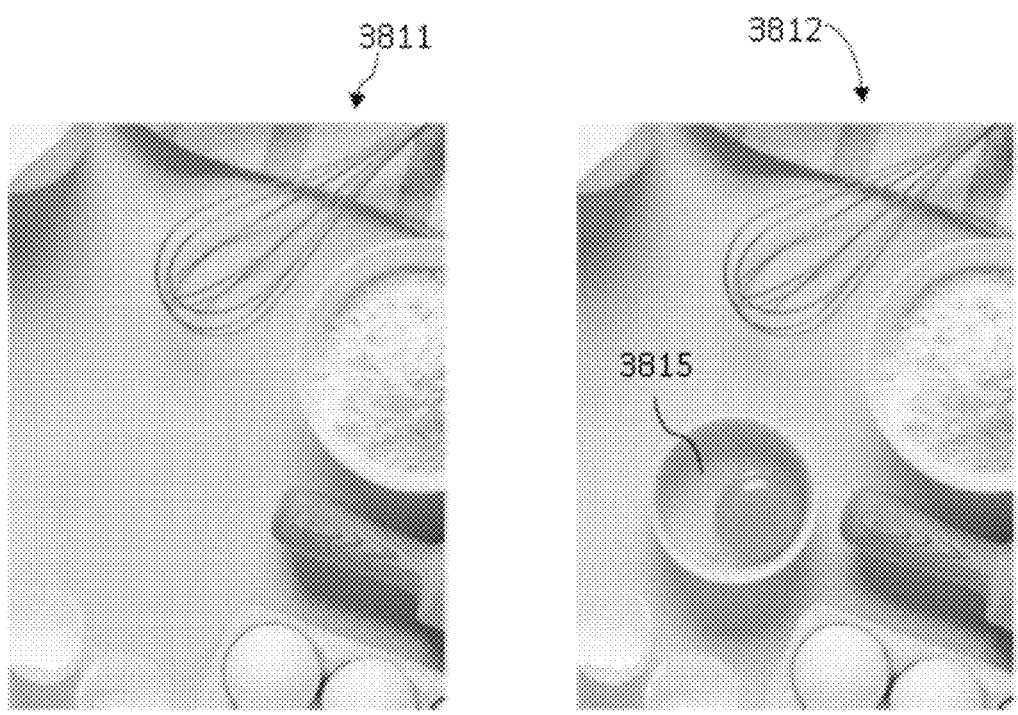

Referring now to FIGS. 38A, 38B where the examples of original and modified images are illustrated, in accordance with at least one embodiment of the present disclosure. FIG. 38A shows an original image 3801 and a modified image 3802. The modified image 3802, compared to the original image 3801 has two objects 3805 removed. For example, the image 3811 may be used as an original image, and the modified image 3812 has an object 3815 added to generate the modified image 3812. For example, the images may be pictures with various other objects too, which do not change between the original and modified image. The visuospatial implicit memory task may comprise displaying a sequence of original images and a sequence of modified images, each modified image corresponding to one original image and being displayed in the same order as the original image, each modified image having at least one object removed therefrom or added therein.

As referred to herein, ROI is a region of interest (when referred to the visuospatial IM task, the ROI may be also called an "interest-related region" or "attention-related region"), and each image has a corresponding ROI which is the modified portion of the image, expected to draw attention and therefore an ocular motion to be monitored. For example, the ROI's size and form may be pre-defined and may depend on the image.

Thus, the modified images are those that were presented in the second set of images. Modified-added images are images in the second set for which an object was added relative to its corresponding image in the first set (for example, images of second set may be: baking, cupcake, farm, gnome, hiking). Modified-removed images are images in the second set for which an object has been removed relative to its corresponding image in the first set (for example, images of second set: baby, cookies, desk, fish, helicopter).

For the visuospatial IM task, the following metrics (for each "modified" image) are determined: target ROI (which is an implicit memory evaluation) and total time within target ROI. Features (averaged across all "modified-added" and all "modified-removed" images) that may be determined are a target ROI (implicit memory evaluation) and average total time within target ROI. The set of features for the visuospatial IM task may comprise the target ROI (implicit memory evaluation) and the average total time within target ROI.

In at least one embodiment, ROI coordinates for the image sets are extracted. For example, and referring to FIG. 38A, a size of a box 3807 around the object(s) 3805 that is/are removed and the box's corners' coordinates are determined.

3.1.10 Tasks, Metrics and Features

The tasks as described herein are displayed in order to force the eyes of the user (patient) to follow the pre-determined trajectories (paths) of the targets on the screen (display). Thus, unless it is expressly described for a picture free-viewing task, the movements of eyes—which are tracked—are not spontaneous but rather forced or, in other word, induced. The targets on screen are expected to draw an ocular motion toward it and therefore the target's motion acts as an instruction for the task, where the task is therefore not a free video or succession of images with free eye motion to be monitored, but rather an instruction-driven task with specific on-screen elements that the person is expected to look at and be monitored for specific eye movement with respect to the specific on-screen elements (targets and the like).

In other words, each task has been elaborated specifically to force (encourage) the user's eyes to move in a pre-determined way (along a pre-determined path or trajectory) to determine specific metrics and features.

In particular, the system as described herein provides pre-defined (pre-determined) displaying sequence of the target, such as a pre-defined trajectory of the target. The target is displayed at pre-determined locations of the display and such a sequence of displaying the target to determine specific metrics and features. The user is invited to follow the target, and therefore a pre-determined trajectory of the target, and the eye gaze as a result of following the target (and therefore the pre-determined trajectory of the target) is measured and characterized.

Such induced motion of the eyes due to, for example, pro-saccade task is different from the saccade movement extracted from an uninduced, random motion of the eyes. As a result of such induced motion of the eyes, the metrics are extracted from each trial for each task in view of the ocular motion monitoring performed in real time on the subject taking part to the task. A plurality of task occurrences, or trials, can be performed, and according to an embodiment, the metrics are averaged per each trial, therefore across the duration of each (single) trial of the task, taken individually. Features are at a higher-level than metrics, and therefore, according to an embodiment, the features are averaged across (over) several trials of the same task, as exemplified in Table 4 below.

Some tasks, such as the fixation task, may have several phases, and a specific set of metrics and a specific set of features correspond to each phase of the task. For example, during the fixation task, a first set of features corresponds to intrusions and is also referred to herein as an intrusion set of features. Similarly, a first set of metrics corresponds to intrusions and is also referred to herein as an intrusion set of metrics. Another set of metrics and another set of features are determined (extracted) with regard to gaze drift and stability: a gaze-and-stability set of features and a gaze-and-stability set of metrics. The gaze-and-stability set of features and gaze-and-stability set of metrics comprise features and, respectively, metrics that correspond to drift and stability.

When the user stares at the tasks displayed on the screen, the user head does not need to be stabilized. Each task is pre-determined such that specific characteristics of the user's eyes may be extracted.

Table 4 below shows a non-exhaustive summary of various features that may be determined based on videos of the user's face that is recorded during the implementation of various tasks described herein, in accordance with various embodiments of the present disclosure.

TABLE 4

| Task | Feature |
|---|---|
| Fixation | Average gaze position |
| Fixation | Average gaze error |
| Fixation | Number of saccadic intrusions |
| Fixation | Presence of nystagmus |

TABLE 4-continued

| Task | Feature |
|---|---|
| Fixation | Direction of nystagmus |
| Fixation | Velocity of nystagmus |
| Pro-saccade | Saccade latency |
| Pro-saccade | H/V latency ratio |
| Pro-saccade | Peak saccade velocity |
| Pro-saccade | H/V peak velocity ratio |
| Pro-saccade | Saccade endpoint accuracy |
| Pro-saccade | Number of reversals in acceleration |
| Pro-saccade | Direction error rate |
| Anti-saccade | Arrow direction error rate |
| Anti-saccade | Saccade direction error rate |
| Anti-saccade | Correction rate |
| Anti-saccade | Saccade latency |
| Anti-saccade | Peak saccade velocity |
| Opto-kinetic nystagmus | Presence of nystagmus |
| Opto-kinetic nystagmus | Velocity of nystagmus, slow phase |
| Opto-kinetic nystagmus | Velocity of nystagmus, fast phase |
| Opto-kinetic nystagmus | Direction of nystagmus |
| Opto-kinetic nystagmus | Amplitude of nystagmus |
| Smooth Pursuit | Velocity gain |
| Smooth Pursuit | Average lag |
| Smooth Pursuit | Number of reversals in acceleration |
| Smooth Pursuit | Gaze direction error |
| Smooth Pursuit | Time to correct gaze direction |
| Spiral | Average gaze position error relative to stimulus for each trial |
| Spiral | Deviation from stimulus path |
| Spiral | Angular velocity error |
| | Maximal angular velocity |
| Spiral | Measure of circularity of gaze pattern during each spiral revolution |
| Spiral | Time during the trial at which error on position reaches a certain threshold |
| Picture Free-Viewing | Total gaze distance travelled |
| Picture Free-Viewing | Number of saccades produced in the horizontal plane |
| Picture Free-Viewing | Characteristics of saccades produced in the horizontal plane (latency, amplitude, velocity) |
| Picture Free-Viewing | Number of saccades produced in the vertical plane |
| Picture Free-Viewing | Characteristics of saccades produced in the vertical plane (latency, amplitude, velocity) |
| Picture Free-Viewing | Area of the picture examined |

In at least one embodiment, based on the video recorded during the implementation of the fixation task, the following features (also referred to herein collectively as "an eye fixation set of features") may be determined: average gaze position, average gaze error, number of saccadic intrusions, presence of nystagmus, direction of nystagmus, velocity of nystagmus.

In at least one embodiment, based on the video recorded during the implementation of the pro-saccade task, the following features (also referred to herein collectively as "a pro-saccade set of features") may be determined: saccade latency, H/V latency ratio, peak saccade velocity, H/V peak velocity ratio, saccade endpoint accuracy, number of reversals in acceleration, direction error rate.

In at least one embodiment, based on the video recorded during the implementation of the anti-saccade task, the following features (also referred to herein collectively as "an anti-saccade set of features") may be determined: arrow direction error rate, saccade direction error rate, correction rate, saccade latency, peak saccade velocity.

In at least one embodiment, based on the video recorded during the implementation of the optokinetic nystagmus task, the following features (also referred to herein collectively as "an optokinetic nystagmus set of features") may be determined: presence of nystagmus, velocity of nystagmus (slow phase), velocity of nystagmus (fast phase), direction of nystagmus, amplitude of nystagmus.

In at least one embodiment, based on the video recorded during the implementation of the smooth pursuit task, the following features (also referred to herein collectively as "a smooth pursuit set of features") may be determined: velocity gain, average lag, number of reversals in acceleration, gaze direction error, time to correct gaze direction.

In at least one embodiment, based on the video recorded during the implementation of the spiral task, the following features (also referred to herein collectively as "a spiral set of features") may be determined: average gaze position error relative to stimulus for each trial; deviation from stimulus path; angular velocity error; maximal angular velocity; measure of circularity of gaze pattern during each spiral revolution; and time during the trial at which error on position reaches a certain threshold.

In at least one embodiment, the features are determined by applying a trained machine learning algorithm to various frames of the video.

In at least one embodiment, after the features have been determined based on the videos (in other words, extracted from the videos), another trained machine learning algorithm may be applied to the features to detect various diseases and/or the progression of these diseases. For example, the progression of one or more diseases may be determined based on comparison of the videos captured during various time periods. In at least one embodiment, such comparison of the videos may be performed by a machine learning algorithm.

The eye gaze-pattern test may comprise more than one task. For example, the eye gaze-pattern test may comprise a combination of any two of the tasks described herein. For example, the eye gaze-pattern test may have any combination of the fixation task corresponding to the eye fixation set of features, the pro-saccade task corresponding to the pro-saccade set of features, the anti-saccade task corresponding to an anti-saccade set of features, and optokinetic nystagmus task corresponding to an optokinetic nystagmus set of features, the spiral test corresponding to the spiral set of features. As described above, each task comprises a sequence of targets that are displayed on the screen, and a set of features that corresponds to the task may be determined based on the video recorded while the sequence of targets of that task is being displayed. When two tasks are performed, the eye gaze-pattern abnormality may thus be detected based on the first set of features corresponding to the first task and the second set of features corresponding to the second task.

3.2 Dataset

The dataset collected from the tests described above includes much of the same data as collected and used for the purpose of gaze tracking, as described thoroughly above. The raw data may include full-face images collected during the tests, as well as the relevant meta-data, such as device type, screen size, screen resolution, device orientation, stimuli positions on the screen, etc.

The features extracted from the raw data may vary depending on the type of the expert model described herein below. In some cases, the features may be the same as the ones used for a gaze estimation system. Preferably, they are features such as those listed in Table 4, described below.

3.2.1 Synthetic Data

Given that in a biomedical setting, data is often scarce and its quality may be dubious, it may be possible to generate artificial data to train the models, either fully or in part. Given the realism that can be achieved by modern video game engines, videos of faces may be generated with very tight control over all parameters. The system may thus, for example, ensure that the virtual "participants" do in fact look precisely at the calibration targets.

This approach may also be used to develop and validate the algorithms. Indeed, with sufficient knowledge of the dynamics of the various abnormal eye movements which need to be detected, it may be possible to generate synthetic data displaying such eye movements with known parameters. This may make it possible to establish a ground truth against which the system may compare the feature extraction algorithms.

Similarly, in the context of gaze tracking, the evaluation of the models has so far been done using a holdout test set composed of real data, and so having the same quality issues as the training data, where no certainty may be given that a participant was indeed looking at a target. This may add an uncertainty to the ground truth, which by definition should have no uncertainty. Synthetic data may allow to substantially reduce such uncertainty.

3.2.2 Transfer Learning

As mentioned previously, data availability is often a problem in a biomedical setting. The training of deep learning however tends to require large amounts of high-quality data, often much more than may be reasonably acquired. To circumvent this problem, an approach known as transfer learning may be applied to the training pipeline.

During the training of an artificial neural network (ANN), for example, each layer is said to have a set of features that are iteratively modified to minimize the prediction error. The first layers of the model are said to have low-level features, that is "simple" features, while deeper layers combine the features of previous layers into more complex, high-level features.

The idea behind transfer learning is that a model trained to solve a problem somewhat similar to the problem being solved herein, learns low-level features that are nearly identical to the ones it would have learned on the actual problem. Once a model is thus trained, its low-level features may be frozen and the high-level features may be retrained to solve the main problem.

This is important since the deeper a network is, or the higher its capacity is, the more high-quality data is needed to train it. Thus the initial training may be done on an existing large dataset to allow the network to learn robust low-level features, and then retrain the much smaller network represented by the deeper layers of the network on the data directly relevant to the problem being solved.

Consider, for example, an unrelated scenario of training a network to classify images on whether they show an aardvark or a pangolin, which are animals having strong visual similarities and for which the number of existing images is smaller than for other animals. To do this robustly, several thousands of different images of each class would be needed, and it is dubious that such a dataset exists or could be easily generated. The network could instead be trained to differentiate between images of dogs and cats, which is a classic machine learning (ML) problem. The final layers of the trained network could then be retrained on the much smaller dataset of aardvark and pangolin pictures.

3.3 Expert Models

Three main problems may be identified and solved herein. Such three problems may be solved differently. The first two problems involve determining whether or not a pathology is present, and which specific pathology is present. These are not mutually exclusive; an expert system may be trained to determine if a pathology is present, and in the case of a positive answer, also determine which pathology is present.

It should be noted here that an "expert system" does not equate a machine learning model, as it may include a defined set of rules. Such a system may be a collection of models, trained using the same, or different, algorithms.

The third problem that can be addressed is the determination of the progress of an illness or condition. In this case, there is an assumption that a certain illness or condition is present (as previously determined), and one wishes to determine how "advanced" the illness or condition is, on a certain scale that can be discrete or continuous, numerical or categorical, according to the set of features that are seen, and determine if there is progression over time if this determination is repeated over time.

3.3.1 Types of Analysis

Two main types of analysis may be considered to address the tasks mentioned above. The first may be called spatial analysis. Here, the "space" is a mathematical space in which data points for a given problem exist. In this sense, a spatial analysis would infer conclusions from the point in the data space a particular data point occupies. This is the sort of analysis that is performed by the gaze tracking system, where a particular position in the input space is mapped to a particular set of gaze coordinates in the output space.

The second type of analysis may be called temporal analysis, in which conclusions are drawn not from the position in space from a particular data point, but from the positions of a sequence of data points. In this analysis, the order in which the input data is seen matters. An example of a problem for which this type of analysis is commonly used is natural language processing. In the present context, such an analysis may be used to monitor the progression of an illness or condition, as there may be valuable information in the history of the patient, not only in their current state.

3.4 Implementation

Several different approaches may be used to implement a diagnostics pipeline. Broadly speaking, the problem may be approached with eye tracking or gaze prediction as an intermediate step, or the problem may be solved directly using machine learning.

3.4.1 Gaze Tracking as an Intermediate

When using gaze tracking (preferably as described above) as an intermediate step, two machine learning systems work one on top of the other. A first system generates gaze predictions from the images or videos captured by the user's device. This may be optionally followed by a diagnostic feature extraction pipeline to extract the features discussed in section 3.1.

To generate the gaze predictions, a model or a set of models is needed to generate one set of (X,Y) gaze coordinates for each eye. While the method for gaze tracking described above only outputs one set of gaze coordinates, that model may be retrained to output one set of (X,Y) gaze coordinates for each eye and may be usable for the purpose of the detection of eye gaze-pattern abnormalities.

More specifically, these can be general models similar to the ones used in the method for gaze tracking described above, that may then be calibrated using the data from the calibration task described in section 3.1.1, or they can model similar to the ones used in reference to FIG. 6 as described above that are trained exclusively on the calibration data. Both approaches have been investigated, and both offer results that the other may not produce. It is thus contemplated that the pipeline for the detection of eye gaze-pattern abnormalities uses both systems in a complementary way.

Regardless of how it is accomplished, once gaze position signals are obtained, they may be used as input vectors to a machine learning system that learns to detect the presence of a neurological condition, or to determine the progression of a neurological condition. Here, the ability to perform model introspection is paramount, as it is not only important to reliably diagnose or track conditions, but also, and perhaps as importantly, to determine which particular features of eye movements led to such determinations.

This is why it may initially be preferable to instead extract from the gaze signals a set of predetermined features, such as detailed in section 3.1. These predetermined features may be used to perform some initial statistical analysis in an effort to refine the data collection protocol and to eliminate features that are determined to be irrelevant to characterize eye gaze-patterns and detect abnormalities. The remaining features may then be used as individual values of an input vector for a machine learning algorithm. This arrangement makes it much easier to determine the predictive power of each individual input.

Another advantage of this approach is that the extraction of these predetermined features would likely reduce the complexity of the models that would then need to be trained to identify or track a condition from those features. The features such as those listed in Table 4 are therefore intermediate information derived from the raw data (images or frames of the video) which are used to simplify the following steps of analysis, which can use such predetermined features as an input to characterize eye gaze-patterns and detect abnormalities.

3.4.2 Direct Prediction

In a direct prediction method, models are trained directly on the videos captured by the camera. Some minimal processing may be performed, such as image enhancement or segmentation, but the task of extracting diagnostics features from the videos is left entirely to the machine learning algorithm when using the direct prediction method.

As discussed in the previous section, it is important to understand which features drive the decisions of the machine learning models to be able to establish a link between a diagnosis or condition assessment, and clinically observable features. This would be made more difficult by the need to perform model introspection to determine which features a model has selected, and by the fact that those features may not easily be interpreted by a human observer. Indeed, no guarantee exists that the features selected by the algorithm are what a human might classically understand to be features.

Conversely, it may well be that classic clinical features, that were designed by humans, with human heuristics and biases, to be interpreted by humans, are not ideally suited to solving the problems described herein. A machine learning algorithm may identify more information-rich features that would then, if possible, need to be interpreted in human terms.

Finally, the direct prediction method is likely to be much more time- and resource-intensive than another approach which uses gaze tracking as an intermediate. The diagnostics models may indeed need to be much more complex as their inputs are much more complex. This in turn means that training times may be increased for each problem, and so would the data requirements for training. This last issue may be addressed by using transfer learning, as discussed in section 3.2.2.

In at least one embodiment, the direct prediction method is used on its own. In at least one another embodiment, gaze tracking is used initially as an intermediate to obtain faster results.

3.4.3 Feature Extraction

This section describes the methods implemented to extract diagnostic features from the two gaze signals, one for each eye, that would be extracted by a system as described in section 3.4.1. The features mentioned in section 3.1 are grouped here by the similarity of the algorithms that would be used to extract those features, rather than by task.

3.4.3.1 Artifact Detection

An important artifact that needs to be detected prior to model training or diagnostics feature extraction is the times during which one or both eyes are closed. Indeed, the inclusion of such frames in the training data for any algorithm that relies on gaze estimation would be considered as noise, as no gaze information may be obtained at those times.

Identifying when the eyes are closed is a problem that can be approached in many different ways. Given a large enough amount of annotated data, perhaps the simplest way to detect closed eyes would be to train a machine learning model, as there are large visual differences between an open eye and a closed eye that make the task ideally suited to machine learning.

When the blinks or other artifacts are detected, the corresponding frames (images) in the video can be removed from the treatment as they are not useful for feature extraction. Alternatively, the blinks may be among the features of interest to be extracted, as various disease states can affect blink rate (especially Parkinson's and Progressive supranuclear palsy). The treatment (removal of frames comprising blinks as being an artifact or detection of blinks as a feature) depends on the application of the method.

In the absence of such data, a facial feature extraction model, models which are readily available from various sources, may be used to extract some outline of the eyelids. From this, a measurement called the Eye Aspect Ratio (EAR) may be computed to represent how open the eye is. Based on the EAR, the system may determine whether an eye is open or closed.

It should be noted that when this approach was tried in the context of real-life data collected from tablets, even with some additional steps to increase robustness, the EAR calculation yielded poor results. Some additional refinements may be implemented, so while method may be implemented by the system, but other methods are described below.

A more robust method detects blinks by considering sequences of frames, not individual frames. This method works with videos. This method is based on the assumption that, given an image that is cropped from a face to contain only the eye and the surrounding eyelid, the colour of the image will experience two sudden shifts when a blink occurs, due to the sclera being quickly and completely obstructed from view for a few hundred milliseconds.

Based on a video of a person's face, the system first extracts only one eye, always the same, for each frame, thus generating a video of one of that person's eyes. The system then transforms this video into a single image, where each vertical line of the image is the greyscale histogram of a single frame. Given the colour shift discussed earlier, every time the eye opens or closes, a vertical edge appears on the composite histogram image. The system then detects and pairs these edges to detect blinks. This method works reasonably well. This method may also be used in combination with other methods to improve robustness.

3.4.3.2 Endpoint Accuracy

Endpoint accuracy is the average accuracy of the gaze for a single eye during fixation. This means that when a user is asked to fixate a target at a particular location on the device's screen, such as a tablet's screen using the tablet's built-in camera or a smartphone screen using the smartphone's built-in camera, the saccade that brings the gaze to the target must be ignored. Otherwise, the accuracy is simply given by taking the average value of all the gaze predictions generated during the fixation. Further information about the stability of the fixation may be generated based on the standard deviation of the gaze predictions.

3.4.3.3 Metrology of Saccades

Saccades are rapid eye movements made to shift the fovea to objects of visual interest. The defining characteristics of saccades include latency, peak velocity and accuracy. Latency is defined as the amount of time, normally between 150 and 400 milliseconds, between the presentation of a stimulus and the start of the movement of the eye. Peak velocity is the maximum angular velocity reached by the eyeball during the saccade, normally expressed in degrees per second (deg/sec).

Accuracy is the difference between the target position and the position of the eyeball at the end of the saccade. This is different from the endpoint accuracy described in the previous section, as hypo- and hypermetric saccades may occur that may be followed by additional corrective saccades. It is thus possible for a person to have saccadic inaccuracy but near perfect endpoint accuracy.

Latency and peak velocity may be determined based on fitting a parametric model of saccades to a single saccadic signal from gaze data, such as the gaze data collected as described above in section 2. As the parametric model of saccades model is meant to fit positional data expressed in degrees, the system needs to convert the (X,Y) coordinates determined by the method for gaze tracking described above into the angle of the user's eyeballs relative to the camera.

To do this, the system may use simple trigonometry to determine the angle, given the position of the gaze on-screen and the distance between the user and the camera. The distance between the user and the camera may be determined (estimated) by relating anthropometric data of the average dimensions of the face to the set facial feature coordinates. Such estimate may be accurate within 5%.

By fitting the parametric model of saccades to a saccadic signal the system determines a saccade latency. Based on the saccade latency, the system may calculate the peak velocity and amplitude of the saccade, which allows to determine the accuracy of the saccade. By comparing the signs of the amplitude of the actual saccade to the sign of the amplitude of the expected saccade, the system also determines if the saccade was performed in the correct direction.

It has been assumed so far that a single saccade ever occurs per stimulus, as the parametric model allows to measure saccades, not detect them. This is not always the case, as a saccade in the wrong direction may be followed by a corrective saccade, as can be hypo- or hyper-metric saccades. When using infrared eye tracking, saccades are normally detected by thresholding the signal on amplitude, velocity and acceleration, with a saccade being detected when all three signals exceed a certain value. These values tend to vary from eye tracker to eye tracker.

3.4.3.4 Saccadic Intrusions

Saccadic intrusions are irregular episodic occurrences of a series of two or more fast eye movements. Advantageously, those may be measured by measuring saccades.

3.4.3.5 Metrology of Nystagmus

Nystagmus is characterized by a quasi-periodic oscillation of the eyes, either during fixation or during smooth pursuit. Various types of nystagmus can be defined based on physiological characteristics such as the direction of motion or accompanying motor oscillations, or based on the shape of the waveform of eye angle over time.

For the purposes of the diagnostics feature extraction pipeline, the system may focus on the shape of the waveform of the eye angle over time. The system further decomposes this into horizontal and vertical dimensions to be processed by the same algorithms, but independently.

This yields four distinct types of waveforms to be identified and measured: pendular nystagmus, which presents as a sinusoidal waveform, and jerk nystagmus, where the eye moves quickly in one direction (the fast phase) and more slowly back in the other direction (the slow phase). Jerk nystagmus may further be distinguished based on the shape of the slow phase: constant velocity, exponentially decreasing velocity or exponentially increasing velocity.

The detection of nystagmus in a gaze signal may be achieved robustly by detecting the presence of a spike within a certain frequency range in the power spectral density of the gaze signal. This spike occurs in different ranges depending on the nystagmus, which may serve as a first indication of the type of nystagmus present, as is the fact that jerk nystagmus shows harmonics while pendular nystagmus does not. The peak frequency of the spike can be used directly as the measure of the frequency of the nystagmus. Filtering the original gaze signal using a bandpass filter around this fundamental frequency allows a straightforward measurement of the amplitude of the nystagmus.

In the case of jerk nystagmus, the system measures the direction of the nystagmus, defined by the direction in which the eyes move during the fast phase, as well as the velocity of the eyes during the fast and slow phases. Since the eyes never have a perfectly constant velocity profile during motion, even for a constant velocity jerk nystagmus, the velocity of each phase may be defined as the total angular travel over time, so the average angular velocity.

To measure the jerk nystagmus, the system may find the peaks and troughs of a gaze signal filtered to only leave the nystagmus. The system may then segment the signal from peak to trough and trough to peak. By grouping these segments into a "short" group and a "long" group, the system then may effectively separate the fast phases from the slow phases. The system may then average the velocities over each group to get the velocity of each phase of the nystagmus. Based on the angle of the fast phase velocity vector, the direction of the nystagmus is determined.

Finally, to differentiate which type of jerk nystagmus is present, the system may fit a linear function and an exponential function to the slow phase to the slow phase isolates. The best fit between the two differentiates constant velocity from exponential velocity. The sign of the exponent, in the case of exponentially changing nystagmus, differentiates between exponentially increasing velocity and exponentially decreasing velocity.

3.4.3.6 Metrology of a Smooth Pursuit

A smooth pursuit is a type of eye movement during which, in a normal person, the eyeball smoothly rotates to track a target. When smooth pursuit is initiated, a saccadic movement occurs to allow gaze to catch up to the target, after which the eye attempts to smoothly track the target. In the event of a change in the target's velocity, the eye's motor plant needs some time to adapt, during which pursuit continues in the original direction before performing the aforementioned saccade to finally resume pursuit.

To measure and analyze the smooth pursuit, the system may measure the average lag of the gaze behind the target, the velocity gain of the gaze, which is the ratio between the velocity of the target and the velocity of the gaze, as well as the time it takes to correct the gaze velocity vector after a change in the target's velocity vector.

This task consists of several segments during which the target moves in one direction at a constant velocity and at the end of which it changes direction and possibly velocity. The same analysis may be applied to each segment. The analysis of a single segment is described herein below.

Ignoring the initial saccadic motion, the lag between the gaze and the target may be taken as the mean absolute error between the gaze coordinates and the target coordinates. Similarly, the velocity gain may be determined based on the ratio between the average velocity of the gaze signal and the velocity of the target.

To determine time to "correction", the system detects the saccade-like corrective motion (i.e., the correction) and the time before it occurs. To detect the saccade-like corrective motion, a saccade detection algorithm may be used, with some possible refinements to account for slight differences between an actual saccade and this particular signal. Given that this corrective movement may be detected robustly, the time to correction may be determined based on the time of occurrence of the saccade-like corrective motion since the start of the segment.

3.4.4. Method Embodiments Using Machine Learning

Figure 37A:
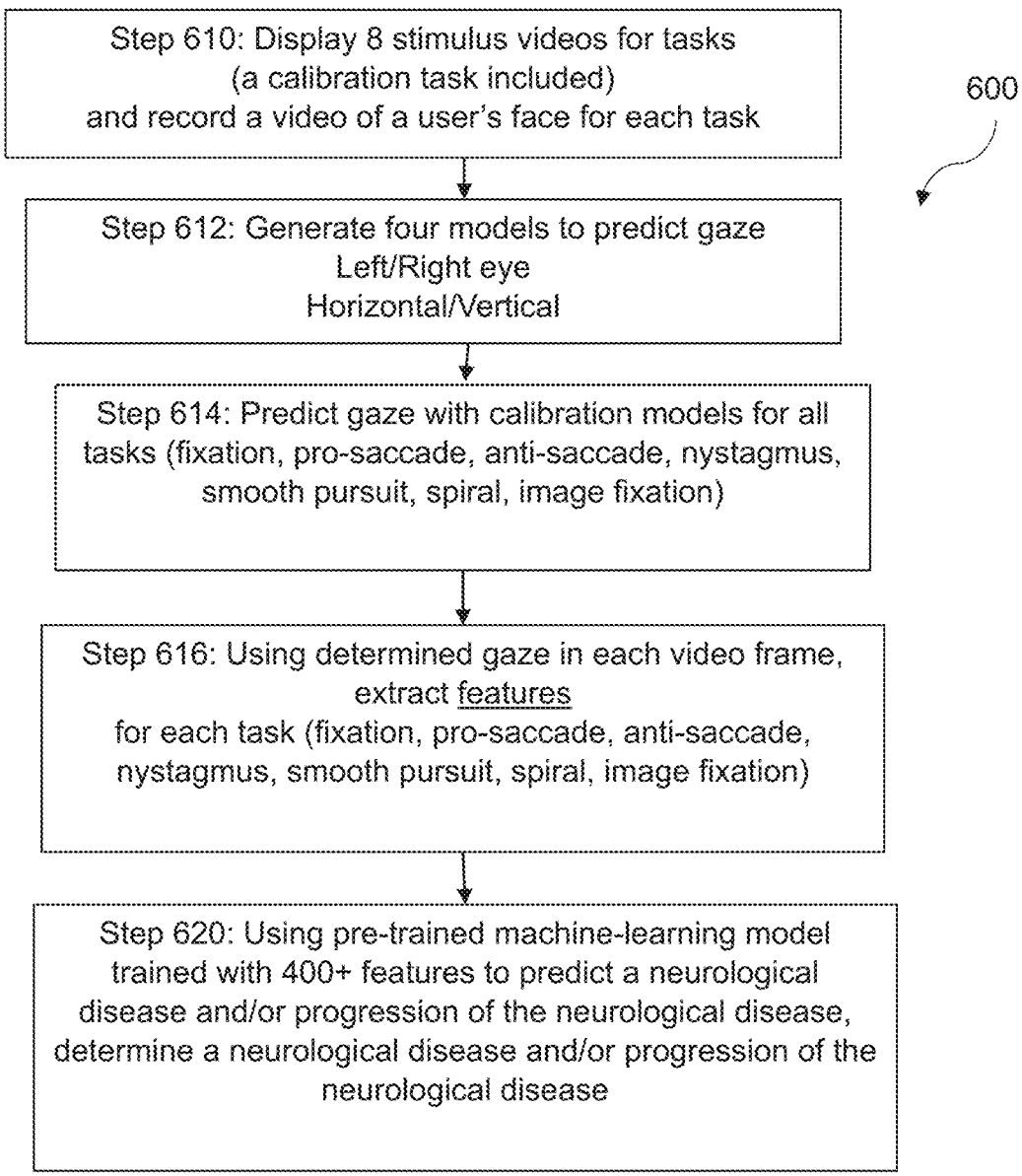
FIG. 37A is a flowchart illustrating a method for detecting a neurological disease and an eye gaze-pattern abnormality related to a neurological disease, in accordance with an embodiment of the present disclosure.

FIG. 37A depicts a method 600 for detecting a neurological disease and an eye gaze-pattern abnormality related to a neurological disease, in accordance with an embodiment of the present disclosure. At step 610, stimulus videos for various tasks described herein are displayed. The stimulus videos correspond to a calibration task, which is used to enhance precision in gaze pattern analysis, and a combination of all or some of the following tasks: a fixation task, a pro-saccade task, an anti-saccade task, a nystagmus task, a smooth pursuit task, a spiral task, and an image fixation task. Each of the stimulus videos comprises a sequence of targets displayed on the screen as described herein above for each task.

At step 612, 4 machine learning models for the prediction of an eye-gaze are generated. The 4 machine learning models are related to the left eye movement, the right eye movement, the horizontal gaze coordinate, and the vertical gaze coordinate.

At step 614, machine learning algorithm is used to generate gaze predictions for each task using the machine learning models. Such gaze predictions are made based on the videos of the user's face recorded for each task. The machine learning algorithm uses data collected while performing various tasks, such as a fixation task, a pro-saccade task, an anti-saccade task, a nystagmus task, a smooth pursuit task, a spiral task, and an image fixation task.

At step 616, using determined gaze in each video frame, features for each task (such as the fixation task, the pro-saccade task, the anti-saccade task, the nystagmus task, the smooth pursuit task, the spiral task, and the image fixation task) are extracted. The extracted features may be different for each task (see, for example, Table 4).

At step 620, using pre-trained machine learning model, a neurological disease and/or a progression of the neurological disease and/or the eye gaze-pattern abnormality (and/or its progression) related to the neurological disease is determined. Such pre-trained machine learning model may be trained with, for example, more than 400 features to predict a neurological disease, its progression, and/or eye gaze-pattern abnormality and the progression of the eye gaze-pattern abnormality related to the neurological disease. At step 620, the neurological disease is detected based on the features determined for each task at step 616. The state and/or progression of the neurological disease, eye gaze-pattern abnormality related to the neurological disease, and the progression of the eye gaze-pattern abnormality may also be determined.

Figure 37B:
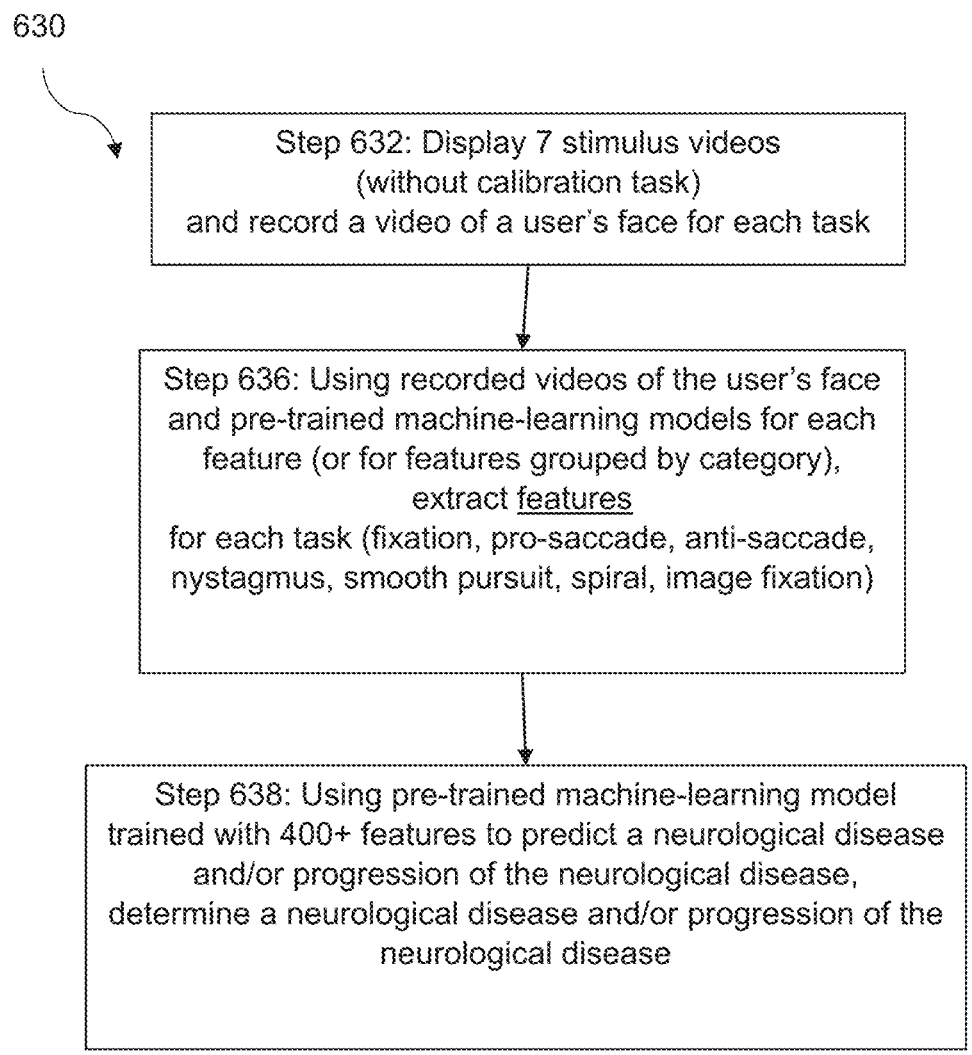
FIG. 37B is a flowchart illustrating a method for detecting a neurological disease and an eye gaze-pattern abnormality related to a neurological disease, in accordance with another embodiment of the present disclosure.

FIG. 37B depicts a method 630 for detecting a neurological disease and an eye gaze-pattern abnormality related to a neurological disease, in accordance with another embodiment of the present disclosure which does not require any calibration. At step 632, stimulus videos for various tasks described herein are displayed, except for the calibration task which can be avoided, advantageously in terms of user experience and time required to run the method. The stimulus videos correspond to a combination of all or some of the following tasks: a fixation task, a pro-saccade task, an anti-saccade task, a nystagmus task, a smooth pursuit task, a spiral task, and an image fixation task. Each of the stimulus videos comprises a sequence of targets displayed on the screen as described herein above for each task.

At step 636, using recorded videos of the user's face and pre-trained machine learning models for each feature of a set of features (or for features grouped by category), features are extracted (determined) for each task. The features used by the pre-trained machine learning model are a combination of, or one of: a number of reversals in acceleration, a number of saccadic intrusions, an amplitude of nystagmus, an angular velocity error, an arrow direction error rate, an average deviation error, an average gaze position, an average gaze position error, an average lag, a correction rate, a direction error rate, a direction of nystagmus, a gaze direction error, horizontal-to-vertical (H/V) latency ratio, H/V peak velocity ratio, maximal angular velocity, measure of circularity of gaze pattern during each spiral revolution, a peak saccade velocity, the presence of nystagmus, a saccade direction error rate, a saccade endpoint accuracy, a saccade latency, time error threshold (TBD), time to correct gaze direction, a velocity gain, and a velocity of nystagmus. It at least one embodiment, a combination of some of the features listed herein may be used by the pre-trained machine learning model. In the embodiment of method 630, the features are extracted directly, without intermediate gaze prediction.

Step 638 is similar to step 620 of method 600. At step 638, using a pre-trained machine learning model trained with more than 400 features to predict a neurological disease and/or progression of the neurological disease, the neurological disease and the progression of the neurological disease is determined. In at least one embodiment, the machine learning model is trained to predict the eye gaze-pattern abnormality related to the neurological disease based various features, and thus may determine the eye gaze-pattern abnormality related to the neurological disease. Progression of the eye gaze-pattern abnormality related to the neurological disease may also be determined. In some embodiments, determining the eye gaze-pattern abnormality related to the neurological disease comprises determining the neurological disease.

Figure 37C:
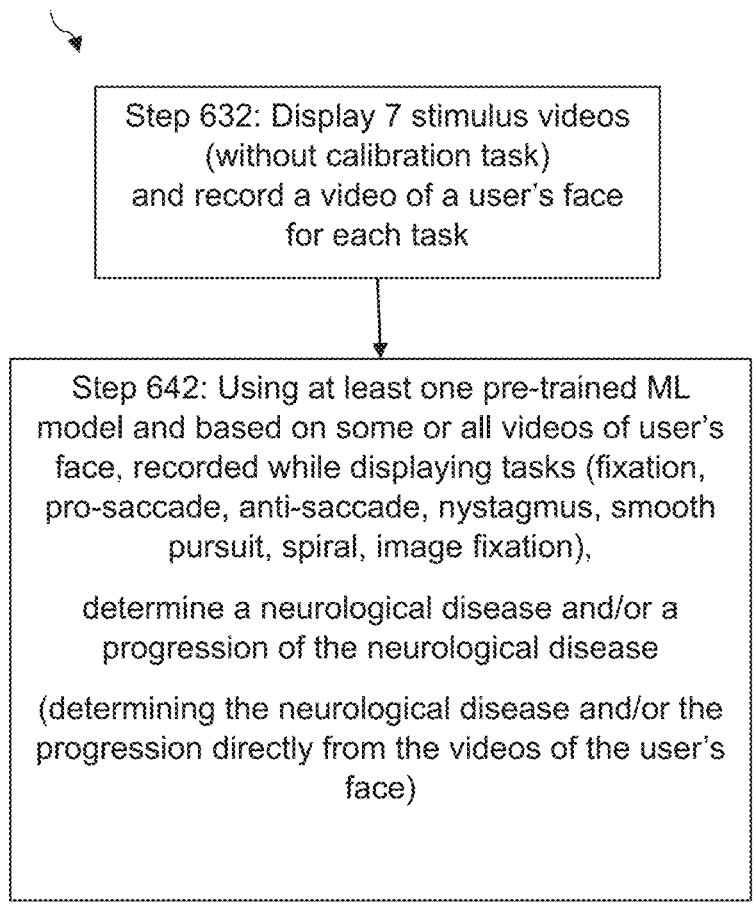
FIG. 37C is a flowchart illustrating a method for detecting a neurological disease and an eye gaze-pattern abnormality related to a neurological disease, in accordance with another embodiment of the present disclosure.

Referring now to FIG. 37C, where a method 640 for detecting a neurological disease and an eye gaze-pattern abnormality related to a neurological disease, in accordance with another embodiment of the present disclosure which also does not require any calibration. Step 632 is the same as in method 640 of FIG. 37B. At step 642, using at least one pre-trained machine learning model and based on some or all videos of the user's face, recorded while displaying tasks (fixation, pro-saccade, anti-saccade, nystagmus, smooth pursuit, spiral, image fixation), a neurological disease, and/or a state and/or progression of the neurological disease, and/or eye gaze-pattern abnormality and/or a state and/or progression of the eye gaze-pattern abnormality related to the neurological disease are determined. In method 640, the neurological disease, the neurological disease, the state and/or progression of the neurological disease, eye gaze-pattern abnormality related to the neurological disease, and the progression of the eye gaze-pattern abnormality are determined directly from the recorded videos of the user's face.

The methods 600, 630, 640 may determine one or more neurological diseases and eye gaze-pattern abnormalities related to the neurological diseases. For example, as many as twelve diseases may be determined.

In at least one embodiment, the methods as described herein may be embodied as a computer program product. In at least one embodiment, the system described herein comprises a non-transitory computer readable medium which stores computer executable instructions thereon, and which, when executed by the processing unit, cause the processing unit to perform steps of the methods described herein.

4. Discussion on the Abnormalities that May be Detected by the System and the Method Described Herein Saccades—Saccadic eye movements, when looking at the plot of the angle of the eye over time, describe a roughly sigmoid curve. During the movement, the peak angular velocity of the eyeball is reached at the midpoint of the sigmoid. This peak velocity is dependent on the amplitude of the saccade and on the person executing the movement. Thus, a person's saccadic plant can be expressed by their "main sequence", which is a decreasing exponential curve that describes the relationship between the amplitude of a saccade and the peak velocity of that saccade. This relationship is given by the following equation:

$$V_p(A; \eta, c) = \eta(1 - e^{-A/c}),$$

where $\eta$ is the maximum possible eyeball angular velocity given a saccade of infinite amplitude; and $c$ is the growth rate of the velocity relative to amplitude.

For a saccade starting at time t=0 and with an initial eyeball angle of 0 degree, the dynamics of a saccadic movement are parameterized by the following equations:

$$s(t; \eta, c, \tau) = c \cdot f[\eta t/c] - c \cdot f[\eta(t-\tau)/c],$$

where:

$$f(t) = t + 0.25 e^{-2t},$$
$$t \geq 0$$
$$f(t) = 0.25 e^{2t},$$
$$t \leq 0.$$

If we want to incorporate saccadic latency (to) and initial eyeball angle (so) into the model, the full model is expressed as:

$$S(t; \eta, c, \tau, t_0, s_0) = s(t - t_0, \eta, c, \tau) - s_0.$$

To generate a saccadic plant for a fictional person, and to then generate saccades using this plant, the $\eta$, c and $t_0$ parameters can be sampled from the following ranges:

$$\eta \in [500, 800],$$

$$c \in [12, 33],$$

$$t_0 \in [0.15, 0.25], \text{ for a healthy individual,}$$

$$t_0 \in [0.25, 0.45], \text{ for an unhealthy individual,}$$

The $s_0$ parameter is simply the angle of the eyeball at the start of the saccade, and given a saccadic amplitude A, the $\tau$ parameter is given by:

$$\tau = A/\eta.$$

This model should be applied to the horizontal and vertical components of saccades individually to generate a complete movement, if the movement is not purely horizontal or vertical.

Nystagmus

Nystagmus is an involuntary, rapid, rhythmic, oscillatory eye movement with at least one slow phase. Jerk nystagmus is nystagmus with a slow phase and a fast phase, while pendular nystagmus is nystagmus with only slow phases.

Nystagmus may be continuous or episodic. Episodes of nystagmus may occur spontaneously, may occur in only certain gaze positions or viewing conditions, or may be triggered by particular manoeuvres. As there are only four types of nystagmus waveforms but many more types of nystagmus proper, some of which is physiological (normal) and some pathological, information about the circumstances in which nystagmus occurs is crucial to determining the type of nystagmus that is observed.

Figure 28:
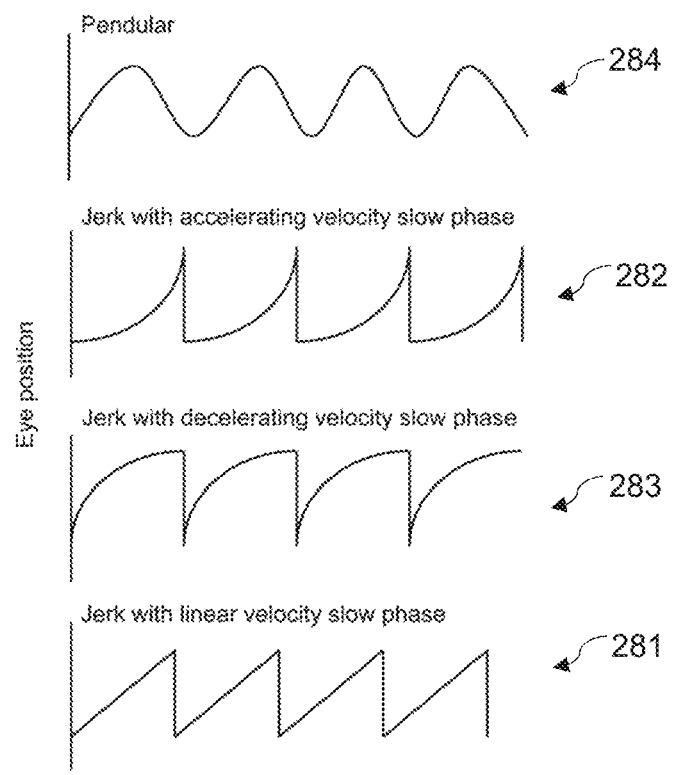
FIG. 28 is a collection of graphs illustrating the four characteristic nystagmus waveforms, according to an embodiment.
Figure 29:
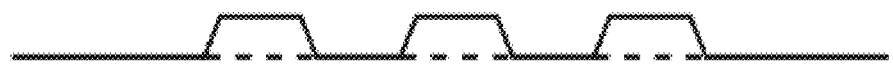
FIG. 29 is a graph illustrating a typical angular variation vs. time for a saccadic movement, according to an embodiment.

FIG. 28 shows the four characteristic nystagmus waveforms.

1. Constant velocity waveform 281 depicted in FIG. 28 is characterized by a constant velocity drift of the gaze position away from target, followed by a corrective saccade. Such constant velocity waveform 281 may correspond to the optokinetic nystagmus.
2. Increasing velocity waveform 282 is characterized by a drift of the gaze position away from target with an exponentially increasing speed during the slow phase, followed by a corrective saccade. Such increasing velocity waveform 282 may correspond to the congenital motor nystagmus.
3. Decreasing velocity waveform 283 is characterized by a drift of the gaze position away from target with an exponentially decreasing speed during the slow phase, followed by a corrective saccade. Such decreasing velocity waveform 283 may correspond to the gaze evoked nystagmus.
4. Pendular nystagmus is characterized by a sinusoidal waveform 284 that can affect one or both eyes, in different amounts. It is often limited to the horizontal plane, but some pathologies can cause vertical pendular nystagmus. As it is a sinusoidal waveform, there is no slow phase or fast phase in pendular nystagmus.

Types of Nystagmus: APN and GEN

Acquired Pendular Nystagmus (APN)

In Multiple-Sclerosis (MS)—associated APN, the oscillation is normally of a frequency in the range $f_0 \in [2, 6]$ Hz, with a maximal amplitude of about 3 degrees, though this can be much less. The amplitude of the oscillation obeys Alexander's Law, which states that the amplitude of the oscillation is proportional to the eccentricity of the gaze position. Furthermore, APN disappears during a blink or a saccade, and progressively reappears after the end of the blink or saccade, over the course of several hundred milliseconds. The oscillation is also phase-shifted by an amount proportional to the duration of the neural pulse that caused the blink or saccade. Thus, in the case of a saccade, the phase shift of the oscillation is proportional to the amplitude of the saccade.

Gaze-Evoked Nystagmus (GEN)

GEN is a jerk-like movement characterized by slow phase and fast phase movements. During eccentric gaze, the eyes rotate back towards the primary position with an exponentially decreasing angular velocity. This is followed by a corrective saccade to bring gaze back towards the eccentric gaze position. Thus, the fast phase is in the direction of the eccentric position, while the slow phase is towards the primary position.

The amplitude and frequency of this movement follows Alexander's Law, which states that the frequency and amplitude of the nystagmus is proportional to the amplitude of the eccentric gaze. The amplitude of pathologic GEN is nearly always greater than 4 degrees. Additionally, pathologic GEN is sustained (lasting more than 20-30 seconds) and may be asymmetric.

GEN is a quasiperiodic signal, in that the average time between each jerk is constant for a given person for a given eccentric gaze position, but it changes from jerk to jerk. Similarly, the amplitude of the jerk changes from jerk to jerk.

GEN in multiple sclerosis: In Multiple Sclerosis patients, GEN is often caused by a lesion to the medial longitudinal fasciculus (MLF), which in turn causes internuclear ophtalmoplegia (INO).

INO is a lesion of the medial longitudinal fasciculus (MLF), which is a structure in the brain that controls the conjugate movements of the eyes in one direction. As such, there are two MLFs, one that controls left conjugate movements and one that controls right conjugate movements. INO can affect one of the MLFs (unilateral INO), or both (bilateral INO).

INO causes a weakness or even failure in adduction of the affected eye in contralateral gaze, and nystagmus of the abducting eye. For example, in right INO, when gazing to the left, the right eye does not reach the fixation target, while the left eye exhibits left-beating nystagmus (fast phase to the left). Unilateral INO is most often associated with ischemia, while bilateral INO is generally seen in MS patients. Thus, in an MS patient, a left gaze would cause the right eye to adduct move minimally to the left, while the left eye would reach the fixation target but exhibit nystagmus.

Optokinetic Nystagmus (OKN)

Nystagmus induced by a moving visual field, or by self-rotation in a static visual field (turning in place with eyes open). This type of eye movement is characterized by a slow phase in the direction movement of the visual field, followed by a saccade in the direction opposite that of the visual field. In true OKN, the oscillations will typically be 3-4 degrees in amplitude, and 2-3 Hz in frequency.

The slow phase is of linear velocity, and, in healthy individuals, will be symmetrical. True optokinetic nystagmus can be approximated by a striped visual field enclosing the person and rotating about the person. By contrast, the use of an optokinetic drum primarily recruits the smooth pursuit system.

In at least one embodiment, nystagmus may be detected based on a spectral analysis. For example, a Fourier transform of the angular movements can be applied on particular frequencies or frequency intervals and can be determined to correlate with nystagmus.

Saccadic Intrusions—Saccadic intrusions are involuntary conjugate saccades that interrupt fixation. Several types of saccadic intrusions exist including square wave jerks (SWJ), square wave pulses (SWP), macrosaccadic oscillations, saccadic pulses, ocular flutter, and opsoclonus. A few intermittent, random, saccadic intrusions (especially SWJ) may be seen in healthy patients but can also be seen as a nonspecific finding in patients with multiple neurologic conditions. More persistent saccadic intrusions (e.g., ocular flutter or opsoclonus) however are pathologic and require evaluation. Treatment may be considered if patients are symptomatic and is dependent on the underlying etiology.

Square Wave Jerks (SWJ)—Square wave jerks are pairs of involuntary saccades that take the eyes away from target, then back to target after a 200-400 ms intersaccadic interval. SWJs can occur in isolation in healthy individuals at a rate of up to 16 per minute, but can also occur in clusters. In the latter case, the intersaccadic interval of 200-400 ms is respected between occurrences of SWJs. An example of angular movement over time is shown in FIG. 33. For example, square wave jerks may be determined by detecting saccades and by then finding pairs of saccades of similar amplitude but opposite directions, which occur with an intersaccadic interval that falls within a specific range.

Figure 30:
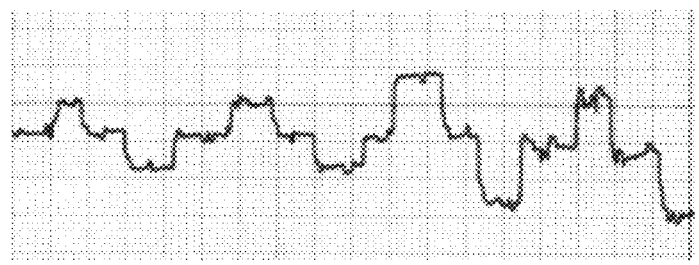
FIG. 30 is a graph illustrating an empirical angular variation vs. time for a saccadic movement, according to an embodiment.

As can be seen in FIG. 30, which is an actual recording of SWJ, individual occurrences do not have to be to the same side of the target, but can alternate directions instead. SWJs typically have an amplitude of 0.5-5 degrees. Greater angular amplitudes are possible, but those are classified as macro square wave jerks.

SWJs can occur during fixation tasks as well as during pursuit tasks. During pursuit tasks, the velocity of the eyes after a saccade should be the same as before the saccade, so that the pursuit of the target is not interrupted.

Figure 31:
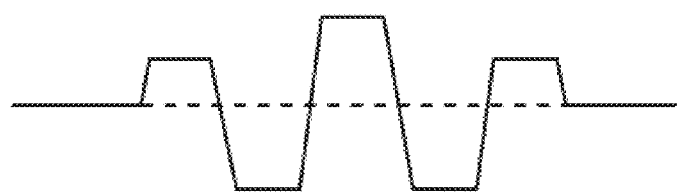
FIG. 31 is a graph illustrating a typical angular variation vs. time for a macrosaccadic oscillation, according to an embodiment.

Macrosaccadic Oscillations—Macrosaccades, as shown in FIG. 31, are oscillations around a fixation point due to saccadic hypermetria. They typically involve a run of usually horizontal saccades that build up then decrease in amplitude, with a usual intersaccadic interval of around 200 ms. These oscillations are normally induced by a gaze shift (saccade from one target to another).

Figure 32:
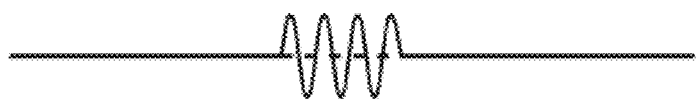
FIG. 32 is a graph illustrating a typical angular variation vs. time for an ocular flutter, according to an embodiment.

Ocular Flutter—Intermittent bursts of horizontal conjugate saccades, with no intersaccadic interval, often beginning after a voluntary saccade, as shown in FIG. 32. The oscillation frequency is 10-25 Hz, with smaller movements associated with a higher frequency. The movements are 1-5 degrees in amplitude.

Opsoclonus—Unlike ocular flutter, opsoclonus can have vertical and torsional components, resulting in multi-directional saccades. Opsoclonus presents as typically large, multi-directional, conjugate and random saccades that interfere with normal fixation and that are present during pursuit, convergence, blinks, eyelid closure and sleep.

5. Optical Flow

Optical flow is the representation of the apparent motion of areas of interest in a visual field with a vector field. As referred to herein, an "area of interest" may be any area of relatively high contrasts. It may be an entire object, or part of an object, or an abstract shape, or part of an abstract shape. The finer the areas of interest are, the denser the optical flow vector field is. The optical flow is thus the computation of the displacement of one or more areas of interest between two images. In other terms, to determine the optical flow, the system determines the displacement of one or more areas of interest between two images.

While the method for determining a neurological disease using gaze tracking method by generating the gaze predictions as described herein may be accurate, such a method based on the gaze predictions only may suffer from a large amount of intra- and inter-user variability. For example, some users may in general have better gaze accuracy than others, and the accuracy of one user may vary, sometimes significantly, from session to session in response to changes in their environment, for example.

Additionally, even in the best cases, the gaze predictions may have an amount of noise that may make it difficult or impossible to extract certain features. Notably, an increase in noise levels may make the measurements of saccades (latency, amplitude, peak velocity) unreliable. An alternative method to obtain information about the movement of the user's eyes is provided below.

It should be noted that for many features extracted, it is not necessary to know the absolute position of the gaze for all frames, but merely to observe relative changes. For example, when measuring the amplitude of a saccade, the system and method that has a systematic bias in its gaze estimation may still be used because the amplitude of the saccade is not affected by this bias. So long as changes in the estimated gaze position are commensurate with changes in actual position, there may be no need for the gaze estimates to be accurate.

In an alternative method described herein, an additional data stream is obtained from performing optical flow (OF) on the face and each eye of the user, in other terms based on determining the optical flow on the face and each eye of the user. The optical flow of the eyes provides information about the actual eye movement. The optical flow of the face, or some facial structures, provides information regarding a form of stabilization.

An optical flow method tracks a set of areas of interest from one image to the next image of the video frame of the video of the user's face generated as described above. The method determines where each area of interest in a set of areas of interest taken from one image (video frame) of the video of the user's face is in a new image.

The system selects which areas of interest to track. A "good" area of interest to track is one that has many edges in different orientations, that have a so-called "signature" or high contrast which characterize this area to facilitate its tracking in space over time. For example, when tracking a black square on a white background, it is preferable to track such areas of interest as corners. Selection of the areas of interest may be done manually or, preferably, algorithmically. For example, the operator may determine the areas of interest, or the system may determine algorithmically, based on contrast levels on an image (from the video of the user's face). Alternatively, the system may extract at least one image from the video of the user's face and, based on the contrast in various areas of that image, determine a area of interest for that video of the user's face.

Performing optical flow (measuring the optical flow) on the eyes permits to directly measure the apparent (visible) movement of the structures of an eye such as, for example, eyelids, eyelashes, limbus, pupil when visible relative to structures of the face around it such as, for example, canthi, eyebrow, nose of the bridge, etc. Such information of the movement of the structures of the eye provides information about rotation of the eyeball, without having to go through the process of gaze estimation as described above.

As the eyes are bound to the user's head, any head movements also cause apparent eye movements in the frame. Thus, the optical flow measurement may be performed on areas (regions) of the patient's face. That movement (face or head movement of the user's face or head, respectively) then is subtracted to the overall movement of the eyes, which leaves (provides) the movement of the eyes relative to the head. The system may thus detect movement of the eye (one or both eyes), which may comprise detecting an eventuality of user's movement of eye(s) (whether there was actually any movement of the eye(s), or whether the eye's velocity is zero) and a velocity of the movement of the eye(s) by measuring movement of areas of interest on the video of the user's face for each one of the stimulus videos.

The system determines the displacement of each tracked area of interest from one frame to the next, which is the instant velocity of each tracked area of interest, which may be also referred to as a framerate. Therefore, an overall instant velocity vector may be determined by averaging together the velocity vectors of each tracked area of interest.

Thus, detecting the movement of the eye by using the optical flow, comprises measuring an optical flow in areas of interest located on patient's face to generate face movement. The method comprises also subtracting the face movement to an overall movement of the eyes thus generating movement of the eyes relative to the head thus generating a displacement of each tracked area of interest from one frame of the video to the next, which is an instant velocity of each tracked area of interest (=framerate). Then, the system averages the velocity vectors of each tracked area of interest to generate an overall instant velocity vector for all areas of interest. In other terms, detecting movement of the eye further comprises: determining a area of interest for user's eye and a area of interest for user's face in at least one image of the video of the user's face; measuring an eye movement of at least one eye structure of user's eye; measuring a face movement of the user's face; generating a relative eye movement of the user's eye relative to user's head by subtracting the face movement to an overall movement of the eyes; averaging velocity vectors of each tracked area of interest to generate an overall instant velocity vector for the areas of interest; and based on the overall instant velocity vector, determining an eventuality of user's movement of eyes and a velocity of the movement of the eyes.

All the measured elements derived as described above are expressed in terms of pixels. The system as described herein may convert these measurements into angles of rotation of the eye. To do so, the system first determines how large the movement was physically. That is, the system determines what is the actual distance that a movement of X pixels represents. To determine the actual distance of the movement, anthropometric data may be used. For example, the available anthropometric data may provide that the palpebral fissure (the slit of the eye) is 30 mm long in adults, with little variation. Since the apparent length in pixels of the palpebral fissure may be measured by the system, and since the displacement of the eye in pixels is measured as described above, a simple rule of three converts this displacement into millimeters. Then, given a known distance between the user and the device, the system may use trigonometric relations to convert this displacement into an amount of rotation of the eyeball, which allows to generate an instantaneous angular velocity for the eyeball.

The optical flow method as described herein does not generate an absolute gaze position or eyeball angle, but the optical flow method detects changes in eye's position over time. Detection of such changes in eye's position over time may be of much greater accuracy than the method of gaze estimation and generation of gaze predictions as described above.

The optical flow method as described herein provides much greater sensitivity and accuracy when determining when an event, such as, for example, a saccade, took place. The optical flow method may allow to detect the events so small that they would typically be buried in the noise of the gaze estimation signals. Examples may include saccadic intrusions in the fixation task and the nystagmus of the OKN task.

The optical flow signal may be used to detect and to time (in other terms, to determine the time of) the events (such as, for example, detection of small saccades, saccade latency). The optical flow signal generated with the optical flow method may also provide measurements of the amplitude and/or velocity of the events.

The optical flow signal may be unsuitable when the actual position of the gaze on the screen needs to be determined. As the algorithm outputs a velocity signal, the system may only derive a relative positional signal from it. Some reasonable assumptions may be made in some cases to determine that the gaze was in a known position at a known time to adjust the signal, but in cases where this would be necessary, a great precision in the gaze position is not required and so the gaze signal may be used instead.

The optical flow method as described herein determines movement of the eyes, without determining where the eyes look (the person looks) at the screen 502, just determining the relative displacement of the eyes, by determining movements of the head, and determining the difference. Therefore, the very high signal-to-noise ratio associated to the optical flow method makes it highly suitable for detection of events of ocular motion of small amplitude that would otherwise be hard to detect (including with the method of gaze predictions which does not have a signal-to-noise ratio as high as the one associated to the optical flow method). Meanwhile, contrarily to the optical flow method, the method of gaze predictions remains useful to determine a position of the gaze, which implies that it is advantageous to use both methods in conjunction (both being used simultaneously or concurrently) with the other.

The optical flow method may be used in addition to the gaze predictions method described above. The optical flow method measures the displacement in the video and there is no need to train a machine learning model in order to implement the optical flow method. The optical flow method generates, as an output, the optical flow signal that is less noisy compared to the signal (output) generated by the gaze predictions method described above. In particular, the absence of needing to train an algorithm to perform the optical flow signal makes it suitable to make some determinations or detections without suffering from any bias that could arise from the training.

By using the optical flow method as described herein in conjunction with (combined with) the method for detecting a neurological disease based on gaze predictions, the accuracy of the method of detecting a neurological disease may be improved. For example, where the eventuality of the saccade could not be determined because of the noise in the method based on the gaze predictions only, the use of the optical flow may help to detect such a saccade. Similarly, even if the saccade may be determined using the method based on the gaze predictions, using the data obtained with the optical flow method may help to improve the accuracy of the determination of the neurological disease. For example, using gaze predictions only can be used to detect saccades having an amplitude higher than between about 1 degree and about 2 degrees, while using gaze predictions along with optical flow can be used to detect saccades having an amplitude higher than between about 0.25 degree and about 0.5 degrees, thereby making the threshold for ocular event detection smaller, that is events of smaller amplitude can thereby be detected.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for detecting a neurological disease, the method comprising:
performing a set of tasks, each task being distinct from each other and corresponding to a distinct set of features for the task, the set of tasks having a calibration task, and at least one of a smooth pursuit task, a fixation task, a pro-saccade task and an anti-saccade task,
performing the set of tasks comprising, for each task, displaying stimulus videos on a screen of an electronic device and simultaneously filming with a camera of the electronic device, the camera located in proximity to the screen, to generate a video of a user's face for each one of the stimulus videos, each one of the stimulus videos corresponding to a task of the set of tasks, a stimulus video comprising displaying a target in a sequence on the screen following a predetermined continuous or disconnected path and the target appearing moving at a pre-determined speed on the screen, the stimulus video prompting the user to deliberately follow the movement of the target on the screen during displaying of the stimulus video, each one of the stimulus video being configured for extraction of the distinct set of features;
providing a machine learning model for gaze predictions;
based on the generated videos for the tasks and using the machine learning model, generating the gaze predictions for each video frame of each video of the user's face for each task;
based on the generated gaze predictions for each video frame of each video of the user's face for each task, determining values of the set of features for each task; and
based on the values of the set of features determined for each task, detecting the neurological disease using a pre-trained machine learning model,
wherein providing the machine learning model comprises using another pre-trained model into which calibration data obtained during the calibration task is fed to perform the gaze predications, and using the other pre-trained model comprises using an internal representation of the machine learning model to perform the gaze predications.

2. The method of claim 1, wherein the calibration task comprises performing an alignment of the eyes of the user with respect to a form displayed on the screen, requesting the user to tilt the head to one side during a first period of the calibration task and to another side during a second period of the calibration task.

3. The method of claim 1, further comprising determining, during the fixation task, metrics related to intrusions, comprising a square-wave jerk (SWJ) saccade metrics and other saccadic intrusions metrics, and metrics related to gaze drift and stability.

4. The method of claim 1, wherein during the pro-saccade task, following a displaying of a first target for a period of time, a second target is displayed in one of a set of pre-determined locations on the screen, and the following metrics are extracted: a first gain and a final gain, a saccadic velocity, a ratio of the peak velocity between both eyes, and a number of saccades required to reach a target.

5. The method of claim 1, wherein the anti-saccade task comprises at least three distinct video blocks, each video block being configured to present on the screen a pre-determined number of trials, each trial having a fixation period, a blank screen period and a stimulus period.

6. The method of claim 1, wherein the set of tasks further comprises an optokinetic nystagmus task which comprises displaying a contrast grating for a pre-determined period of time, the contrast grating moving across the screen.

7. The method of claim 6, wherein metrics are determined for each pair of slow drift and saccade, and based on the metrics, determining values of the set of features for the optokinetic nystagmus task.

8. The method of claim 1, further comprising a visuospatial implicit memory task which comprises displaying a sequence of original images and a sequence of modified images, each modified image corresponding to one original image and being displayed in the same order as the original image, each modified image having at least one object removed therefrom or added therein.

9. The method of claim 1, wherein detecting the neurological disease comprises determining an eye gaze-pattern abnormality related to the neurological disease, and determining the eye gaze-pattern abnormality comprises identifying eye movements in association to the stimulus videos being displayed.

10. The method of claim 9, wherein generating the gaze predictions further comprises determining an estimated gaze position over time in the video by:
receiving an image of at least one eye of the user from the video;
extracting at least one color component of the image to obtain a corresponding at least one component image;
for each one of the at least one component of the image, applying a respective primary stream to obtain a respective internal representation; and
determining the estimated gaze position in the image according to the respective internal representation of each one of the at least one component of the image.

11. The method of claim 1, wherein the set of tasks comprises:
the fixation task, the pro-saccade task, the anti-saccade task, an optokinetic nystagmus task, a smooth pursuit task, a spiral task, a visuospatial implicit memory task, and a picture free-viewing task.

12. The method of claim 1, wherein the set of tasks further comprises at least one of an optokinetic nystagmus task, a smooth pursuit task, a spiral task, and a picture free-viewing task, and wherein:
the set of features for the fixation task comprises at least one of: an average gaze position, an average gaze error, a number of saccadic intrusions, presence of nystagmus, direction of nystagmus, and a velocity of nystagmus;
the set of features for the pro-saccade task comprises at least one of: a saccade latency, vertical and horizontal saccade latencies, a peak saccade velocity, vertical and horizontal peak saccade velocity, a saccade endpoint accuracy, a number of reversals in acceleration, and a direction error rate;
the set of features for the anti-saccade task comprises at least one of: an arrow direction error rate, a saccade direction error rate, a correction rate, a saccade latency, and a peak saccade velocity;
the set of features for the optokinetic nystagmus task comprises at least one of: presence of nystagmus, velocity of nystagmus in a slow phase, velocity of nystagmus in a fast phase, a direction of nystagmus, an amplitude of nystagmus;
the set of features for the smooth pursuit task comprises at least one of: a velocity gain, an average lag, a number of reversals in acceleration, a gaze direction error, and time to correct gaze direction; and
the set of features for the spiral task comprises at least one of: an average gaze position error relative to stimulus for each trial, a deviation from stimulus path, an angular velocity error, maximal angular velocity, a measure of circularity of gaze pattern during each spiral revolution, and time during the trial at which error on position reaches a certain threshold.

13. The method of claim 1, further comprising detecting a progression of the neurological disease.

14. The method of claim 1, further comprising:
detecting movement of the user's eye by measuring movement of areas of interest on the video of the user's face for each one of the stimulus videos.

15. The method of claim 14, wherein detecting movement of the user's eye further comprises:
determining an area of interest for the user's eye and an area of interest for the user's face in at least one image of the video of the user's face;
measuring an eye movement of at least one eye structure of the user's eye;
measuring a face movement of the user's face;
generating a relative eye movement of the user's eye relative to the user's head by subtracting the face movement to an overall movement of the eyes;
averaging velocity vectors of each tracked area of interest to generate an overall instant velocity vector for the areas of interest; and
based on the overall instant velocity vector, determining an eventuality of the movement of the user's eye and a velocity of the movement of the user's eye.

16. A method for detecting a neurological disease, the method comprising:
displaying stimulus videos on a screen of an electronic device and simultaneously filming with a camera of the electronic device, the camera located in proximity to the screen, to generate a video of a user's face for each one of the stimulus videos, each one of the stimulus videos corresponding to a task of a set of tasks;
based on the generated video for each task, detecting movement of the user's eye by measuring movement of areas of interest on the video of the user's face for each one of the stimulus videos and determining features for each task using a first pre-trained machine learning model; and
based on the features determined for each task, detecting the neurological disease using a second pre-trained machine learning model.

17. The method of claim 16, wherein the set of tasks further comprises at least one of a fixation task, a pro-saccade task, an anti-saccade task, an optokinetic nystagmus task, a smooth pursuit task, a spiral task, a visuospatial implicit memory task and a picture free-viewing task, and wherein:
- the features for the fixation task comprise at least one of: an average gaze position, an average gaze error, a number of saccadic intrusions, presence of nystagmus, direction of nystagmus, and a velocity of nystagmus;
- the features for the pro-saccade task comprise at least one of: a saccade latency, vertical and horizontal saccade latencies, a peak saccade velocity, vertical and horizontal peak saccade velocity, a saccade endpoint accuracy, a number of reversals in acceleration, and a direction error rate;
- the features for the anti-saccade task comprise at least one of: an arrow direction error rate, a saccade direction error rate, a correction rate, a saccade latency, and a peak saccade velocity;
- the features for the optokinetic nystagmus task comprise at least one of: presence of nystagmus, velocity of nystagmus in a slow phase, velocity of nystagmus in a fast phase, a direction of nystagmus, an amplitude of nystagmus;
- the features for the smooth pursuit task comprise at least one of: a velocity gain, an average lag, a number of reversals in acceleration, a gaze direction error, and time to correct gaze direction;
- the features for the spiral task comprise at least one of: an average gaze position error relative to stimulus for each trial, a deviation from stimulus path, an angular velocity error, maximal angular velocity, a measure of circularity of gaze pattern during each spiral revolution, and time during the trial at which error on position reaches a certain threshold; and
- the features of the visuospatial implicit memory task comprise a target region of interest and an average total time within the target region of interest.

18. The method of claim 16, wherein detecting movement of the eye further comprises:
- determining an area of interest for the user's eye and an area of interest for the user's face in at least one image of the video of the user's face;
- measuring an eye movement of at least one eye structure of the user's eye;
- measuring a face movement of the user's face;
- generating a relative eye movement of the user's eye relative to the user's head by subtracting the face movement to an overall movement of the eyes;
- averaging velocity vectors of each tracked area of interest to generate an overall instant velocity vector for the areas of interest; and
- based on the overall instant velocity vector, determining an eventuality of the movement of the user's eye and a velocity of the movement of the user's eye.

\* \* \* \* \*